(12) United States Patent
Libutti et al.

(10) Patent No.: US 7,901,881 B2
(45) Date of Patent: Mar. 8, 2011

(54) DIAGNOSTIC TOOL FOR DIAGNOSING BENIGN VERSUS MALIGNANT THYROID LESIONS

(75) Inventors: Steven K. Libutti, North Potomac, MD (US); Chiara Mazzanti, Pisa (IT); Martha Zeiger, Baltimore, MD (US); Christopher Umbricht, Baltimore, MD (US)

(73) Assignees: The United States of America as represented by the Department of Health and Human Services, Washington, DC (US); The John Hopkins University, Baltimore, MD (US)

( * ) Notice: Subject to any disclaimer, the term of this patent is extended or adjusted under 35 U.S.C. 154(b) by 0 days.

(21) Appl. No.: 11/547,995

(22) PCT Filed: Apr. 11, 2005

(86) PCT No.: PCT/US2005/012289
§ 371 (c)(1),
(2), (4) Date: Dec. 21, 2007

(87) PCT Pub. No.: WO2005/100608
PCT Pub. Date: Oct. 27, 2005

(65) Prior Publication Data
US 2008/0145841 A1 Jun. 19, 2008

Related U.S. Application Data

(60) Provisional application No. 60/560,900, filed on Apr. 9, 2004, provisional application No. 60/622,643, filed on Oct. 26, 2004.

(51) Int. Cl.
C12Q 1/68 (2006.01)
G01N 33/53 (2006.01)
(52) U.S. Cl. .............................. 435/6; 435/7.1
(58) Field of Classification Search .................. None
See application file for complete search history.

(56) References Cited

U.S. PATENT DOCUMENTS

| | | | |
|---|---|---|---|
| 5,556,752 | A | 9/1996 | Lockhart et al. |
| 5,578,832 | A | 11/1996 | Trulson et al. |
| 5,593,839 | A | 1/1997 | Hubbell et al. |
| 5,599,695 | A | 2/1997 | Pease et al. |
| 5,631,734 | A | 5/1997 | Stern et al. |
| 2004/0219521 | A1 | 11/2004 | Tang et al. |

FOREIGN PATENT DOCUMENTS

| | | |
|---|---|---|
| EP | 0 721 016 | 7/1996 |
| EP | 0 728 520 | 8/1996 |
| EP | 0 785 280 | 7/1997 |
| EP | 0 799 897 | 10/1997 |
| EP | 1 756 303 | 2/2007 |
| WO | WO 95/22058 | 8/1995 |
| WO | WO 97/02357 | 1/1997 |
| WO | WO 97/27317 | 7/1997 |
| WO | WO 97/29212 | 8/1997 |
| WO | WO 00/63438 | 10/2000 |
| WO | WO 03/025135 | 3/2003 |
| WO | WO 03/054152 | 7/2003 |
| WO | WO 03/065873 | 8/2003 |
| WO | WO 03/104427 | 12/2003 |
| WO | WO 2005/100608 | 10/2005 |

OTHER PUBLICATIONS

Chory et al (PNAS, Nov. 1990, 87(22):8776-80).*
Natali et al (Cancer Research, Apr. 1995, 55:1787-1791).*
Tockman et al (Cancer Res., 1992, 52:2711s-2718s).*
Greenbaum et al. (Genome Biology, 2003, vol. 4, Issue 9, pp. 117.1-117.8).*
Le Roch et al (Genome Research, Nov. 2004, 14(11): 2308-2318).*
Lichtinghagen et al (European Urology, 2002, 42:398-406).*
Mazzaferri et al., "Long term impact of initial surgical and medical therapy on paillary and follicular thyroid cancer", Am J Pathol, 97(5), 418-428, Nov. 1994.
Mazzaferri, E. L., "Management of a solitary thyroid nodule", N. Engl. J. Med., 328(8), 553-559, Feb. 25, 1993.
Mazzanti et al., "Using gene expression profiling to differentiate benign versus malignant thyroid tumors", Cancer Res., Apr. 15, 2004 64(8), 2898-2903.
Axelsson et al., "Global Tumor RNA Expression in Early Establishment of Experimental Tumor Growth and Related Angiogenesis following Cox-Inhibition Evaluated by Microarray Analysis", Cancer Information, May 1, 2007, 3, 125-139.
Barden et al., "Classification of follicular thyroid tumors by molecular signature: results of gene profiling", Clinical Cancer Reserach, 9(5), 1792-1800, May 2003.
Barker et al., "Human c-kit oncogene on human chromosome 4", Am. J. Hum. Genet., 37, A143, 1985.
Becker et al., "E-Cadherin gene mutations provide clues to diffuse type gastric carcinomas", Cancer Res., 54(14), 3845-3852, Jul. 15, 1994.
Caraway et al., "Diagnostic pitfalls in thyroid fine-needle aspiration: a review of 394 cases", Diagn Cytopathol, 9(3), 345-350, 1993.
Cerutti et al., "A preoperative diagnostic test that distinguishes benign from malignant thyroid carcinoma based on gene expression", J Clin Invest., Apr. 2004, 113(8), 1234-1242.
Cerutti et al., "Molecular profiling of matched samples identifies biomarkers of papillary thyroid carcinoma lymph node metastasis", Cancer Res., Aug. 15, 2007, 67(16), 7885-7892.
Chee et al., "Accessing genetic information with high-density DNA arrays ", Science, 274(5287), 610-614, Oct. 25, 1996.
De Miguel et al., "Dissection of the c-Kit signaling pathways in mouse primordial germ cells by retroviral- mediated gene transfer", Proc. Nat. Acad. Sci., 99(16), 10458-10463, Aug. 16, 2002 Epub Jul. 24, 2002.
Durand et al., "Evaluation of gene expression profiles in thyroid nodule biopsy material to diagnose thyroid cancer", J Clin Endocrinol Metab., Apr. 2008, Epub: Jan. 22, 2008, 93(4), 1195-1202.
Eberwine, J., "Amplification of mRNA populations using aRNA generated from immobilized oligo(dT)-T7 primed cDNA", Biotechniques, 20(4), 584-591, Apr. 1996.

(Continued)

Primary Examiner — Sean E Aeder
(74) Attorney, Agent, or Firm — Woodcock Washburn LLP

(57) ABSTRACT

The present invention relates to the use of genes differentially expressed in benign thyroid lesions and malignant thyroid lesions for the diagnosis and staging of thyroid cancer.

36 Claims, 7 Drawing Sheets

OTHER PUBLICATIONS

Eszlinger et al., "Perspectives and limitations of microarray-based gene expression profiling of thyroid tumors", Endocr Rev., May 2007, Epub: Mar. 12, 2007, 28(3), 322-338.

Feldman et al., "Advantages of mRNA amplification for microarray analysis", Biotechniques, 33(4), 906-912, 914, Oct. 2002.

Finley et al., "Discrimination of benign and malignant thyroid nodules by molecular profiling", Ann Surg., Sep. 2004, discussion 436-437, 240(3), 425-36.

Finley et al., "Molecular profiling distinguishes papillary carcinoma from benign thyroid nodules", J Clin Endocrinol Metab., Jul. 2004, 89(7), 3214-3223.

Fluge et al., "Gene expression in poorly differentiated papillary thyroid carcinomas", Thyroid., Feb. 2006, 16(2), 161-175.

Fryknäs et al., "Molecular markers for discrimination of benign and malignant follicular thyroid tumors", Tumour Biol., 2006, Epub: May 2, 2006, 27(4), 211-220.

GenBank Accession No. AB032954, Oct. 4, 1999.
GenBank Accession No. AL832414.1, Jan. 20, 2005.
GenBank Accession No. AP001717, Apr. 10, 2000.
GenBank Accession No. BC038512, Oct. 7, 2002.
GenBank Accession No. NM_000222, 1992.
GenBank Accession No. NM_001584, 1994.
GenBank Accession No. NM_004360, 1988.
GenBank Accession No. NM_004710, 1998.
GenBank Accession No. NM_006134, 1999.
GenBank Accession No. NM_014883, 1997.
GenBank Accession No. NM_016199, 1999.
GenBank Accession No. NM_018439, 2000.
GenBank Accession No. NP_060265, Aug. 11, 2003.
GenBank Accession No. X06182, 1987.

Gharib et al., "Fine-needle aspiration biopsy of the thyroid. The problem of suspicious cytologic findings", Ann Intern Med, 101(1), Jul. 25-28, 1984.

Goellner et al., "Fine needle aspiration cytology of the thyroid, 1980 to 1986", Acta Cytol, 31(5), 587-590, Sep.-Oct. 1987.

Goellner, J. R., "Problems and pitfalls in thyroid cytology", Monogr Pathol, (39), 75-93, 1997.

Golub et al., "Molecular classification of cancer: class discovery and class prediction by gene expression monitoring", Science, 286(5439), 531-537, Oct. 15, 1999.

Gordon et al., "Using gene expression ratios to predict outcome among patients with mesothelioma", J Natl Cancer hist, 95(8), 598-605, Apr. 16, 2003.

Hacia et al., "Detection of heterozygous mutations in BRCA1 using high density oligonucleotide arrays and two-colour fluorescence analysis", Nature Genetics 14(4), 441-447, Dec. 1996.

Hamberger et al., "Fine-needle aspiration biopsy of thyroid nodules. Impact on thyroid practice and cost of care", Am J Med, 73(3), 381-334, Sep. 1982.

Hoos et al., "Clinical significance of molecular expression profiles of Hürthle cell tumors of the thyroid gland analyzed via tissue microarrays", Am J Pathol., Jan. 2002, 160(1), 175-183.

Huang et al., "Gene expression in papillary thyroid carcinoma reveals highly consistent profiles", Proc Natl Acad Sci U S A., 98(26), 15044-15049, Dec. 18, 2001.

Jarząb et al., "Gene expression profile of papillary thyroid cancer: sources of variability and diagnostic implications", Cancer Res., Feb. 15, 2005, 65(4), 1587-1597.

Khan et al., "Classification and diagnostic prediction of cancers using gene expression profiling and artificial neural networks", Nat Med., Jun. 2001, 7(6), 673-679.

Kozal et al., "Extensive polymorphisms observed in HIV-1 clade B protease gene using high-density oligonucleotide arrays", Nature Medicine 2(7),753-759, Jul. 1996.

Lockhart et al., "Expression monitoring by hybridization to high-density oligonucleotide arrays", Nature Biotechnology 14(13), 1675-1680, Dec. 1996.

Lubitz et al., "Microarray analysis of thyroid nodule fine-needle aspirates accurately classifies benign and malignant lesions", J Mol Diagn., Sep. 2006, quiz 528, 8(4), 490-498.

Mazzaferri et al., "Long term impact of initial surgical and medical therapy on paillary and follicular thyroid cancer", Am J Pathol, 97(5), 418-428, Nov. 1994.

Mazzaferri, E. L., "Management of a solitary thyroid nodule", N. Engl. J. Med., 328(8), 553-559, Feb. 25, 1993.

Mazzanti et al., "Using gene expression profiling to differentiate benign versus malignant thyroid tumors", Cancer Res., Apr. 15, 2004, 64(8), 2898-2903.

Miller et al., "Optimal gene expression analysis by microarrays", Cancer Cell, 2(5), 353-361, Nov. 2002.

NCBI Database Accession No. GLP96, Mar. 11, 2002.

Needleman and Wunsch, "A general method applicable to the search for similarities in the amino acid sequence of two proteins", J. Mol. Biol., 48(3), 443, Mar. 1970.

Pearson and Lipman, "Improved tools for biological sequence comparison", Proc. Natl. Acad. Sci. U.S.A., 85(8), 2444-2448, Apr. 1988.

Perl et al., "A causal role for E- cadherin in the transition from adenoma to carcinoma", Nature, 392(6672): 190-193, Mar. 12, 1998.

Ravetto et al., "Usefulness of fine-needle aspiration in the diagnosis of thyroid carcinoma:a retrospective study in 37,895 patients", Cancer, 90(6): 357-363, Dec. 25, 2000.

Raychaudhuri et al., "Basic microarray analysis: grouping and feature reduction", Trends Biotechnol, 19(5): 189-193, May 2001.

Reboul et al., "Comparative genomic analysis of the interferon/interleukin-10 receptor gene cluster", Genome Res, 9(3), 242-250, Mar. 1999.

RHDB Database Accession No. PH93313, Jan. 29, 2010.

Sauter et al., "Perspective: Predictive molecular pathology", N Engl J Med, 347(25): 1995-1996, Dec. 19, 2002.

Schulze et al., "Navigating gene expression using microarrays—a technology review", Nat Cell Biol, 3(8): E 190-195, Aug. 2001.

Schwartz et al., "A WAGR region gene between PAX-6 and FSHB expressed in fetal brain", Hum. Genet., 94(6): 658-664, Dec. 1994.

Sherman, S. I., "Thyroid carcinoma", Lancet, 361(9536): 501-511, Feb. 8, 2003.

Simon et al., "Pitfalls in the use of DNA microarray data for diagnostic and prognostic classification", J Natl Cancer Inst, 95(1): 14-18, Jan. 1, 2003.

Siraj et al., "Genome-wide expression analysis of Middle Eastern papillary thyroid cancer reveals c-MET as a novel target for cancer therapy", J Pathol., Oct. 2007, 213(2), 190-199.

Smith and Waterman, "Comparison of bio-sequences", Adv Appl Mathematics 2: 482-489, 1981.

Staudt, L. M. "Gene expression profiling of lymphoid malignancies", Annu Rev Med, 53: 303-318, Feb. 2002.

Suen, K. C. "How does one separate cellular follicular lesions of the thyroid by fine- needle aspiration biopsy?", Diagn Cytopathol, 4(1): 78-81, Mar. 1988.

Tatusova and Madden, "BLAST 2 Sequences, a new tool for comparing protein and nucleotide sequences", FEMS Microbial. Lett. 174(2): 247-250, May 15, 1999.

Van de Vijver et al., "A gene-expression signature as a predictor of survival in breast cancer", N Engl J Med, 347(25): 1999-2009, Dec. 19, 2002.

Van't Veer and De Jong, "The microarray way to tailored cancer treatment", Nature Medicine, 8: 13-14, Jan. 1, 2002.

Wang et al., "High-fidelity mRNA amplification for gene profiling", Nat Biotechnol, 18(4): 457-459, Apr. 2000.

Weber et al., "Genetic Classification of Benign and Malignant Thyroid Follicular Neoplasia Based on a Three-Gene Combination", J Clin Endocr Metab, May 2005, Epub: Feb. 15, 2005, 90(5), 2512-2521.

West et al., "Predicting the clinical status of human breast cancer by using gene expression profiles", Proc Natl Acad Sci U S A, 98(20): 11462-11467, Sep. 25, 2001 Epub Sep. 18, 2001.

Wu et al., "Gene expression profiling of gastric cancer by microarray combined with laser capture microdissection", World J Gastroenterol., Dec. 21, 2005, 11(47), 7405-7412.

Xu et al., "Enhanced expression of nicotinamide N-methyltransferase in human papillary thyroid carcinoma cells", J Clin Endocrinol Metab., Oct. 2003, 88(10), 4990-4996.

Yarden et al. "Human proto-oncogene c-kit: a new cell surface receptor tyrosine kinase for an unidentified ligand" EMBO J. 6(11): 3341-3351, Nov. 1987.

* cited by examiner

FIG.6

SEQUENCE LISTING

```
<160> NUMBER OF SEQ ID NOS: 60

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 1
ggctgactgg caaaaagtct tg                                            22

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 2
ttggttccct taagttctca gagttt                                        26

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 3
tggccctgtc actcccatga tgc                                           23

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:/note =
      Synthetic Construct
```

<400> SEQUENCE: 4
aagggctcgc atgcaaag                                       18

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 5
cacagtagca ctctgagttg aagca                               25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 6
tttgtccctg cttgtactag tgagg                               25

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 7
gcaatcctct tacctccgct tt                                  22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 8
ggaatcggag acagaagaga gctt                                24

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 9
ctgggaccac agatgtatcc tccactcc                            28

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 10
atggcagtgc agtcatcatc tt                                         22

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 11
gcattcatac agctgcttac catct                                      25

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 12
tttggtccct gcctaggacc ggg                                        23

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 13
ccggcccaag ctccat                                                16

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 14
ttgtgtaacc gtcggtcatg a                                          21

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 15
tgtttggtgg aatccatgaa ggttatggc                                  29

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 16
gagagcgtga tcccccctaca                                           20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 17
accaagagtg cacctcagtg tct                                             23

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 18
tcacttccaa atgttcctgt agcataaatg gtg                                  33

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 19
tgccaaggag ctttgtttat agaa                                            24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 20
atgacggcat gtaccaacca                                                 20

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 21
ttggtcccct cagttctatg ctgttgtgt                                       29

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:/note = Synthetic Construct

<400> SEQUENCE: 22
gcacctgctg aaatgtatga cataat                                          26

<210> SEQ ID NO 23

```
<211> LENGTH: 28
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 23
tttgctaagt tggagtaaat atgattgg                                           28

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 24
attgttcagc taattgagaa gcagatttca gagagc                                  36

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 25
tgaagaatgt catggtggta gtatca                                             26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 26
atgactcctc aggtgaattt gtgtag                                             26

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 27
ctggtatgga gggattctgc taggaccag                                          29

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 28
tgagtgtccc ccggtatctt c                                                  21

<210> SEQ ID NO 29
<211> LENGTH: 21
<212> TYPE: DNA
```

```
<213> ORGANISM: Artificial Sequence
<220> FEATURE:
<223> OTHER INFORMATION: Description of Artificial Sequence:/note =
      Synthetic Construct

<400> SEQUENCE: 29
cagccgcttt cagattttca t                                              21

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 30
cctgccaatc ccgatgaaat tggaaat                                        27

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 31
gctggtgctc atggcactt                                                 19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 32
ccctccccag gcttcctaa                                                 19

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 33
aagggctttg cctgacaaca ccca                                           24

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 34
gacgatccgg gtaaagttcc a                                              21

<210> SEQ ID NO 35
<211> LENGTH: 20
<212> TYPE: DNA
<213> ORGANISM: Artificial Sequence
<220> FEATURE:
```

```
<223> OTHER INFORMATION: Description of Artificial Sequence:/note =
      Synthetic Construct

<400> SEQUENCE: 35
aggttgagga gtgggtcgaa                                                    20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 36
aggccgcgaa gccagtggaa tc                                                 22

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 37
tcaccagggc tgcttttaac tc                                                 22

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 38
ggaatcatat tggaacatgt aaacca                                             26

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:/note =
      Synthetic Construct

<400> SEQUENCE: 39
ttgccatcaa tgaccccttc attgacc                                            27

<210> SEQ ID NO 40
<211> LENGTH: 3084
<212> TYPE: DNA
<213> ORGANISM: Artificial Sequence
<220> FEATURE:
<223> OTHER INFORMATION: C21orf4

<400> SEQUENCE: 40
gctcccgggg ctgaggtgga gccgcgggac gccggcaggg ttgtggcgca gcagtctcct         60
tcctgcgcgc gcgcctgaag tcggcgtggg cgtttgagga agctgggata cagcatttaa        120
tgaaaaattt atgcttaaga agtaaaaatg gcaggcttcc tagataattt tcgttggcca        180
gaatgtgaat gtattgactg gagtgagaga agaaatgctg tggcatctgt tgtcgcaggt        240
atattgtttt ttacaggctg gtggataatg attgatgcag ctgtggtgta tcctaagcca        300
gaacagttga accatgcctt tcacacatgt ggtgtatttt ccacattggc tttcttcatg        360
```

```
ataaatgctg tatccaatgc tcaggtgaga ggtgatagct atgaaagcgg ctgtttagga    420
agaacaggtg ctcgagtttg cttttcatt ggtttcatgt tgatgtttgg gtcacttatt    480
gcttccatgt ggattctttt tggtgcatat gttacccaaa atactgatgt ttatccggga    540
ctagctgtgt tttttcaaaa tgcacttata ttttttagca ctctgatcta caaatttgga    600
agaaccgaag agctatggac ctgagatcac ttcttaagtc acattttcct tttgttatat    660
tctgtttgta gataggtttt ttatctctca gtacacattg ccaaatggag tagattgtac    720
attaaatgtt ttgttcttt acattttat gttctgagtt ttgaaatagt tttatgaaat    780
ttctttattt ttcattgcat agactgttaa tatgtatata atacaagact atatgaattg    840
gataatgagt atcagttttt tattcctgag atttagaact tgatctactc cctgagccag    900
ggttacatca tcttgtcatt ttagaagtaa ccactcttgt ctctctggcc gggcacggtg    960
gctcatgcct gtaatcccag cactttggga ggccgaggcg ggcgattgc ttgaggtcaa    1020 gtgttttgag accagcctgg ccaacatggc gaaaccccat ctactaaaaa tacaaaaatt    1080
agccaggcat ggtggtgggt gcctgtaatc ccaactacct aggaggctga ggcaggagaa    1140
tcgcttgaac ccgggggca gaggttgtag tgagctgagt ttgcgccact gcactctagc    1200
ctgggggaga aagtgaaact ccctctcaaa aaaagaagg accactctca gtatctgatt    1260
tctgaagatg tacaaaaaaa tatagcttca tatatctaga atgagcactg agccataaaa    1320
ggttttcagc aagttgtaac ttatttttggc ctaaaaatga ggtttttttg gtaaagaaaa    1380
aatatttgtt cttatgtatt gaagaagtgt acttttatat aatgattttt taaatgccca    1440
aaggactagt ttgaaagctt cttttaaaaa gaattcctct aatatgactt tatgtgagaa    1500
gggataatac atgatcaaat aaactcagtt ttttatggtt actgtaaaaa gactgtgtaa    1560
ggcagctcag caccatgctt ctcgtaaaag cagcttcaaa tatccactgg ggttatcttt    1620
tgacgacttg ccattatctg atgttacaca attcaatagc aagcaagttt gagacaatcg    1680
cagtttaaaa gcatgaacca tttaacaaaa agtggaataa ttaaagataa agcacttctt    1740
cccaaaggga attatcacct agtgaaaaat tatgcatttc atctactcag ttaccgactg    1800
caagtctctc ctcgctctag ctctcaagct ttgggtgaat attcctgtga aatatatctt    1860
caacttgaaa gttcatactc caatcaaaaa ctccttttac tgagtttgca gtactgtatt    1920
tgcactgttt gtattcctct gggcccttat tgctactttt gctttccttt gttacacaga    1980
ttttgtgttg cacttttct ccagagggggt gttgtagagc cttggttgta tgaataatac    2040
cagtggtagt gtccacggct ctaatgtaag cccatttggc atcactcctc tcctctctct    2100
tgagaggatt tcttgtgcac agagtatgaa gcagttgtgg agcgctgtgc ctttgtcaag    2160
ataccatctt gtttgatgac ttctttcttt gctgtttttt tcttcaaaat gttagtaagc    2220
tctgtcatgc ttctagcaaa ttgtaagact aattatttgt ttccacctca taacctgttg    2280
caataaatat tacttctcat acagtttaat attgttgttt gttggagaaa atgaaccata    2340
aaaattgatt tgctgttcag ttttcaatta ttcaagtata cccaattaaa gatgcagtta    2400
tgtttataaa ataagaagaa atagacttgt aaaatgctta tgtgagggtt attgaaggtt    2460
tccctgaaga ctgactggaa atggtggctg ttttttctta tttctgactc tgccatgaat    2520
tttttttttt tttttttaaa gacaatatct cactctgttg cctaggctgg agtgcagtgg    2580
tgcaaccaca gctcactgca ccttcaaatg ctggagctca ggcaatcctc ttacctccgc    2640
tttccaagca gctgggacca cagatgtatc ctccactcct cgctggccac catcctgctg    2700
cccaacagaa gaagctcttc tgtctccgat ttcctgaacg gtctaaggac caggaagaaa    2760
```

```
caggctcctg ccagcaccga cagcaacgaa aatgttccca cggagatcag gatgacttgc    2820
tgaagctcag tggaggctaa aagaggaca cgaaagtgaa cagaatgatc ttcctacgca    2880
caacacaaac atcagttaat gttccatcca tgctgcttaa agagcattcc tgtcctagta    2940
aaatgggcaa gtccctctac ccccccacct cacctggtat gcttacatta atagctaaag    3000
tcaatcctgt aatgaaataa agcaagtggt agctgtctgg tagcctccac tactgcaaat    3060
ctcaagaaaa aaaaaaaaaa aaaa                                          3084
```

<210> SEQ ID NO 41
<211> LENGTH: 158
<212> TYPE: PRT
<213> ORGANISM: Artificial Sequence
<220> FEATURE:
<223> OTHER INFORMATION: c21orf4

<400> SEQUENCE: 41

```
Met Ala Gly Phe Leu Asp Asn Phe Arg Trp Pro Glu Cys Glu Cys Ile
  1               5                  10                  15

Asp Trp Ser Glu Arg Arg Asn Ala Val Ala Ser Val Val Ala Gly Ile
                 20                  25                  30

Leu Phe Phe Thr Gly Trp Trp Ile Met Ile Asp Ala Ala Val Val Tyr
             35                  40                  45

Pro Lys Pro Glu Gln Leu Asn His Ala Phe His Thr Cys Gly Val Phe
         50                  55                  60

Ser Thr Leu Ala Phe Phe Met Ile Asn Ala Val Ser Asn Ala Gln Val
 65                  70                  75                  80

Arg Gly Asp Ser Tyr Glu Ser Gly Cys Leu Gly Arg Thr Gly Ala Arg
                 85                  90                  95

Val Trp Leu Phe Ile Gly Phe Met Leu Met Phe Gly Ser Leu Ile Ala
            100                 105                 110

Ser Met Trp Ile Leu Phe Gly Ala Tyr Val Thr Gln Asn Thr Asp Val
        115                 120                 125

Tyr Pro Gly Leu Ala Val Phe Phe Gln Asn Ala Leu Ile Phe Phe Ser
    130                 135                 140

Thr Leu Ile Tyr Lys Phe Gly Arg Thr Glu Glu Leu Trp Thr
145                 150                 155
```

<210> SEQ ID NO 42
<211> LENGTH: 2822
<212> TYPE: DNA
<213> ORGANISM: Artificial Sequence
<220> FEATURE:
<223> OTHER INFORMATION: Hs.145049

<400> SEQUENCE: 42

```
gtttctctga atagcagagg catcaaattt tggtggggaa tgagaggagt attaggggaa      60
agtttgaaaa tagctctcct ggagatggag ggcacacaga gtggtcctca ggctcacctt     120
gactgagttg attcacagtt atcctgcatc agaccattag atttctttag tgctatgatt     180
ataataggga ttttgaatc accaaaaaca gttttagat gttatgttc tttgttttac        240 tatcaatgtt gtgctggtta agggagagaa aagttcaaga agatcttaca tatttgaaag     300
gaaattggta ctcttgaagg ctatgcaaca tgagtctttg aacaagaatt ccttgctact     360
ttgattcatt catcaaatac tgagtgcctg tgtgccaggc acaggtgaac tctgggatt      420 caggggtaac taaaacagat tgcaaccctg cccttgtgaa gctttcagtc tagaaggag      480 acgtgaaaca aattttagct tcaaaagcaa catctatttt tgcctgttag catgcattta     540
```

```
ttttaaaagt catattagag ttacctggtt ccgcttcaga gcagactggg aaaatcaggc      600
ttacaatgga atcagatgct gtgggcctaa aacagctctt taaaaatcta ttttttttagg    660 ccaggtgcgt tggctcacac ctgtaatccc agcactttgg gaggccaagg tgggtggata     720
tgaggtcagg aggtcgagac cagcctggtc aatatgatga aaccttacct ctactaaaaa    780
taaaaaatta gccgggcatg gtggcacatg cctgtagtcc cagctactcg ggaaactgag     840
gcagaagaat cgcttgaacc cgggaggcgg aggttgcagt gagccgggat cacgtcactg     900
tactccagcc tgggcaagag tgagacaccg tctcaaaaaa aaaaaaaatt tttttttaaa    960
tggaatcaga gaaaccaaca aaatatgtaa catgtataaa tgcctgagga gatcagttat    1020
tgagaaatcc atttacaatg ctggaggaga ggggatggcc aggaaagaag tgcaacaaat    1080
aaatggaaga tgaccctaaa aatgcaccag tgacagtcag tcaatccatc agaccacctc    1140
acatgcaggg tagaaacatg gagtgtgcgg cagcatcctc ctcacatccc tttgtgagca    1200
cggctgctcc ggaatactga ccatctgggc tagcacgact tagcagaggg ttctgcagga    1260
tgtgctattt taaagcagct gggtgcaact tgtgaaaacg ggaatctaga gcagaacatg    1320
taatcagcga tggctgggat tggtggacag gattgacagg agtatttgag gctctaccag    1380
gcctgtctac aggacagctt catcaaaggg acatttttta acctgttatt ttaaatgcca    1440
catatatgtt gtaatgctga agcatacagg tagaatttct ggatcgtaac tactagtgac    1500
ttctgaggtt tacagttaga aaatgttctc aaaggtttat cagttatgta ttgatgattg    1560
gtaatctaga ccctctggag gctgtagaat gtgaaaagat acagctgagc tgacaagttt    1620
tagggcacta tcttctggaa tgaaatcggc caagaaaatg gttcaagggc atggggtta     1680 gagaatgttt cttttaccta aaaatgttaa gccaactatg gaagattggg gtcgtggggg    1740
catgaaatac aaaattatga taatttatac agaactaggt ttctttatgt tctgcaagaa    1800 ggttttttatt agctaatttg gggaggggg catgctgcag tattttttttt cctgggaaca   1860 tgcatttctg atgggaagtt attttgttta caagagttgg ttttacacac aaccctgaat    1920
gaatgtgtct atggcctaaa aatggtagac ctgtatttcc ttcccgaggc aggctgattc    1980
gtttcctgat tccttctgtc tgagattacc tgatgctgac cagacttatt tttcctttcc    2040
tgaatcttca cagctgagtt tatggcaccc atccaagacc ttcccatttg aatgactaga    2100
tttctattct atccccgatc atcctttga aatagttcta gtgataaact cagagaaatt     2160
caatatattg attgaatttt attttttcgc tttgtatcta caacagaaat tgatttgttc    2220
atttttattt caaatctctt catggcaagt tgggctaatg gactttgcac tcaagaaagg    2280 tttgttacc agttttgtag ccatgtttgg caaatcttag caactagaaa ccccgtcctt     2340
tcttttcctt ctttatatgt tcttgcagtt actcttgtat tgcaagattt tctgactta     2400 agctttgaga ctactgcatc ttaaaagaag aactaggctg actggcaaaa agtcttgcca    2460
gtggccctgt cactcccatg atgctttggt tttgagagtt gggaaaactc tgagaactta    2520
agggaaccaa actcaggaat cccaaaattg gtggcattgt gccattcgtt taggggctga    2580
acataggacc tgtctgaaac tgagtgagct agatgcattt gggtttgaat ttttgtcaca    2640
tactgaaatg taagtcagcc ctaaataatc aaaacacttt attttatttt tctttttta     2700 aataggaact ttctgaagaa aaagtggtgt gtaaaacatt tgatatttaa gacaataaag    2760 ttttatcat aaaaaaaaaa aaaaaaaaaa aaaaaaaaaa aaagaaaaa aaaaaaaaaa      2820 aa                                                                  2822
```

```
<210> SEQ ID NO 43
<211> LENGTH: 152
<212> TYPE: PRT
<213> ORGANISM: Artificial Sequence
<220> FEATURE:
<223> OTHER INFORMATION: Hs.145049

<400> SEQUENCE: 43

Met Val His Ser Pro Arg Ser Leu Val Ala Asn Pro Ser Gln Val Leu
  1               5                  10                  15

Phe Phe Leu Ser Phe Leu Phe Phe Phe Leu Arg Gln Ser Phe Ala
             20                  25                  30

Leu Val Ala Gln Ala Gly Val Gln Trp Arg Asn Leu Gly Ser Leu Gln
         35                  40                  45

Pro Pro Pro Pro Gly Phe Lys Gln Phe Ser Cys Leu Ser Leu Leu Ser
     50                  55                  60

Ser Trp Asp Tyr Arg His Ala Pro Pro Cys Pro Ala Tyr Phe Val Phe
 65                  70                  75                  80

Leu Val Asp Met Gly Phe Pro His Val Gly Gln Thr Gly Leu Glu Leu
                 85                  90                  95

Leu Thr Ser Gly Asp Pro Pro Ala Ser Ala Ser Gln Ser Ala Gly Ile
            100                 105                 110

Thr Gly Gly Ser His Arg Ala Gln Pro Thr Ser Ser Asn Pro Tyr Gly
        115                 120                 125

Ile Val Phe Phe Phe Leu Pro Val Lys Thr Phe Ser Gly Met Ser Gln
    130                 135                 140

Glu Ala Gly Asp Cys Arg Glu Thr
145                 150

<210> SEQ ID NO 44
<211> LENGTH: 4597
<212> TYPE: DNA
<213> ORGANISM: Artificial Sequence
<220> FEATURE:
<223> OTHER INFORMATION: Hs.296031

<400> SEQUENCE: 44
aatggtacga ttgagagatg agtgctatgg agaaaaatcc agccagaaag ggagatgcag     60
aagatagcac cagatcttct caatgttgtt ttcatcatgg acaggtgcgt tccttagaag    120
atgaagtgtt agtgattcct gagttttct caccttcacg tcgattgatc tgaatttgga    180
gagtctgttt tctgtgtctg gctctgcact caactttgta ggggaccctg tcgaggtccc    240
cacactgtgg cttcaggtag acagagcaga tgggagccca tttcagttca ttgtcttgct    300
gaccaatggg gaactgtggt caggtgagag gaggcagctt ttacaatcag acttcattga    360
atagtgtggg ctgctgtttc cttgtaacaa accccataa tgatggcagt ttccggatgt    420
gtctttttag gacttcagaa cttattattt gaatagaagt ttaaagcatc tggatgatga    480
tgctgtagct aaaacagctg cttgtcagaa gagaccctat ttaacacttc taaacttgtt    540
tcagaggtgg aggaaaggat aatctgggaa ggcctccctc tcaagtccac aggttggtat    600
cagctgtgtt catcccccaa aaggaaaata aaatgacaac aatattttgg tcacagaatt    660
cctgagaaac ctctgtttct atcttcatgt ctttaagata gggacatgaa ttccccatga    720
tctgggtgat agggttagag tggccaggac actgttactt tgtgtgtgac acaggtggct    780
cctcatgaca gttcctccat gccttagaac atgttgtctg tctggtcatc cctgggggta    840
gagctgagtg acccagcagt gggagattta acaactggag aagaagatgg gatgtgttta    900
attatcccca gaggtagggc caatttgtca cccttaaat agactatttt gcatataaac    960
```

```
taaagcacct tagggcatca ttaccgaaag tgtctaagca aatgtctgat atagttacgt    1020
gcctgcatta aaagaaagca gcccccttat cttgccttaa tatccttaca gtgttttaat    1080
aagttcataa tgcatcctgt atgtgcattt tttggtataa acaccgaaaa ggtggagaat    1140
tgacttcagt tctctccatc ctttccccct aagtgttggt ggcgctgcag gggcaacgtg    1200
cctcccattg gaagtggtga cttcctcttt gatagaggtt tgcctgtctc ttgaaaatga    1260
aaagaagcgg agattgatct ctggagtccc atggtccagt ttggactatt gggaatattt    1320
tttatgggat gttaaaaaca atattagaga cgtgagatag taaatttgtg gtaataccgg    1380
atccaggaag cttacagtga agagtatgaa cttaacctga aaagtatttc tctgttctat    1440
aaatctctca gtgacatttg gattaatcaa gcataattaa atgtagttag attttttgtca    1500 gattgtagtt caaaataata ttcatctatg gagagggtaa tatattatgt agaaatttta    1560
ttaagcactt tagttaagca aacactaagg agaacaaaat caacctcagg aaggttaatt    1620
actaaaaaaa tcacaaagta tagtagatta tgtaaatcat tttaattttg aataccatgg    1680
cttgagcttt aatttacata gagacgtatt ttggatttgt ttttcacatt atattttcta    1740
gtacaggatt gcaattgcat tcttgaaaag ttctactcat tttaggattc cattaagttt    1800
gcttaacttt tttcatgtta taatttccaa aagcaaagaa ttacaattgt attctagcta    1860
attattttaa tgtttcacta actttgtgtg tattgtaaga ccatattttt atttctatac    1920
aaatgatgat tttaagagaa gtatcaggag agagaatgta tatgaaagca tcgcgtccac    1980
gcctggcttt gcaataagtg ttcatttaaa agaaagacat ttacaaaggt aaaacataag    2040
agtttagact atagcgataa atcttttttat tttagtaatt tctttaaagg gaaaagtaaa    2100
gagatcaaaa tgattttata tgtattttt ttgtactcag agaattacat tttcactacc    2160
cccgcctgtc tcagggaata gcctttgata agaatcccat ggagatctct ggaactctat    2220
tacagtgtgt tcagatttgt tagttcatat gtaaatttca gagctagagc ttcaaaacta    2280
gagtattgta atctcaggaa cataagatta tccaagaagc ctgaaccttg ctcttttcat    2340
gataaatgac atccaaattt cctttgtcta ggagataagc atagatccct tttatcatgc    2400
ttctctgaga ttttcacaga acaaccctgc aatttgattt tgtttgataa ttttgctttt    2460
tggcttttca gtgaggactc tattttccat tggaactgac tcctttgggg ataataagct    2520
ttcacttaaa agaacattcc attagatagt tctaacttca atgaacctaa aagtggcttc    2580
ttaatttgaa taatctggat aacttttgca aatgggtcaa aacagcacaa gtatcaacaa    2640
tcacgtatgt actgagtaat atttgccctc cagttagcaa agtcaagaaa tgtctaactc    2700
tggcacacag cactggtttt aactactctt tagttcatct ttgccttcca aattggttga    2760
aaatggcaag cttagaatgg aatgcatatt aataacagaa ccacttaatg ttttaaaata    2820
ttcataccct gagattcttt tgagagaaa aaagaaatct taacatccaa ttctagttgt    2880
tttggctttt cacatatgct agacatgaaa aaggcagtta caaagtgaaa atccgattgg    2940
aagtcagtgg tgtccgccat tgagccgtgc taaatgtcgt gtcacaaaag gagtttgtga    3000
aaacaggatg agtagaaaat gttatactgt tgtttctatc gtggcaccgc tttcttataa    3060
attccatttg cttttttgtca tctgaactgt tacaaccatg ggaaacctca gtccatattt    3120
ttaaaagcac tatatactta caggaaaaac cgacttatgc cttcattgaa aaaatgttga    3180
agttaatatc ccaaatgttt aatgagcatg ttttagaata tttacagcta aagtctgtca    3240
ctttagggat ttgacaaaac ttgagactgc ctgccaccga agagggacca ggcagaatct    3300
tctcagcctt gtaaccagcg ttaaaaaaat ataaggggct tgatgagatc ctagatctgc    3360
```

-continued

```
tccttttctc ctaggtgcct gggtaactcc tggggaaagc atcatattaa gtccttttca    3420
agcaaggtgt gtgattttga ccaatgaatt gagctgatat gtgattttga ccaatgaatt    3480
gtgcatctat ttaaaaatta ccaagtgtat cttgactctt gagtggacag tcaaggcaaa    3540
gtttacttag gaaatgtaaa gtatggagtg ttttaaaaaa ttcaaattga gtttattcac    3600
tgttggagga attgaattct attgcctccc tcatttcaat tatgttcatt gttacaattg    3660
tgctgctctg ttctcattgt gatgcttagt tctcgtgtag aactgagtgc tacattgtga    3720
ttagaaactg gagttgtgct tgagtcagtc ctggaaaaca ggaccccattt ttaagaagaa   3780 cggaacatac cactttggca ttctggctga ccctaatttc tgcagagttc cttggtgtta    3840
aaatcatttg aggtcatagt tgctgcttat ggtttatata cacaccatct gctgctctaa    3900
gttcacatcc tctcaaaagc atgcaagtgc ttgaaattta atatttccc agatctaaaa     3960 caacttgtga ctacctaaga aatgcttgaa ccaaataaga aacagcactg tggaataaaa    4020
tataccattg tgaacatatc tgatgctgca atgaaatgta aagttcctta ctttgctgat    4080
ttttcatcat aactccttga ctcataaaag cggtgtctaa actgggaaca gctgctaata    4140
gggtaaaagt attatacatc aaataaaagt tcattacaat atttgtactc ataagtcaaa    4200
atctgacctg gttcgctttg tgcctctgtc agcctactta cagtgataaa tgtacacaca    4260
agtccagtgt tgccaaggag ctttgtttat agaaagaagc ttggtcccct cagttctatg    4320
ctgttgtgtg gcctggttgg tacatgccgt catgatgaag gatgactttg gtttgagata    4380
atttgtcact ccacattcca tggagaaaag tgtttcattt tgatgttgga aaaacatgac    4440
cagagaagca tgtgactcag ataatgttcc ccggaagttg cagagcaatc tgtggtgtct    4500
gtcatagccc aactagtcct ggagcacatg gacaattctg tacccaata atcagaacaa     4560 taaaatggta gttgtgattc aaaaaaaaaa aaaaaaa                             4597

<210> SEQ ID NO 45
<211> LENGTH: 5084
<212> TYPE: DNA
<213> ORGANISM: Artificial Sequence
<220> FEATURE:
<223> OTHER INFORMATION: KIT

<400> SEQUENCE: 45
gatcccatcg cagctaccgc gatgagaggc gctcgcggcg cctgggattt tctctgcgtt      60
ctgctcctac tgcttcgcgt ccagacaggc tcttctcaac catctgtgag tccaggggaa    120
ccgtctccac catccatcca tccaggaaaa tcagacttaa tagtccgcgt gggcgacgag    180
attaggctgt tatgcactga tccgggcttt gtcaaatgga cttttgagat cctggatgaa    240
acgaatgaga ataagcagaa tgaatggatc acggaaaagg cagaagccac caacaccggc    300
aaatacacgt gcaccaacaa cacggcttaa agcaattcca tttatgtgtt tgttagagat    360
cctgccaagc ttttccttgt tgaccgctcc ttgtatggga aagaagacaa cgacacgctg    420
gtccgctgtc ctctcacaga cccagaagtg accaattatt ccctcaaggg gtgccagggg    480
aagcctcttc ccaaggactt gaggtttatt cctgacccca aggcgggcat catgatcaaa    540
agtgtgaaac gcgcctacca tcggctctgt ctgcattgtt ctgtggacca ggagggcaag    600
tcagtgctgt cggaaaaatt catcctgaaa gtgaggccag ccttcaaagc tgtgcctgtt    660
gtgtctgtgt ccaaagcaag ctatcttctt agggaagggg aagaattcac agtgacgtgc    720
acaataaaag atgtgtctag ttctgtgtac tcaacgtgga aaagagaaaa cagtcagact    780
aaactacagg agaaatataa tagctggcat cacggtgact tcaattatga acgtcaggca    840
```

```
acgttgacta tcagttcagc gagagttaat gattctggag tgttcatgtg ttatgccaat    900
aatactttg  gatcagcaaa tgtcacaaca accttggaag tagtagataa aggattcatt    960
aatatcttcc ccatgataaa cactacagta tttgtaaacg atggagaaaa tgtagatttg   1020
attgttgaat atgaagcatt ccccaaacct gaacaccagc agtggatcta tatgaacaga   1080
accttcactg ataaatggga agattatccc aagtctgaga atgaaagtaa tatcagatac   1140
gtaagtgaac ttcatctaac gagattaaaa ggcaccgaag gaggcactta cacattccta   1200
gtgtccaatt ctgacgtcaa tgctgccata gcatttaatg tttatgtgaa tacaaaacca   1260
gaaatcctga cttacgacag gctcgtgaat ggcatgctcc aatgtgtggc agcaggattc   1320
ccagagccca aatagattg  gtattttgt  ccaggaactg agcagagatg ctctgcttct   1380
gtactgccag tggatgtgca gacactaaac tcatctgggc caccgtttgg aaagctagtg   1440
gttcagagtt ctatagattc tagtgcattc aagcacaatg gcacggttga atgtaaggct   1500
tacaacgatg tgggcaagac ttctgcctat tttaactttg catttaaagg taacaacaaa   1560
gagcaaatcc atccccacac cctgttcact cctttgctga ttggtttcgt aatcgtagct   1620
ggcatgatgt gcattattgt gatgattctg acctacaaat atttacagaa acccatgtat   1680
gaagtacagt ggaaggttgt tgaggagata aatggaaaca attatgttta catagaccca   1740
acacaacttc cttatgatca caaatgggag tttcccagaa acaggctgag ttttgggaaa   1800
accctgggtg ctggagcttt cgggaaggtt gttgaggcaa ctgcttatgg cttaattaag   1860
tcagatgcgg ccatgactgt cgctgtaaag atgctcaagc cgagtgccca tttgacagaa   1920
cgggaagccc tcatgtctga actcaaagtc ctgagttacc ttggtaatca catgaatatt   1980
gtgaatctac ttgagcctg  caccattgga gggcccaccc tggtcattac agaatattgt   2040
tgctatggtg atcttttgaa tttttgaga  agaaaacgtg attcatttat ttgttcaaag   2100
caggaagatc atgcagaagc tgcactttat aagaatcttc tgcattcaaa ggagtcttcc   2160
tgcagcgata gtactaatga gtacatggac atgaaacctg gagtttctta tgttgtccca   2220
accaaggccg acaaaaggag atctgtgaga ataggctcat acatagaaag agatgtgact   2280
cccgccatca tggaggatga cgagttggcc ctagacttag aagacttgct gagcttttct   2340
taccaggtgg caaagggcat ggctttcctc gcctccaaga attgtattca cagagacttg   2400
gcagccagaa atatcctcct tactcatggt cggatcacaa agatttgtga ttttggtcta   2460
gccagagaca tcaagaatga ttctaattat gtggttaaag gaaacgctcg actacctgtg   2520
aagtggatgg caccctgaaag cattttcaac tgtgtataca cgtttgaaag tgacgtctgg   2580
tcctatggga ttttttcttg ggagctgttc tctttaggaa gcagcccta  tcctggaatg   2640
ccggtcgatt ctaagttcta caagatgatc aaggaaggct tccggatgct cagccctgaa   2700
cacgcacctg ctgaaatgta tgacataatg aagacttgct gggatgcaga tccctaaaa   2760
agaccaacat tcaagcaaat tgttcagcta attgagaagc agatttcaga gagcaccaat   2820
catatttact ccaacttagc aaactgcagc cccaaccgac agaagcccgt ggtagaccat   2880
tctgtgcgga tcaattctgt cggcagcacc gcttcctcct cccagcctct gcttgtgcac   2940
gacgatgtct gagcagaatc agtgtttggg tcacccctcc aggaatgatc tcttcttttg   3000
gcttccatga tggttatttt cttttctttc aacttgcatc caactccagg atagtgggca   3060
ccccactgca atcctgtctt tctgagcaca ctttagtggc cgatgatttt tgtcatcagc   3120
caccatccta ttgcaaaggt tccaactgta tatattccca atagcaacgt agcttctacc   3180
atgaacagaa aacattctga tttggaaaaa gagagggagg tatggactgg gggccagagt   3240
```

```
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca ccataaggtt tcgtttctgt atacaaccct ggcattatgt ccactgtgta    3720
tagaagtaga ttaagagcca tataagtttg aaggaaacag ttaataccat tttttaagga    3780
aacaatataa ccacaaagca cagtttgaac aaaatctcct cttttagctg atgaacttat    3840
tctgtagatt ctgtggaaca agcctatcag cttcagaatg gcattgtact caatggattt    3900
gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080
agacaaatat ttggaggggt atttttgccc tgagtccaag agggtccttt agtacctgaa    4140
aagtaacttg gctttcatta ttagtactgc tcttgtttct tttcacatag ctgtctagag    4200
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tcttaaaaa caaacaaaa caaacaaaa    4440
aactcccctt cctcactgcc aatataaaa ggcaaatgtg tacatggcag agtttgtgtg    4500
ttgtcttgaa agattcaggt atgttgcctt tatggttcc cccttctaca tttcttagac    4560
tacatttaga gaactgtggc cgttatctgg aagtaaccat ttgcactgga gttctatgct    4620
ctcgcacctt tccaaagtta acagatttg gggttgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtctttt gaatattccc aagcccatga gtccttgaaa atatttttta tatatacagt    4980
aactttatgt gtaaatacat aagcggcgta agtttaaagg atgttggtgt tccacgtgtt    5040
ttattcctgt atgttgtcca attgttgaca gttctgaaga attc    5084
```

<210> SEQ ID NO 46
<211> LENGTH: 976
<212> TYPE: PRT
<213> ORGANISM: Artificial Sequence
<220> FEATURE:
<223> OTHER INFORMATION: KIT
<400> SEQUENCE: 46

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val

```
                     35                  40                  45
Arg Val Gly Asp Glu Ile Arg Leu Leu Cys Thr Asp Pro Gly Phe Val
             50                  55                  60
Lys Trp Thr Phe Glu Ile Leu Asp Glu Thr Asn Glu Asn Lys Gln Asn
 65                  70                  75                  80
Glu Trp Ile Thr Glu Lys Ala Glu Ala Thr Asn Thr Gly Lys Tyr Thr
                 85                  90                  95
Cys Thr Asn Lys His Gly Leu Ser Asn Ser Ile Tyr Val Phe Val Arg
                100                 105                 110
Asp Pro Ala Lys Leu Phe Leu Val Asp Arg Ser Leu Tyr Gly Lys Glu
                115                 120                 125
Asp Asn Asp Thr Leu Val Arg Cys Pro Leu Thr Asp Pro Glu Val Thr
    130                 135                 140
Asn Tyr Ser Leu Lys Gly Cys Gln Gly Lys Pro Leu Pro Lys Asp Leu
145                 150                 155                 160
Arg Phe Ile Pro Asp Pro Lys Ala Gly Ile Met Ile Lys Ser Val Lys
                165                 170                 175
Arg Ala Tyr His Arg Leu Cys Leu His Cys Ser Val Asp Gln Glu Gly
                180                 185                 190
Lys Ser Val Leu Ser Glu Lys Phe Ile Leu Lys Val Arg Pro Ala Phe
            195                 200                 205
Lys Ala Val Pro Val Val Ser Val Ser Lys Ala Ser Tyr Leu Leu Arg
    210                 215                 220
Glu Gly Glu Glu Phe Thr Val Thr Cys Thr Ile Lys Asp Val Ser Ser
225                 230                 235                 240
Ser Val Tyr Ser Thr Trp Lys Arg Glu Asn Ser Gln Thr Lys Leu Gln
                245                 250                 255
Glu Lys Tyr Asn Ser Trp His His Gly Asp Phe Asn Tyr Glu Arg Gln
                260                 265                 270
Ala Thr Leu Thr Ile Ser Ser Ala Arg Val Asn Asp Ser Gly Val Phe
                275                 280                 285
Met Cys Tyr Ala Asn Asn Thr Phe Gly Ser Ala Asn Val Thr Thr Thr
    290                 295                 300
Leu Glu Val Val Asp Lys Gly Phe Ile Asn Ile Phe Pro Met Ile Asn
305                 310                 315                 320
Thr Thr Val Phe Val Asn Asp Gly Glu Asn Val Asp Leu Ile Val Glu
                325                 330                 335
Tyr Glu Ala Phe Pro Lys Pro Glu His Gln Gln Trp Ile Tyr Met Asn
                340                 345                 350
Arg Thr Phe Thr Asp Lys Trp Glu Asp Tyr Pro Lys Ser Glu Asn Glu
            355                 360                 365
Ser Asn Ile Arg Tyr Val Ser Glu Leu His Leu Thr Arg Leu Lys Gly
    370                 375                 380
Thr Glu Gly Gly Thr Tyr Thr Phe Leu Val Ser Asn Ser Asp Val Asn
385                 390                 395                 400
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
                420                 425                 430
Phe Pro Glu Pro Thr Ile Asp Trp Tyr Phe Cys Pro Gly Thr Glu Gln
            435                 440                 445
Arg Cys Ser Ala Ser Val Leu Pro Val Asp Val Gln Thr Leu Asn Ser
    450                 455                 460
```

-continued

```
Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
                500                 505                 510

Lys Glu Gln Ile His Pro His Thr Leu Phe Thr Pro Leu Leu Ile Gly
                515                 520                 525

Phe Val Ile Val Ala Gly Met Met Cys Ile Ile Val Met Ile Leu Thr
530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
                595                 600                 605

Tyr Gly Leu Ile Lys Ser Asp Ala Ala Met Thr Val Ala Val Lys Met
610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
            770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895
```

```
Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
    930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Val
                965                 970                 975

<210> SEQ ID NO 47
<211> LENGTH: 489
<212> TYPE: DNA
<213> ORGANISM: Artificial Sequence
<220> FEATURE:
<223> OTHER INFORMATION: LSM7

<400> SEQUENCE: 47
cgcgacaaga tggcggataa ggagaagaag aaaaaggaga gcatcttgga cttgtccaag    60
tacatcgaca agacgatccg ggtaaagttc cagggaggcc gcgaagccag tggaatcctg   120
aagggcttcg acccactcct caaccttgtg ctggacggca ccattgagta catgcgagac   180
cctgacgacc agtacaagct cacggaggac acccggcagc tgggcctcgt ggtgtgccgg   240
ggcacgtccg tggtgctaat ctgcccgcag gacggcatgg aggccatccc caacccttc    300 atccagcagc aggacgccta gcctggccgg gggcgcgggg ggtgcagggc aggcccgagc   360
agctcggttt cccgcggact tggctgctgc tcccaccgca gtaccgcctc ctggaacgga   420
agcatttctc cttttgtat aggttgaatt tttgttttct taataaaatt gcaaacctca    480
aaaaaaaaa                                                           489

<210> SEQ ID NO 48
<211> LENGTH: 103
<212> TYPE: PRT
<213> ORGANISM: Artificial Sequence
<220> FEATURE:
<223> OTHER INFORMATION: LSM7

<400> SEQUENCE: 48

Met Ala Asp Lys Glu Lys Lys Lys Glu Ser Ile Leu Asp Leu Ser
  1               5                  10                  15

Lys Tyr Ile Asp Lys Thr Ile Arg Val Lys Phe Gln Gly Gly Arg Glu
            20                  25                  30

Ala Ser Gly Ile Leu Lys Gly Phe Asp Pro Leu Leu Asn Leu Val Leu
        35                  40                  45

Asp Gly Thr Ile Glu Tyr Met Arg Asp Pro Asp Gln Tyr Lys Leu
    50                  55                  60

Thr Glu Asp Thr Arg Gln Leu Gly Leu Val Val Cys Arg Gly Thr Ser
 65                 70                  75                  80

Val Val Leu Ile Cys Pro Gln Asp Gly Met Glu Ala Ile Pro Asn Pro
                85                  90                  95

Phe Ile Gln Gln Gln Asp Ala
            100

<210> SEQ ID NO 49
<211> LENGTH: 1694
<212> TYPE: DNA
<213> ORGANISM: Artificial Sequence
```

<220> FEATURE:
<223> OTHER INFORMATION: SYNGR2

<400> SEQUENCE: 49

```
ggcggcggca gcggcggcga cggcgacatg gagagcgggg cctacggcgc ggccaaggcg      60
ggcggctcct tcgacctgcg gcgcttcctg acgcagccgc aggtggtggc gcgcgccgtg     120
tgcttggtct tcgccttgat cgtgttctcc tgcatctatg gtgagggcta cagcaatgcc     180
cacgagtcta agcagatgta ctgcgtgttc aaccgcaacg aggatgcctg ccgctatggc     240
agtgccatcg gggtgctggc cttcctggcc tcggccttct tcttggtggt cgacgcgtat     300
ttcccccaga tcagcaacgc cactgaccgc aagtacctgg tcattggtga cctgctcttc     360
tcagctctct ggaccttcct gtggtttgtt ggtttctgct tcctcaccaa ccagtgggca     420
gtcaccaacc cgaaggacgt gctggtgggg ccgactctg tgagggcagc catcaccttc      480
agcttctttt ccatcttctc ctggggtgtg ctggcctccc tggcctacca gcgctacaag     540
gctggcgtgg acgacttcat ccagaattac gttgacccca ctccggaccc caacactgcc     600
tacgcctcct acccaggtgc atctgtggac aactaccaac agccacccct tcacccagaac    660
gcggagacca ccgagggcta ccagccgccc cctgtgtact gagcggcggt tagcgtggga     720
agggggacag agagggccct ccctctgcc ctggacttc ccatgagcct cctggaactg       780
ccagcccctc tctttcacct gttccatcct gtgcagctga cacacagcta aggagcctca     840
tagcctggcg ggggctggca gagccacacc ccaagtgcct gtgcccagag gcttcagtc      900
agccgctcac tcctccaggg cacttttagg aaagggtttt tagctagtgt ttttcctcgc     960
ttttaatgac ctcagccccg cctgcagtgg ctagaagcca gcaggtgccc atgtgctact    1020
gacaagtgcc tcagcttccc cccggccgg gtcaggccgt gggagccgct attatctgcg     1080
ttctctgcca aagactcgtg ggggccatca cacctgccct gtgcagcgga gccggaccag    1140
gctcttgtgt cctcactcag gtttgcttcc cctgtgccca ctgctgtatg atctgggggc    1200
caccaccctg tgccggtggc ctctgggctg cctcccgtgg tgtgagggcg gggctggtgc    1260
tcatggcact tcctccttgc tcccacccct ggcagcaggg aagggctttg cctgacaaca    1320
cccagcttta tgtaaatatt ctgcagttgt tacttaggaa gcctggggag gcaggggtg     1380
ccccatggct cccagactct gtctgtgccg agtgtattat aaaatcgtgg gggagatgcc    1440
cggcctggga tgctgtttgg agacggaata aatgttttct cattcagtct ccagtcattg    1500
gttgagccac agcctagggg ttggaggaag actccactct gggtacaccc ttaggggctg    1560
gctttatgga acttgtagtt tgaacaaggc agtggcaatc cgccccctcc agcctgcctg    1620
gctggccccc ttccctctgt ctggggtcgc attccgcaca agcctttcat caacatctta    1680
aaatagtaac tgtg                                                      1694
```

<210> SEQ ID NO 50
<211> LENGTH: 224
<212> TYPE: PRT
<213> ORGANISM: Artificial Sequence
<220> FEATURE:
<223> OTHER INFORMATION: SYNGR2

<400> SEQUENCE: 50

Met Glu Ser Gly Ala Tyr Gly Ala Ala Lys Gly Gly Ser Phe Asp
1               5                   10                  15

Leu Arg Arg Phe Leu Thr Gln Pro Gln Val Val Ala Arg Ala Val Cys
            20                  25                  30

Leu Val Phe Ala Leu Ile Val Phe Ser Cys Ile Tyr Gly Glu Gly Tyr

```
                     35                   40                   45
Ser Asn Ala His Glu Ser Lys Gln Met Tyr Cys Val Phe Asn Arg Asn
 50                  55                   60

Glu Asp Ala Cys Arg Tyr Gly Ser Ala Ile Gly Val Leu Ala Phe Leu
 65                  70                   75                   80

Ala Ser Ala Phe Phe Leu Val Val Asp Ala Tyr Phe Pro Gln Ile Ser
                     85                   90                   95

Asn Ala Thr Asp Arg Lys Tyr Leu Val Ile Gly Asp Leu Leu Phe Ser
                100                  105                  110

Ala Leu Trp Thr Phe Leu Trp Phe Val Gly Phe Cys Phe Leu Thr Asn
                115                  120                  125

Gln Trp Ala Val Thr Asn Pro Lys Asp Val Leu Val Gly Ala Asp Ser
                130                  135                  140

Val Arg Ala Ala Ile Thr Phe Ser Phe Phe Ser Ile Phe Ser Trp Gly
145                 150                  155                  160

Val Leu Ala Ser Leu Ala Tyr Gln Arg Tyr Lys Ala Gly Val Asp Asp
                165                  170                  175

Phe Ile Gln Asn Tyr Val Asp Pro Thr Pro Asp Pro Asn Thr Ala Tyr
                180                  185                  190

Ala Ser Tyr Pro Gly Ala Ser Val Asp Asn Tyr Gln Gln Pro Pro Phe
                195                  200                  205

Thr Gln Asn Ala Glu Thr Thr Glu Gly Tyr Gln Pro Pro Pro Val Tyr
                210                  215                  220

<210> SEQ ID NO 51
<211> LENGTH: 2272
<212> TYPE: DNA
<213> ORGANISM: Artificial Sequence
<220> FEATURE:
<223> OTHER INFORMATION: c11orf8

<400> SEQUENCE: 51
aatgcacagc ggtattgatg agtagatcct tggattcaga ggttggctga aacgcaccat      60
gcctgcttcc atcttttgct ctgtaaagtt gtgaattgct catgcctata gggaggaagg     120
atggcacatg ggattccttc tcaaggcaaa gttaccataa cggtggatga gtacagctca     180
aaccccaccc aggcattcac gcactacaac atcaaccaga gcagattcca gcctccacat     240
gtacatatgg tcgaccccat cccatatgac actccaaaac cagcgggcca cacgcggttt     300
gtctgcatct cagacacaca ctccagaaca gatggtatcc agatgcctta tggggacatc     360
cttctccaca caggcgattt caccgagctg ggactgccct cagaggttaa gaagtttaat     420
gactggttag gaaacctgcc atatgaatat aaaatagtga ttgctgggaa tcatgaactg     480
acatttgata aggaattcat ggcagacctt gttaaacagg actactaccg tttcccctct     540
gtgtccaaat tgaaaccaga ggactttgac aatgttcagt ccctcctgac aaacagtatt     600
tacttacaag attcggaggt aacagtgaag ggattcagga tatacggtgc accttggacc     660
ccgtggttta tggatggggg ctttaaccta cccagaggtc agtctctgct ggacaagtgg     720
aacctcatcc ctgagggcat tgacatactc atgacacatg gacctcctct aggttttcga     780
gactgggttc caaaggagct tcaaagagtg ggctgtgtgg agctgttaaa cacggttcag     840
aggcgagtcc ggcccaagct ccatgtgttt ggtggaatcc atgaaggtta tggcatcatg     900
accgacggtt acacaacgta catcaatgcc tcgacgtgta cagtcagctt caaccgacc      960
aaccctccaa ttatatttga ccttccaaac ccacagggtt cctgaagctc taaatgccct    1020
attggaatgt gagggaaggt ctataaactg ccatttttct aattataaac ttacattctc    1080
```

```
ttacttattt acaaaccctg tgagttcttt ttgtaaattg ttggaacaca aatgatgcta    1140
gaggttgtgc ttcttatttt attttatttt aaatggggca tccatttgaa atcagaggaa    1200
cattgtgaat ttgtaaaatg acttctgttt tctcaaaggc catgccattg taaattgtta    1260
gtgttcgcca aaggacagcc aagctttctt ttaaaaagtg ataaaagtct tatttaata    1320 tgctttaagc tgaaagaaaa aaaaataaga aacaggcagt gttttaaaaa ccaacacaga    1380
tttgcacaac tgtttaagag tattgtttga aatattttaa ttttcaatgt tttgttgttg    1440
ttgttttctt ggtaatgctt ctttttttgca gatgtggtcc caatttatag caatcttctc    1500
aacagaagta ggcatggaaa agacttcttt tcatactctc actataaaga aagctgcatt    1560
gagaagaaaa tggctgtcat ttaaaggatg gtttaactag tgagattcct attgtggtta    1620
tacaaggtct cattgtttgt ttgtttcttt taaattattt cagctttaaa aatacagaaa    1680
tggaatctgt caagagcagg tatttcatac ggttaaaaaa atgaacatgc agactccttt    1740
tcaatatggg tttatatata taagtatttt ttgtgtatta tgactacgtt aggagtttaa    1800
tattgtcaag gacagtacaa ctgcaaaggg atgctgtata gcagcacatc agaagtcgga    1860
aggaactgac acattctctc agagctcaag gtcttaaaga gcttgagtta aatctaggta    1920
cagttacagg catgtataga cttaaatgga tgcaatggaa gctaactaaa ataaggctta    1980
gttgtccttt ctatttaaat accccaagtt gtcttcttac ttcctctccc ctctcccatt    2040
ttgcactgtg tgtcgatgca atcttcgcta gcacaaaata ttgtcgctaa tagtcatttc    2100
tgttttccca ttgtaaatgc tgttgagctt tattctattt tatgttactt tgttaatgaa    2160
atttaggaaa gcagttgttt ctttaaattt attgtgatat tctatatcta gcggccttta    2220
tatgcaaata aaattgcaag atttttaaaa aaaaaaaaa aaaaaaaaa aa               2272
```

<210> SEQ ID NO 52  
<211> LENGTH: 294  
<212> TYPE: PRT  
<213> ORGANISM: Artificial Sequence  
<220> FEATURE:  
<223> OTHER INFORMATION: c11orf8

<400> SEQUENCE: 52

```
Met Ala His Gly Ile Pro Ser Gln Gly Lys Val Thr Ile Thr Val Asp
 1               5                  10                  15

Glu Tyr Ser Ser Asn Pro Thr Gln Ala Phe Thr His Tyr Asn Ile Asn
             20                  25                  30

Gln Ser Arg Phe Gln Pro Pro His Val His Met Val Asp Pro Ile Pro
         35                  40                  45

Tyr Asp Thr Pro Lys Pro Ala Gly His Thr Arg Phe Val Cys Ile Ser
     50                  55                  60

Asp Thr His Ser Arg Thr Asp Gly Ile Gln Met Pro Tyr Gly Asp Ile
 65                  70                  75                  80

Leu Leu His Thr Gly Asp Phe Thr Glu Leu Gly Leu Pro Ser Glu Val
                 85                  90                  95

Lys Lys Phe Asn Asp Trp Leu Gly Asn Leu Pro Tyr Glu Tyr Lys Ile
            100                 105                 110

Val Ile Ala Gly Asn His Glu Leu Thr Phe Asp Lys Glu Phe Met Ala
        115                 120                 125

Asp Leu Val Lys Gln Asp Tyr Tyr Arg Phe Pro Ser Val Ser Lys Leu
    130                 135                 140

Lys Pro Glu Asp Phe Asp Asn Val Gln Ser Leu Leu Thr Asn Ser Ile
145                 150                 155                 160
```

Tyr Leu Gln Asp Ser Glu Val Thr Val Lys Gly Phe Arg Ile Tyr Gly
                165                 170                 175

Ala Pro Trp Thr Pro Trp Phe Asn Gly Trp Gly Phe Asn Leu Pro Arg
            180                 185                 190

Gly Gln Ser Leu Leu Asp Lys Trp Asn Leu Ile Pro Glu Gly Ile Asp
        195                 200                 205

Ile Leu Met Thr His Gly Pro Pro Leu Gly Phe Arg Asp Trp Val Pro
    210                 215                 220

Lys Glu Leu Gln Arg Val Gly Cys Val Glu Leu Leu Asn Thr Val Gln
225                 230                 235                 240

Arg Arg Val Arg Pro Lys Leu His Val Phe Gly Ile His Glu Gly
                245                 250                 255

Tyr Gly Ile Met Thr Asp Gly Tyr Thr Thr Tyr Ile Asn Ala Ser Thr
                260                 265                 270

Cys Thr Val Ser Phe Gln Pro Thr Asn Pro Pro Ile Ile Phe Asp Leu
            275                 280                 285

Pro Asn Pro Gln Gly Ser
        290

<210> SEQ ID NO 53
<211> LENGTH: 4828
<212> TYPE: DNA
<213> ORGANISM: Artificial Sequence
<220> FEATURE:
<223> OTHER INFORMATION: CDH1

<400> SEQUENCE: 53
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaaagga cagcctattt ttccctcgac acccgattca agtgggcac     360 agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgccccatca ggcctccgtt tctggaatcc aagcagaatt     540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaaagaag gcaaggtttt ctacagcatc actggccaag agctgacac     720 accccctgtt ggtgtctttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga tgacaacaa     900 gcccgaattc acccaggagg tctttaaggg gtctgtcatg aaggtgctc ttccaggaac     960 ctctgtgatg gaggtcacag ccacagacgc ggacgatgat gtgaacacct acaatgccgc    1020
catcgcttac accatcctca gccaagatcc tgagctccct gacaaaaata tgttcacat    1080 taacaggaac acaggagtca tcagtgtggt caccactggg ctggaccgag agtttccc    1140 tacgtatacc ctggtggttc aagctgctga ccttcaaggt gagggggttaa gcacaacagc    1200 aacagctgtg atcacagtca ctgacaccaa cgataatcct ccgatcttca atcccaccac    1260

```
gtacaagggt caggtgcctg agaacgaggc taacgtcgta atcaccacac tgaaagtgac      1320
tgatgctgat gcccccaata ccccagcgtg ggaggctgta tacaccatat tgaatgatga      1380
tggtggacaa tttgtcgtca ccacaaatcc agtgaacaac gatggcattt tgaaaacagc      1440
aaagggcttg gattttgagg ccaagcagca gtacattcta cacgtagcag tgacgaatgt      1500 ggtaccttt gaggtctctc tcaccacctc cacagccacc gtcaccgtgg atgtgctgga       1560
tgtgaatgaa gcccccatct tgtgcctcc tgaaaagaga gtggaagtgt ccgaggactt        1620
tggcgtgggc caggaaatca catcctacac tgcccaggag ccagacacat ttatggaaca      1680
gaaaataaca tatcggattt ggagagacac tgccaactgg ctggagatta atccggacac      1740
tggtgccatt tccactcggg ctgagctgga cagggaggat tttgagcacg tgaagaacag      1800
cacgtacaca gccctaatca tagctacaga caatggttct ccagttgcta ctggaacagg      1860
gacacttctg ctgatcctgt ctgatgtgaa tgacaacgcc cccataccag aacctcgaac      1920
tatattcttc tgtgagagga atccaaagcc tcaggtcata aacatcattg atgcagacct      1980
tcctcccaat acatctccct tcacagcaga actaacacac ggggcgagtg ccaactggac      2040
cattcagtac aacgacccaa cccaagaatc tatcattttg aagccaaaga tggccttaga      2100
ggtgggtgac tacaaaatca atctcaagct catggataac cagaataaag accaagtgac      2160
caccttagag gtcagcgtgt gtgactgtga aggggccgcc ggcgtctgta ggaaggcaca      2220
gcctgtcgaa gcaggattgc aaattcctgc cattctgggg attcttggag gaattcttgc      2280
tttgctaatt ctgattctgc tgctcttgct gtttcttcgg aggagagcgg tggtcaaaga      2340
gcccttactg cccccagagg atgacacccg ggacaacgtt tattactatg atgaagaagg      2400
aggcggagaa gaggaccagg actttgactt gagccagctg cacaggggcc tggacgctcg      2460
gcctgaagtg actcgtaacg acgttgcacc aaccctcatg agtgtccccc ggtatcttcc      2520
ccgccctgcc aatcccgatg aaattggaaa ttttattgat gaaaatctga agcggctga      2580 tactgacccc acagccccgc cttatgattc tctgctcgtg tttgactatg aaggaagcgg      2640
ttccgaagct gctagtctga gctccctgaa ctcctcagag tcagacaaag accaggacta      2700
tgactacttg aacgaatggg gcaatcgctt caagaagctg gctgacatgt acggaggcgg      2760
cgaggacgac tagggactc gagagaggcg ggccccagac ccatgtgctg ggaaatgcag      2820
aaatcacgtt gctggtggtt tttcagctcc cttccttga gatgagtttc tggggaaaaa       2880
aaagagactg gttagtgatg cagttagtat agctttatac tctctccact ttatagctct      2940
aataagtttg tgttagaaaa gtttcgactt atttcttaaa gctttttttt tttttcccatc     3000 actctttaca tggtggtgat gtccaaaaga tacccaaatt ttaatattcc agaagaacaa      3060
ctttagcatc agaaggttca cccagcacct tgcagatttt cttaaggaat tttgtctcac      3120
ttttaaaaag aaggggagaa gtcagctact ctagttctgt tgttttgtgt atataatttt      3180
ttaaaaaaaa tttgtgtgct tctgctcatt actacactgg tgtgtccctc tgccttttt       3240 ttttttttta agacagggtc tcattctatc ggccaggctg gagtgcagtg gtgcaatcac      3300
agctcactgc agccttgtcc tcccaggctc aagctatcct tgcacctcag cctcccaagt      3360
agctgggacc acaggcatgc accactacgc atgactaatt ttttaaatat tgagacggg      3420 gtctccctgt gttacccagg ctggtctcaa actcctgggc tcaagtgatc ctcccatctt      3480
ggcctcccag agtattggga ttacagacat gagccactgc acctgcccag ctccccaact      3540
ccctgccatt ttttaagaga cagtttcgct ccatcgccca ggcctgggat gcagtgatgt      3600
gatcatagct cactgtaacc tcaaactctg gggctcaagc agttctccca ccagcctcct      3660
```

```
tttttatttttt ttgtacagat ggggtcttgc tatgttgccc aagctggtct taaactcctg    3720
gcctcaagca atccttctgc cttggccccc caaagtgctg ggattgtggg catgagctgc    3780
tgtgcccagc ctccatgttt taatatcaac tctcactcct gaattcagtt gctttgccca    3840
agataggagt tctctgatgc agaaattatt gggctctttt agggtaagaa gtttgtgtct    3900
ttgtctggcc acatcttgac taggtattgt ctactctgaa gacctttaat ggcttccctc    3960
tttcatctcc tgagtatgta acttgcaatg ggcagctatc cagtgacttg ttctgagtaa    4020
gtgtgttcat taatgtttat ttagctctga agcaagagtg atatactcca ggacttagaa    4080
tagtgcctaa agtgctgcag ccaaagacag agcggaacta tgaaaagtgg gcttggagat    4140
ggcaggagag cttgtcattg agcctggcaa tttagcaaac tgatgctgag gatgattgag    4200
gtgggtctac ctcatctctg aaaattctgg aaggaatgga ggagtctcaa catgtgtttc    4260
tgacacaaga tccgtggttt gtactcaaag cccagaatcc ccaagtgcct gcttttgatg    4320
atgtctacag aaaatgctgg ctgagctgaa cacatttgcc caattccagg tgtgcacaga    4380
aaaccgagaa tattcaaaat tccaaatttt ttcttaggag caagaagaaa atgtggccct    4440 aaaggggggtt agttgagggg tagggggtag tgaggatctt gatttggatc tcttttttatt    4500 taaatgtgaa tttcaacttt tgacaatcaa agaaaagact tttgttgaaa tagctttact    4560
gtttctcaag tgttttggag aaaaaaatca accctgcaat cacttttttgg aattgtcttg    4620 atttttcggc agttcaagct atatcgaata tagttctgtg tagagaatgt cactgtagtt    4680
ttgagtgtat acatgtgtgg gtgctgataa ttgtgtattt tctttggggg tggaaaagga    4740
aaacaattca agctgagaaa agtattctca aagatgcatt tttataaatt ttattaaaca    4800
attttgttaa accataaaaa aaaaaaaa                                      4828
```

<210> SEQ ID NO 54
<211> LENGTH: 882
<212> TYPE: PRT
<213> ORGANISM: Artificial Sequence
<220> FEATURE:
<223> OTHER INFORMATION: CDH1

<400> SEQUENCE: 54

```
Met Gly Pro Trp Ser Arg Ser Leu Ser Ala Leu Leu Leu Leu Leu Gln
 1               5                  10                  15

Val Ser Ser Trp Leu Cys Gln Glu Pro Glu Pro Cys His Pro Gly Phe
             20                  25                  30

Asp Ala Glu Ser Tyr Thr Phe Thr Val Pro Arg Arg His Leu Glu Arg
         35                  40                  45

Gly Arg Val Leu Gly Arg Val Asn Phe Glu Asp Cys Thr Gly Arg Gln
     50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
                 85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160
```

-continued

```
Ile Ser Cys Pro Glu Asn Glu Lys Gly Pro Phe Pro Lys Asn Leu Val
                165                 170                 175
Gln Ile Lys Ser Asn Lys Asp Lys Glu Gly Lys Val Phe Tyr Ser Ile
            180                 185                 190
Thr Gly Gln Gly Ala Asp Thr Pro Pro Val Gly Val Phe Ile Ile Glu
        195                 200                 205
Arg Glu Thr Gly Trp Leu Lys Val Thr Glu Pro Leu Asp Arg Glu Arg
    210                 215                 220
Ile Ala Thr Tyr Thr Leu Phe Ser His Ala Val Ser Ser Asn Gly Asn
225                 230                 235                 240
Ala Val Glu Asp Pro Met Glu Ile Leu Ile Thr Val Thr Asp Gln Asn
                245                 250                 255
Asp Asn Lys Pro Glu Phe Thr Gln Glu Val Phe Lys Gly Ser Val Met
            260                 265                 270
Glu Gly Ala Leu Pro Gly Thr Ser Val Met Glu Val Thr Ala Thr Asp
        275                 280                 285
Ala Asp Asp Asp Val Asn Thr Tyr Asn Ala Ala Ile Ala Tyr Thr Ile
    290                 295                 300
Leu Ser Gln Asp Pro Glu Leu Pro Asp Lys Asn Met Phe Thr Ile Asn
305                 310                 315                 320
Arg Asn Thr Gly Val Ile Ser Val Val Thr Thr Gly Leu Asp Arg Glu
                325                 330                 335
Ser Phe Pro Thr Tyr Thr Leu Val Val Gln Ala Ala Asp Leu Gln Gly
            340                 345                 350
Glu Gly Leu Ser Thr Thr Ala Thr Ala Val Ile Thr Val Thr Asp Thr
        355                 360                 365
Asn Asp Asn Pro Pro Ile Phe Asn Pro Thr Thr Tyr Lys Gly Gln Val
    370                 375                 380
Pro Glu Asn Glu Ala Asn Val Val Ile Thr Thr Leu Lys Val Thr Asp
385                 390                 395                 400
Ala Asp Ala Pro Asn Thr Pro Ala Trp Glu Ala Val Tyr Thr Ile Leu
                405                 410                 415
Asn Asp Asp Gly Gly Gln Phe Val Val Thr Thr Asn Pro Val Asn Asn
            420                 425                 430
Asp Gly Ile Leu Lys Thr Ala Lys Gly Leu Asp Phe Glu Ala Lys Gln
        435                 440                 445
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
```

| Pro | Ile | Pro | Glu | Pro | Arg | Thr | Ile | Phe | Phe | Cys | Glu | Arg | Asn | Pro | Lys |
|     | 595 |     |     |     | 600 |     |     |     |     | 605 |     |     |     |     |     |

Pro Gln Val Ile Asn Ile Ile Asp Ala Asp Leu Pro Pro Asn Thr Ser
    610             615                 620

Pro Phe Thr Ala Glu Leu Thr His Gly Ala Ser Ala Asn Trp Thr Ile
625             630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
            755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785             790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
        850                 855                 860

Trp Gly Asn Arg Phe Lys Lys Leu Ala Asp Met Tyr Gly Gly Gly Glu
865                 870                 875                 880

Asp Asp

<210> SEQ ID NO 55
<211> LENGTH: 5858
<212> TYPE: DNA
<213> ORGANISM: Artificial Sequence
<220> FEATURE:
<223> OTHER INFORMATION: FAM13A1

<400> SEQUENCE: 55
ccttccagcc atgtgggttc agcggaaaga gaagcaaaac cactcttcct aaaatgttag     60
aagctgctct tcgcttacct tggggccttt gcattgggag ctgttttttca catcaaagaa   120 tatgtgctga atggaatttt agtatttttgc tgtcgtttta atattttcgt ctggtcttcc   180
tcagttcttc cagacgcttt ctgagagaat ggggcagga gctctagcca tctgtcaaag    240
taaagcagcg gttcggctga agaagacat gaaaagata gtggcagtgc cattaaatga    300
acagaaggat tttacctatc agaagttatt tggagtcagt ctccaagaac ttgaacggca   360
ggggctcacc gagaatggca ttccagcagt agtgtggaat atagtggaat atttgacgca    420

```
gcatggactt acccaagaag gtcttttag ggtgaatggt aacgtgaagg tggtggaaca     480
acttcgactg aagttcgaga gtggagtgcc cgtggagctc gggaaggacg tgatgtctg     540 ctcagcagcc agtctgttga agctgtttct gagggagctg cctgacagtc tgatcacctc    600
agcgttgcag cctcgattca ttcaactctt tcaggatggc agaaatgatg ttcaggagag    660
tagcttaaga gacttaataa aagagctgcc agacacccac tactgcctcc tcaagtacct    720
ttgccagttc ttgacaaaag tagccaagca tcatgtgcag aatcgcatga atgttcacaa    780
tctcgccact gtatttgggc caaattgctt tcatgtgcca cctgggcttg aaggcatgaa    840
ggaacaggac ctgtgcaaca agataatggc taaaattcta gaaaattaca atccctgtt    900 tgaagtagag tatacagaaa atgatcatct gagatgtgaa acctggcta ggcttatcat     960 agtaaaagag gtctattata agaactccct gcccatcctt ttaacaagag gcttagaaag    1020
agacatgcca aaaccacctc caaaaaccaa gatcccaaaa tccaggagtg agggatctat    1080
tcaggcccac agagtactgc aaccagagct atctgatggc attcctcagc tcagcttgcg    1140
gctaagttat agaaaagcct gcttggaaga catgaattca gcagagggtg ctattagtgc    1200
caagttggta cccagttcac aggaagatga agacctctg tcacctttct atttgagtgc     1260
tcatgtaccc caagtcagca atgtgtctgc aaccggagaa ctcttagaaa gaaccatccg    1320
atcagctgta gaacaacatc ttttgatgt taataactct ggaggtcaaa gttcaggga     1380 ctcagaatct ggaacactat cagcatcttc tgccacatct gccagacagc gccgccgcca    1440
gtccaaggag caggatgaag ttcgacatgg gagagacaag ggacttatca acaaagaaaa    1500
tactccttct gggttcaacc accttgatga ttgtattttg aatactcagg aagtcgaaaa    1560
ggtacacaaa aatacttttg ttgtgctgg agaaggagc aagcctaaac gtcagaaatc       1620
cagtactaaa ctttctgagc ttcatgacaa tcaggacggt cttgtgaata tggaaagtct    1680
caattccaca cgatctcatg agagaactgg acctgatgat tttgaatgga tgtctgatga    1740
aaggaaagga aatgaaaaag atggtggaca cactcagcat tttgagagcc ccacaatgaa    1800
gatccaggag catcccagcc tatctgacac caaacagcag agaaatcaag atgccggtga    1860
ccaggaggag agctttgtct ccgaagtgcc ccagtcggac ctgactgcat tgtgtgatga    1920
aaagaactgg gaagagccta tccctgcttt ctcctcctgg cagcgggaga acagtgactc    1980
tgatgaagcc cacctctcgc cgcaggctgg gcgcctgatc cgtcagctgc tggacgaaga    2040
cagcgacccc atgctctctc ctcggttcta cgcttatggg cagagcaggc aatacctgga    2100
tgacacagaa gtgcctcctt ccccaccaaa ctcccattct ttcatgaggc ggcgaagctc    2160
ctctctgggg tcctatgatg atgagcaaga ggacctgaca cctgcccagc tcacacgaag    2220
gattcagagc cttaaaaaga agatccggaa gtttgaagat agattcgaag aagagaagaa    2280
gtacagacct tcccacagtg acaaagcagc caatccggag gttctgaaat ggacaaatga    2340
ccttgccaaa ttccggagac aacttaaaga atcaaaacta agatatctg aagaggacct     2400 aactcccagg atgcggcagc gaagcaacac actccccaag agttttggtt cccaacttga    2460
gaaagaagat gagaagaagc aagagctggt ggataaagca ataaagccca gtgttgaagc    2520
cacattggaa tctattcaga ggaagctcca ggagaagcga gcggaaagca gccgccctga    2580
ggacattaag gatatgacca agaccagat tgctaatgag aaagtggctc tgcagaaagc     2640
tctgttatat tatgaaagca ttcatggacg gccggtaaca aagaacgaac ggcaggtgat    2700
gaagccacta tacgacaggt accggctggt caaacagatc ctctcccgag ctaacaccat    2760
acccatcatt ggttccccct ccagcaagcg gagaagccct ttgctgcagc caattatcga    2820
```

```
gggcgaaact gcttccttct tcaaggagat aaaggaagaa gaggaggggt cagaagacga  2880
tagcaatgtg aagccagact tcatggtcac tctgaaaacc gatttcagtg cacgatgctt  2940
tctggaccaa ttcgaagatg acgctgatgg atttatttcc ccaatggatg ataaaatacc  3000
atcaaaatgc agccaggaca cagggctttc aaatctccat gctgcctcaa tacctgaact  3060
cctggaacac ctccaggaaa tgagagaaga aagaaaagg attcgaaaga aacttcggga  3120
ttttgaagac aacttttttca gacagaatgg aagaaatgtc cagaaggaag accgcactcc  3180
tatggctgaa gaatacagtg aatataagca cataaaggcg aaactgaggc tcctggaggt  3240
gctcatcagc aagagagaca ctgattccaa gtccatgtga ggggcatggc caagcacagg  3300
gggctggcag ctgcggtgag agtttactgt ccccagagaa agtgcagctc tggaaggcag  3360
ccttggggct ggccctgcaa agcatgcagc ccttctgcct ctagaccatt tggcatcggc  3420
tcctgtttcc attgcctgcc ttagaaactg gctggaagaa gacaatgtga cctgacttag  3480
gcattttgta attggaaagt caagactgca gtatgtgcac atgcgcacgc gcatgcacgc  3540
acacacacac acagtagtgg agctttccta acactagcag agattaatca ctacattaga  3600
caacactcat ctacagagaa tatacactgt tcttccctgg ataactgaga aacaagagac  3660
cattctctgt ctaactgtga taaaaacaag ctcaggactt tattctatag agcaaacttg  3720
ctgtggaggg ccatgctctc cttgacccca gttaactgca aacgtgcatt ggagccctat  3780
ttgctgccgc tgccattcta gtgacctttc cacagagctg cgccttcctc acgtgtgtga  3840
aaggttttcc ccttcagccc tcaggtagat ggaagctgca tctgcccacg atggcagtgc  3900
agtcatcatc ttcaggatgt ttcttcagga cttcctcagc tgacaaggaa ttttggtccc  3960
tgcctaggac cggtcatct gcagaggaca gagagatggt aagcagctgt atgaatgctg  4020
attttaaaac caggtcatgg gagaagagcc tggagattct ttcctgaaca ctgactgcac  4080
ttaccagtct gattttatcg tcaaacacca agccaggcta gcatgctcat ggcaatctgt  4140 ttgggggctgt tttgttgtgg cactagccaa acataaaggg gcttaagtca gcctgcatac  4200
agaggatcgg ggagagaagg ggcctgtgtt ctcagcctcc tgagtactta ccagagttta  4260 attttttttaa aaaaatctg cactaaaatc cccaaactga caggtaaatg tagccctcag  4320
agctcagccc aaggcagaat ctaaatcaca ctattttcga gatcatgtat aaaaagaaaa  4380
aaaagaagtc atgctgtgtg gccaattata attttttttca aagactttgt cacaaaactg  4440
tctatattag acattttgga gggaccagga aatgtaagac accaaatcct ccatctcttc  4500
agtgtgcctg atgtcacctc atgatttgct gttacttttt taactcctgc gccaaggaca  4560
gtgggttctg tgtccacctt tgtgctttgc gaggccgagc ccaggcatct gctcgcctgc  4620
cacggctgac cagagaaggt gcttcaggag ctctgcctta gacgacgtgt tacagtatga  4680
acacacagca gaggcaccct cgtatgtttt gaaagttgcc ttctgaaagg gcacagtttt  4740
aaggaaaaga aaaagaatgt aaaactatac tgacccgttt tcagttttaa agggtcgtga  4800
gaaactggct ggtccaatgg gatttacagc aacattttcc attgctgaag tgaggtagca  4860
gctctcttct gtcagctgaa tgttaaggat ggggaaaaag aatgcccttta agtttgctct  4920 taatcgtatg gaagcttgag ctatgtgttg gaagtgccct ggttttaatc catacacaaa  4980
gacggtacat aatcctacag gtttaaatgt acataaaaat atagtttgga attctttgct  5040
ctactgttta cattgcagat tgctataatt tcaaggagtg agattataaa taaaatgatg  5100
cactttagga tgtttcctat ttttgaaatc tgaacatgaa tcattcacat gaccaaaaat  5160
tgtgtttttt taaaaataca tgtctagtct gtcctttaat agctctctta aataagctat  5220
```

-continued

```
gatattaatc agatcattac cagttagctt ttaaagcaca tttgtttaag actatgtttt    5280
tggaaaaata cgctacagaa ttttttttta agctacaaat aaatgagatg ctactaattg    5340
ttttggaatc tgttgtttct gccaaaggta aattaactaa agatttattc aggaatcccc    5400
atttgaattt gtatgattca ataaaagaaa acaccaagta agttatataa aataaattgt    5460
gtatgagatg ttgtgttttc ctttgtaatt tccactaact aactaactaa cttatattct    5520
tcatggaatg gagcccagaa gaaatgagag gaagcccttt tcacactaga tcttatttga    5580
agaaatgttt gttagtcagt cagtcagtgg tttctggctc tgccgaggga gatgtgttcc    5640
ccagcaacca tttctgcagc ccagaatctc aaggcactag aggcggtgtc ttaattaatt    5700
ggcttcacaa agacaaaatg ctctggactg ggattttttcc tttgctgtgt tgggaatatg    5760
tgtttattaa ttagcacatg ccaacaaaat aaatgtcaag agttatttca taagtgtaag    5820
taaacttaag aattaaagag tgcagactta taattttc                            5858
```

<210> SEQ ID NO 56
<211> LENGTH: 1023
<212> TYPE: PRT
<213> ORGANISM: Artificial Sequence
<220> FEATURE:
<223> OTHER INFORMATION: FAM13A1

<400> SEQUENCE: 56

```
Met Gly Ala Gly Ala Leu Ala Ile Cys Gln Ser Lys Ala Ala Val Arg
  1               5                  10                  15

Leu Lys Glu Asp Met Lys Lys Ile Val Ala Val Pro Leu Asn Glu Gln
             20                  25                  30

Lys Asp Phe Thr Tyr Gln Lys Leu Phe Gly Val Ser Leu Gln Glu Leu
         35                  40                  45

Glu Arg Gln Gly Leu Thr Glu Asn Gly Ile Pro Ala Val Val Trp Asn
     50                  55                  60

Ile Val Glu Tyr Leu Thr Gln His Gly Leu Thr Gln Glu Gly Leu Phe
 65                  70                  75                  80

Arg Val Asn Gly Asn Val Lys Val Val Glu Gln Leu Arg Leu Lys Phe
                 85                  90                  95

Glu Ser Gly Val Pro Val Glu Leu Gly Lys Asp Gly Asp Val Cys Ser
            100                 105                 110

Ala Ala Ser Leu Leu Lys Leu Phe Leu Arg Glu Leu Pro Asp Ser Leu
        115                 120                 125

Ile Thr Ser Ala Leu Gln Pro Arg Phe Ile Gln Leu Phe Gln Asp Gly
    130                 135                 140

Arg Asn Asp Val Gln Glu Ser Ser Leu Arg Asp Leu Ile Lys Glu Leu
145                 150                 155                 160

Pro Asp Thr His Tyr Cys Leu Leu Lys Tyr Leu Cys Gln Phe Leu Thr
                165                 170                 175

Lys Val Ala Lys His His Val Gln Asn Arg Met Asn Val His Asn Leu
            180                 185                 190

Ala Thr Val Phe Gly Pro Asn Cys Phe His Val Pro Pro Gly Leu Glu
        195                 200                 205

Gly Met Lys Glu Gln Asp Leu Cys Asn Lys Ile Met Ala Lys Ile Leu
    210                 215                 220

Glu Asn Tyr Asn Thr Leu Phe Glu Val Glu Tyr Thr Glu Asn Asp His
225                 230                 235                 240

Leu Arg Cys Glu Asn Leu Ala Arg Leu Ile Ile Val Lys Glu Val Tyr
                245                 250                 255
```

```
Tyr Lys Asn Ser Leu Pro Ile Leu Leu Thr Arg Gly Leu Glu Arg Asp
            260                 265                 270

Met Pro Lys Pro Pro Lys Thr Lys Ile Pro Lys Ser Arg Ser Glu
            275                 280             285

Gly Ser Ile Gln Ala His Arg Val Leu Gln Pro Glu Leu Ser Asp Gly
            290                 295                 300

Ile Pro Gln Leu Ser Leu Arg Leu Ser Tyr Arg Lys Ala Cys Leu Glu
305                 310                 315                 320

Asp Met Asn Ser Ala Glu Gly Ala Ile Ser Ala Lys Leu Val Pro Ser
                325                 330                 335

Ser Gln Glu Asp Glu Arg Pro Leu Ser Pro Phe Tyr Leu Ser Ala His
            340                 345                 350

Val Pro Gln Val Ser Asn Val Ser Ala Thr Gly Glu Leu Leu Glu Arg
            355                 360                 365

Thr Ile Arg Ser Ala Val Glu Gln His Leu Phe Asp Val Asn Asn Ser
            370                 375                 380

Gly Gly Gln Ser Ser Glu Asp Ser Glu Ser Gly Thr Leu Ser Ala Ser
385                 390                 395                 400

Ser Ala Thr Ser Ala Arg Gln Arg Arg Gln Ser Lys Glu Gln Asp
                405                 410                 415

Glu Val Arg His Gly Arg Asp Lys Gly Leu Ile Asn Lys Glu Asn Thr
                420                 425                 430

Pro Ser Gly Phe Asn His Leu Asp Asp Cys Ile Leu Asn Thr Gln Glu
            435                 440                 445

Val Glu Lys Val His Lys Asn Thr Phe Gly Cys Ala Gly Glu Arg Ser
            450                 455                 460

Lys Pro Lys Arg Gln Lys Ser Ser Thr Lys Leu Ser Glu Leu His Asp
465                 470                 475                 480

Asn Gln Asp Gly Leu Val Asn Met Glu Ser Leu Asn Ser Thr Arg Ser
                485                 490                 495

His Glu Arg Thr Gly Pro Asp Asp Phe Glu Trp Met Ser Asp Glu Arg
            500                 505                 510

Lys Gly Asn Glu Lys Asp Gly Gly His Thr Gln His Phe Glu Ser Pro
            515                 520                 525

Thr Met Lys Ile Gln Glu His Pro Ser Leu Ser Asp Thr Lys Gln Gln
            530                 535                 540

Arg Asn Gln Asp Ala Gly Asp Gln Glu Glu Ser Phe Val Ser Glu Val
545                 550                 555                 560

Pro Gln Ser Asp Leu Thr Ala Leu Cys Asp Glu Lys Asn Trp Glu Glu
                565                 570                 575

Pro Ile Pro Ala Phe Ser Ser Trp Gln Arg Glu Asn Ser Asp Ser Asp
            580                 585                 590

Glu Ala His Leu Ser Pro Gln Ala Gly Arg Leu Ile Arg Gln Leu Leu
            595                 600                 605

Asp Glu Asp Ser Asp Pro Met Leu Ser Pro Arg Phe Tyr Ala Tyr Gly
            610                 615                 620

Gln Ser Arg Gln Tyr Leu Asp Asp Thr Glu Val Pro Pro Ser Pro Pro
625                 630                 635                 640

Asn Ser His Ser Phe Met Arg Arg Ser Ser Ser Leu Gly Ser Tyr
                645                 650                 655

Asp Asp Glu Gln Glu Asp Leu Thr Pro Ala Gln Leu Thr Arg Arg Ile
                660                 665                 670

Gln Ser Leu Lys Lys Lys Ile Arg Lys Phe Glu Asp Arg Phe Glu Glu
```

675                 680                 685
Glu Lys Lys Tyr Arg Pro Ser His Ser Asp Lys Ala Ala Asn Pro Glu
    690                 695                 700

Val Leu Lys Trp Thr Asn Asp Leu Ala Lys Phe Arg Arg Gln Leu Lys
705                 710                 715                 720

Glu Ser Lys Leu Lys Ile Ser Glu Glu Asp Leu Thr Pro Arg Met Arg
                725                 730                 735

Gln Arg Ser Asn Thr Leu Pro Lys Ser Phe Gly Ser Gln Leu Glu Lys
            740                 745                 750

Glu Asp Glu Lys Lys Gln Glu Leu Val Asp Lys Ala Ile Lys Pro Ser
        755                 760                 765

Val Glu Ala Thr Leu Glu Ser Ile Gln Arg Lys Leu Gln Glu Lys Arg
    770                 775                 780

Ala Glu Ser Ser Arg Pro Glu Asp Ile Lys Asp Met Thr Lys Asp Gln
785                 790                 795                 800

Ile Ala Asn Glu Lys Val Ala Leu Gln Lys Ala Leu Leu Tyr Tyr Glu
                805                 810                 815

Ser Ile His Gly Arg Pro Val Thr Lys Asn Glu Arg Gln Val Met Lys
            820                 825                 830

Pro Leu Tyr Asp Arg Tyr Arg Leu Val Lys Gln Ile Leu Ser Arg Ala
        835                 840                 845

Asn Thr Ile Pro Ile Ile Gly Ser Pro Ser Ser Lys Arg Arg Ser Pro
    850                 855                 860

Leu Leu Gln Pro Ile Ile Glu Gly Glu Thr Ala Ser Phe Phe Lys Glu
865                 870                 875                 880

Ile Lys Glu Glu Glu Glu Gly Ser Glu Asp Asp Ser Asn Val Lys Pro
                885                 890                 895

Asp Phe Met Val Thr Leu Lys Thr Asp Phe Ser Ala Arg Cys Phe Leu
            900                 905                 910

Asp Gln Phe Glu Asp Asp Ala Asp Gly Phe Ile Ser Pro Met Asp Asp
        915                 920                 925

Lys Ile Pro Ser Lys Cys Ser Gln Asp Thr Gly Leu Ser Asn Leu His
    930                 935                 940

Ala Ala Ser Ile Pro Glu Leu Leu Glu His Leu Gln Glu Met Arg Glu
945                 950                 955                 960

Glu Lys Lys Arg Ile Arg Lys Lys Leu Arg Asp Phe Glu Asp Asn Phe
                965                 970                 975

Phe Arg Gln Asn Gly Arg Asn Val Gln Lys Glu Asp Arg Thr Pro Met
            980                 985                 990

Ala Glu Glu Tyr Ser Glu Tyr Lys His Ile Lys Ala Lys Leu Arg Leu
        995                 1000                1005

Leu Glu Val Leu Ile Ser Lys Arg Asp Thr Asp Ser Lys Ser Met
    1010                1015                1020

<210> SEQ ID NO 57
<211> LENGTH: 3683
<212> TYPE: DNA
<213> ORGANISM: Artificial Sequence
<220> FEATURE:
<223> OTHER INFORMATION: IMPACT

<400> SEQUENCE: 57
cctggcaggc ggcggctgca gggcaggtcc aggggccaca tggctgaggg ggacgcaggg      60
agcgaccaga ggcagaatga ggaaattgaa gcaatggcag ccatttatgg cgaggagtgg     120
tgtgtcattg atgactgtgc caaaatattt tgtattagaa ttagcgacga tatagatgac     180

```
cccaaatgga cactttgctt gcaggtgatg ctgccgaatg aatacccagg tacagctcca    240 ccctatctacc agttgaatgc tccttggctt aaagggcaag aacgtgcgga tttatcaaat    300
agccttgagg aaatatatat tcagaatatc ggtgaaagta ttctttacct gtgggtggag    360
aaaataagag atgttcttat acaaaaatct cagatgacag aaccaggccc agatgtaaag    420
aagaaaactg aagaggaaga tgttgaatgt gaagatgatc tcattttagc atgtcagccg    480
gaaagttcgg ttaaagcatt ggattttgat atcagtgaaa ctcggacaga agtagaagta    540
gaagaattac ctccgattga tcatggcatt cctattacag accgaagaag tacttttcag    600
gcacacttgg ctccagtggt ttgtcccaaa caggtgaaaa tggttctttc caaattgtat    660
gagaataaga aaatagctag tgccacccac aacatctatg cctacagaat atattgtgag    720
gataaacaga ccttcttaca ggattgtgag gatgatgggg aaacagcagc tggtgggcgt    780
cttcttcatc tcatggagat tttgaatgtg aagaatgtca tggtggtagt atcacgctgg    840
tatggaggga ttctgctagg accagatcgc tttaaacata tcaacaactg tgccagaaac    900
atactagtgg aaaagaacta cacaaattca cctgaggagt catctaaggc tttgggaaag    960
aacaaaaaag taagaaaaga caagaagagg aatgaacatt aatacctgaa actataggaa    1020
aggttaattt gcctataatt atatatacat tccatagtca tcaaggaata tattgtgcag    1080
agagagtatc cttgactgct taagtcagcc agttcagcat ggataccaac attagctttt    1140
cttcttggtt atatcatctg ccaaaaatag agaacttatg atctattcat gtgtgtttca    1200
ggcttatttg ggagaactaa tttgaactta atcaccactt catctaattt tagcaaggta    1260
acagttgccc agggcagtac ctgaattaac tgtccatttc agtacatgtc aagtgccttt    1320
gttaggtgga gaagaaatgt ctctagagga atataaatac ctgatttctt gtcatcgaga    1380
ttcttgtact gttaaatgaa tattgccttt tactgctctt tatggcttat tggaatagga    1440
gctcatttaa gattgatctt ggagagtttc ttccttgtgat tttagttcat aagtatgtca    1500
cctttcattt tatagtgttc atcattgagt aatggattaa gtgaaaatcc aggagtatcc    1560
atctgcagtt atgtgctgag gtgataattc atccaacata tttgttagca taaatattat    1620
gcttcagttt ctgttgcaaa ttggtgattg tgaaattaca gaaagtgatt ttctagtctg    1680 cttttttgt ttaattcttg taatgtaagc aataaatatg gagtgtcagt agtctccttc    1740 cacccccagaa atgtgttggt gtaacattct cgtttctttt aacaacctgg aagtacctt    1800 cttgtgatct tcactgagga attagaacta tgatagaagt taggctgtgg caaatgggac    1860
attcgtagag tgggatagag gtggcagaat gaacctggtg tagggcagga gtatgttgtg    1920
tagttacatc aatttgatgc atgctttcca tctgcactcc agacggcttt ctcagttcca    1980
agattttgca gagagaagga gcaaaccttt tcattggaaa aacagaaaca accctccccc    2040 ccatttttc ccctctattc atcaaaacctt tatgtatctt tcatcttcca gttacctcta    2100
ggcatttaga tagtgaaatt tacctttgag atataacaat aagtgattaa ctgttcactt    2160
tcagatgtaa tggcaaacaa ttgttaaaag ttattaactg atcacagatt tgcctggact    2220
tcccttccca gggagggaac agaagttagg aggcaacttt gggatggtgc tagagcatgg    2280
aaagcacaga gaattggaca aacaggtctt tttctctttt ctctgatgtt ttaccttaa    2340 aagatccaac atccttaccg ttggtatttt tagtaaggtt atagtaaata gctttacacc    2400
aggatggatt ctgaaatata aattctaaat tatatttgtt ataactatat tttatgttgt    2460
atgttatcag gagccatcag agaatgacct ttttgtgttt ggaacacttg gttccatgaa    2520
aagtatgctt tgtgtttta ctgttaaaat aatttaaaaa ttaattattt tacataatta    2580
```

```
aagaagttaa aaactattaa cattaaataa tttcacaatt tcaacatgtc aaacctatga    2640
agggagatag gaaacaatga gaaacttact tttgctcctt tatacagaat tattaactat    2700
attttactaa ctaaaaaact ctagtattct ttacctaaag tcaattggct ggtaagaggg    2760
agagatgcaa aattctccag ctctgaactt ggagctactt cacactctac tcttaatgga    2820
aacttgaact aatgatagat agtattttt tcctctattt aaaattttg tcttgattag      2880 gagattttc agttctccat ataataattt tctacaatca gatctatgct gtggcatatt    2940
ttgctttatt taaaaatttt tttttagaga tgagttcttg ctctgtcacc taggctggag    3000
tgcagtggca tgatcatggc tcactgcagc cttgaccttc cagcctgcca agtagctggg    3060
attacagaca ggcatgtgct attacacctg gctaatttt aaagttttt ttgtaaagat      3120 agggtcttc tatgttgccc aggctcgtct tgagctcctg gcctcaatcg atcttcctgc    3180 caaggtttg gaattacagg tgtgagccac catgcctggc ctgctttgac atattttata    3240
gtgtgttaat tacaaatagt cttcatatgc cagaatataa gagcaagtgt tatctacttt    3300
ttagatggga attgcagaag ctgcatcaaa agtatgcttt gaggtatata tagtgaaaca    3360
gagcctttct gaagagaatt atatcaaact aattacaacc aagaaataat agtatgaagc    3420
ggatgctgtt tggaggacag gaaaatttat cgggaaaatt acataatccc tctgattcca    3480
ctatccagag atagccatta ttattaatat ttggtatgta catccttata ttatttttt     3540 tttatgcatg attttgtata tatggttatt tttctttcca taaaaatggt attaaactgt    3600
atatactgtt ttgtagccta catatttcat atagaagtat attgttaaca ttttccatgt    3660
caataaatat tctatggctt tct                                            3683
```

<210> SEQ ID NO 58
<211> LENGTH: 320
<212> TYPE: PRT
<213> ORGANISM: Artificial Sequence
<220> FEATURE:
<223> OTHER INFORMATION: IMPACT

<400> SEQUENCE: 58

```
Met Ala Glu Gly Asp Ala Gly Ser Asp Gln Arg Gln Asn Glu Glu Ile
1               5                   10                  15

Glu Ala Met Ala Ala Ile Tyr Gly Glu Glu Trp Cys Val Ile Asp Asp
            20                  25                  30

Cys Ala Lys Ile Phe Cys Ile Arg Ile Ser Asp Asp Ile Asp Asp Pro
        35                  40                  45

Lys Trp Thr Leu Cys Leu Gln Val Met Leu Pro Asn Glu Tyr Pro Gly
    50                  55                  60

Thr Ala Pro Pro Ile Tyr Gln Leu Asn Ala Pro Trp Leu Lys Gly Gln
65                  70                  75                  80

Glu Arg Ala Asp Leu Ser Asn Ser Leu Glu Glu Ile Tyr Ile Gln Asn
                85                  90                  95

Ile Gly Glu Ser Ile Leu Tyr Leu Trp Val Glu Lys Ile Arg Asp Val
            100                 105                 110

Leu Ile Gln Lys Ser Gln Met Thr Glu Pro Gly Pro Asp Val Lys Lys
        115                 120                 125

Lys Thr Glu Glu Glu Asp Val Glu Cys Glu Asp Leu Ile Leu Ala
    130                 135                 140

Cys Gln Pro Glu Ser Ser Val Lys Ala Leu Asp Phe Asp Ile Ser Glu
145                 150                 155                 160

Thr Arg Thr Glu Val Glu Val Glu Glu Leu Pro Pro Ile Asp His Gly
```

```
                    165                 170                 175
Ile Pro Ile Thr Asp Arg Arg Ser Thr Phe Gln Ala His Leu Ala Pro
            180                 185                 190

Val Val Cys Pro Lys Gln Val Lys Met Val Leu Ser Lys Leu Tyr Glu
            195                 200                 205

Asn Lys Lys Ile Ala Ser Ala Thr His Asn Ile Tyr Ala Tyr Arg Ile
            210                 215                 220

Tyr Cys Glu Asp Lys Gln Thr Phe Leu Gln Asp Cys Glu Asp Asp Gly
225                 230                 235                 240

Glu Thr Ala Ala Gly Gly Arg Leu Leu His Leu Met Glu Ile Leu Asn
            245                 250                 255

Val Lys Asn Val Met Val Val Ser Arg Trp Tyr Gly Gly Ile Leu
            260                 265                 270

Leu Gly Pro Asp Arg Phe Lys His Ile Asn Asn Cys Ala Arg Asn Ile
            275                 280                 285

Leu Val Glu Lys Asn Tyr Thr Asn Ser Pro Glu Ser Ser Lys Ala
            290                 295                 300

Leu Gly Lys Asn Lys Lys Val Arg Lys Asp Lys Lys Arg Asn Glu His
305                 310                 315                 320

<210> SEQ ID NO 59
<211> LENGTH: 6737
<212> TYPE: DNA
<213> ORGANISM: Artificial Sequence
<220> FEATURE:
<223> OTHER INFORMATION: KIAA1128

<400> SEQUENCE: 59
gctgtggatc ttacaaagcc ttatcagaac caacagctat ccattagagt gcctctacgg      60
tcaagtatgc taacaagaaa ttcccggcag ccagaagtac tcaatgggaa tgaacatttg     120
gggtatggat ttaataggcc ttatgctgct ggtggaaaga agttggcttt accaaatggc     180
ccaggtgtaa cttctacttt aggttataga atggttcatc cctctctact gaaatctagc     240
cgatctccat tttctgggac tatgacagtt gatggaaata aaaattcacc tgctgacaca     300
tgtgtagagg aagatgctac agttttggct aaggacagag ctgctaataa ggaccaagaa     360
ctgattgaaa tgaaagtta tagaacaaaa acaaccaga ccatgaaaca tgatgctaaa      420
atgagatacc tgagtgatga tgtggatgac atttccttgt cgtctttgtc atcttctgat     480
aagaatgatt taagtgaaga ctttagtgat gattttatag atatagaaga ctccaacaga     540
actagaataa ctccagagga aatgtctctc aaagaagaga acatgaaaaa tgggccacca     600
caggatatgt tgattcccc caaggaaaat gaaaagcct tcagtaaaac tgatgaatgg      660
atagatataa gtgtctctga caggagtgaa tgtacaaaac atacttctgg gaataatttg     720
gtttcaccag atacagacta cagagctggt tcttcgtttg aactctctcc atctgatagc     780
tctgatggaa catacatgtg ggatgaagaa ggcttggaac ccattggaaa tgtccatcca     840
gttgggagct atgagtcctc tgaaatgaac agcatagata ttttgaataa tcttgaatca     900
tgtgaccttg aggatgatga tcttatgctt gatgtggatc tgcctgagga tgcacctctt     960
gaaaatgtgg agtgtgacaa tatgaaccgc tttgaccgac agacagaaa tgttcggcag    1020 cctcaggaag gttttggaa aaggccaccc cagaggtgga gtggacagga gcattaccac    1080
ctcagccacc ctgaccacta tcatcaccat ggaaaaagtg acttgagcag aggctctccc    1140
tatagagaat ctcctttggg tcattttgaa agctatggag gatgccctt tttccaggct    1200 cagaagatgt tgttgatgt accagaaaat acagtgatac tggatgagat gacccttcgg    1260
```

```
cacatggttc aggattgcac tgctgtaaaa actcagttac tcaaactgaa acgtctcctg    1320
catcagcatg atggaagtgg ttcattgcat gatattcaac tgtcattgcc atccagtcca    1380
gaaccagaag atggtgataa agtatataag aatgaagatt tattaaatga aataaaacaa    1440
cttaaagacg aaataaagaa aaaagatgaa aagatccaac tattagaact tcagcttgca    1500
actcagcata tctgccacca aaaatgtaaa gaggaaaaat gcacttatgc tgataaaatat   1560 acccaaacac cctggagacg aattcctggt gggtattctg ctccctcctt ctctccttgg    1620
cagggctcct tccaggggat cccacggact gttccaccgc accgcagaca gacctcaagt    1680
actacagcct tcccagcagcc ttcccagacc cacagatcac acccagggaa aactaataaa   1740
gccacaacgt atcgaggccc gcagtgaatg ctcaatccaa gacatgcatc agggcggtgc    1800
acatccggaa gaaagcttta cacacgtctt gcaccaagaa agcaactatg gtttggaaga    1860
gcagcctttt tcatcaggcc acaattaac aatggatgtg ctaagagta cccttctga    1920 agcaaactta aacattactg taaatgctca agagccttat catttggcaa acaatcaaat    1980
tagtgacatg cagtttatac ccacttctct tcagacacct cccgagtcaa gtacagtaga    2040
ccaggctaag agagttggaa gaaatcagtc tccgccagtg ggttatatgt ctcagcccaa    2100
gtccttgcag cttttaaagc catccatatt gagttctttg gtaccgcctc cagtttctga    2160
atcatctcca gtaggactc ccacttgtaa aaagtcacca ataatcacaa catgtaattc      2220
agcaaaactt cagccaacat ctagtcaaac aaatcttgca ataatcaga atctgaaagc     2280 atctaagctc cgccccccct caggctcttt caaacaaaaa caaacaaaca gcccccaact    2340
agagcctcaa agcttccagg ccaagacaag catcccaagg ccactaacac aacgaaaaga    2400
aatcatgcag aatccaaatg gcaatttgca ttctggggat tgtttggcct ctaatcgata    2460
ttctcgtctt cctaaaccaa agatacatta agtacatagc catcacctgc caatttgttt    2520
cttaaaaaca atctcttctg taatagcttt atgtgcagct tgcagcttgc tactgtggtg    2580
gaggttccat tgaaagcctg caaatcttaa attaaaatgt ggaagcttct actagtttgg    2640
ctccttcatt ttatatcctg gttgaagtac atgccatttg agcataatta tctcaggtaa    2700
acacgaaagt ttgcttaccc atttcagagg cctgccaaag gcccaaatca tgttatccat    2760
ccctctccag gtcagaaaat tcataatatt ttactgagca ggcaagaagt gtgctttgct    2820
ggtttagtcc tattaaggtc tgtatttatt gtggttgtca gaacctcacc ccttttcact    2880
tgtctctcct gtgaatatgg ctactatttt aactaaagat atggtgataa tggaagatgg    2940
tagtctgtaa gcagagttct ggccagtgtt ttgtatattt aaaaggtcta tgcaaaagct    3000
ttgtgatgaa taaggagat taggctttta atggaaagtc tatgtaagtt ttatttttcc     3060
ttgccagggt cagtcagcta atgttactgt tgattcattt cccaaattcc ccagactgaa    3120
aatgtttctt attacatata aatcagttat atattccttt acatcttgtt ttacaaacac    3180
atgtgcatgc acacacacac atacacacac ataccattta tgtttgtatt tgttactggg   3240
taaattttgg agcgcttgag atacaccttg aaacctgtac ctaaagatgt attcatttgt    3300
aacatatgtt ggtgctagag ttttgctggt aattcaggtt tgaacccta ggcttgtgga    3360 tccatgatag ccattttaag gttccacagc attatgtctt taattgtaat atttatattt    3420
attgattttc tgctaatatc tgaagactga aataatgaac ttgaaacatt tgcacaaaac    3480
tttgatgggg tataaatata ccatatatag ggattgtaaa ctattttcta tagcaaaaca    3540
agttaaaata ttttgagaaa aataacaaat ttaaataaga ctatcttgag aaagctggag    3600
ttcataatat tctccccctc ccccatctcc agtctcctag gtttccttt tctgtgtttt    3660
```

```
ttgttttttt ctgtttgttt tttgagacag agtcttgctc cattgcccag gctggattac    3720
agtggcgcaa tctcggctca ctgcaacttc tgcctcccgg gttcaagcga ttctcctgcc    3780
tcagcctcct gagtagctgg gactacaggc atgtgccacc atgcctggct aattttttg    3840
tattttagt agagatgagg tttcaccttg ttggtcaggc tggtctcgaa ctcctgacct     3900
caagtgatcc acccacctcg tctatggtgt attttgaaa gacaattttt taaaggtaga    3960
tttgggaaaa aatagaatt gaagatggga aattttgttt tattaaaaag gtgctagaag     4020
atgtttcaaa gacaatattc ttattttaat acgctgtaga aggtaggtgt ggaacctcca   4080
tgctaccatg tgcacaaacc taattatgct ttgggtcact tgtcagttca gtaaatctgc   4140
cttcctcttc tcccaaatca tgtcatcttt aggttgttca cctgcagctg ctttaaatga   4200
attagtatct ttcagataga taaccttaca aggagaatgt tgttttgag cagctgacca    4260
aaaatatatc aaacaggatt atggccaaaa agtcactcaa atttctagag attccttaa    4320
aagatgtatg ttgatgaaat tgccccttta taagaaaaac aacagcaagt cttttagtag   4380
aaatttgaaa gaagtgtttg ctaccatttt gacccattat tcccttacct atcagatgaa   4440
tttgccattc actggataga aaccattctt ggatttggta agaggtgagc aagacaaatc   4500
ttgtaccata ctcttatgta ccagcacttc tgatggagaa gcagtgaagt tcagaacgtt   4560
cttcacatag tccagatact gttagagtca ggcaaatcag caaagcactt tgttatggag   4620
atgacccatg atggctgcag ttgtaagtgg gcatacatgt tctatcattt tgaaggagaa   4680
agaaaaccgt tctcacatgt cgcaaatatg tgaatcatac tatattcccc taagtaaaa   4740
ccagtgactt agtggttttt ggtttattta gaagttggtt tagaccctta tgaaacatta   4800
tttacgagtt ggccttatcc ttaagggaaa agttctaaat ttttaaattt atttttaatt   4860
ccctagtctg agggaaatgt ctttattgtc cattacataa aaatgttgac tccagtaatt   4920
tatttttctc tattttttcc tccatgtatt tactccattt ttctctattt tttccttccc   4980
tgatggattt gcagaaatgt taaccaatta gctcaacttt tctctacctt tgttgagtct   5040
taatctttta gaagataggc ttaccgtata tttatgaagc ataatatatt aaaagaaaac   5100
aaatctagga tgcttgcatg acataaagta tttgcctgca gttttcatta aaaactgcaa   5160
gaatatcatg cttgtctgct tcttagtaaa tgttaagtct gaaatggaag tgaggatgta   5220
actctactga ataatcaaag atcatcttag atttggcttg atctgtgttt attgcttcta   5280
ttaatgtaaa tcaactctgt gccaaatcct cctccacaaa ccatttattg tcttagttct   5340
agtggtatca atgaagatag ttacagtata tgaattctaa gtcctgagga agaaatttta   5400
tggggtttgt taagtttcac attcgtgaaa gaggaaatta gtagagtatt cagactttga   5460
tatttggctg ttaatgggat gcatatcaaa ttttaaaag aaggcttggc ctaaggagtt   5520
tattggtaca ggtgcagatg attttaaggc attaaaggat tatagagtta tgtcattag    5580
actgtttcta ataactgaga ccatctaaca tttttctttt ggagtctcat ttttatttgt   5640
gcaatatttt caggcatata ggctactgtt cattgtattt atatatat tagaatttac    5700
taagtacttt aacaagtaaa aatctgaata tgaaagaaaa tatcagattt gcactttaaa   5760
tgagcttaat tgcttgaagt tgtgcctgaa atatcgaatt gcctcctatt gggtgtggct   5820
ttgttgaaat aaatttgtaa ttgttgctgt ttgaagatat cagtacagct gttcacagaa   5880
atatattccc agcatgtcac ttttccatta aagcactaag ttttctttga atgttccatt   5940
gttccgataa gtatttact ttttctcag tacatcagag agagcgtgat cccctacag     6000
ctgtcacttc caaatgttcc tgtagcataa atggtgttac agacactgag gtgcactctt   6060
```

```
ggtttctgag cagagttgtc atactggttt cctggtctct agggcactgg ggatgtactt   6120
tgaaatcacc gaacaggctt gcaattaaga tcaataaggc tgcagcacca tttcaattta   6180
ctttccatct tacccagtag tttttgtgtt tttaaattcg tttgggtggt tatgtttgca   6240
tgcttaagca cacatttgaa aattaattat agctgtacta cccgatgttt ttccttgggg   6300
atgatggcct tgttcctttt taaattctga tgcttgaatt ctattttcta gtgatttttc   6360
acatctccct ttaagttttt gctgcagcaa tttgagagag tacttttgat taaatgattc   6420
tgatggtggg caccaatcta caactatgtc attaactgaa gatacatgtt ttaatcttgt   6480
tgggaataag cttacccact ttctccttgg taaagcgttt acttaacaaa ataatacccg   6540
agaatgtaag gtctctaagt cattactaac aaagagcaaa aataatatct gcagtattgt   6600
ttttcccatt gattttaagt cagtttagag tacaaactgt atattagaat ttgcctgtaa   6660
aatgaattct aaaaagcaga tgtaaagtct ctcctgaaaa tgttggcata gtaaataaaa   6720
ataaagttca taattat                                                  6737

<210> SEQ ID NO 60
<211> LENGTH: 588
<212> TYPE: PRT
<213> ORGANISM: Artificial Sequence
<220> FEATURE:
<223> OTHER INFORMATION: KIAA1128

<400> SEQUENCE: 60

Ala Val Asp Leu Thr Lys Pro Tyr Gln Asn Gln Gln Leu Ser Ile Arg
 1               5                  10                  15

Val Pro Leu Arg Ser Ser Met Leu Thr Arg Asn Ser Arg Gln Pro Glu
            20                  25                  30

Val Leu Asn Gly Asn Glu His Leu Gly Tyr Gly Phe Asn Arg Pro Tyr
        35                  40                  45

Ala Ala Gly Gly Lys Lys Leu Ala Leu Pro Asn Gly Pro Gly Val Thr
    50                  55                  60

Ser Thr Leu Gly Tyr Arg Met Val His Pro Ser Leu Leu Lys Ser Ser
65                  70                  75                  80

Arg Ser Pro Phe Ser Gly Thr Met Thr Val Asp Gly Asn Lys Asn Ser
                85                  90                  95

Pro Ala Asp Thr Cys Val Glu Glu Asp Ala Thr Val Leu Ala Lys Asp
            100                 105                 110

Arg Ala Ala Asn Lys Asp Gln Glu Leu Ile Glu Asn Glu Ser Tyr Arg
        115                 120                 125

Thr Lys Asn Asn Gln Thr Met Lys His Asp Ala Lys Met Arg Tyr Leu
    130                 135                 140

Ser Asp Asp Val Asp Asp Ile Ser Leu Ser Ser Leu Ser Ser Ser Asp
145                 150                 155                 160

Lys Asn Asp Leu Ser Glu Asp Phe Ser Asp Asp Phe Ile Asp Ile Glu
                165                 170                 175

Asp Ser Asn Arg Thr Arg Ile Thr Pro Glu Glu Met Ser Leu Lys Glu
            180                 185                 190

Glu Lys His Glu Asn Gly Pro Pro Gln Asp Met Phe Asp Ser Pro Lys
        195                 200                 205

Glu Asn Glu Lys Ala Phe Ser Lys Thr Asp Glu Trp Ile Asp Ile Ser
    210                 215                 220

Val Ser Asp Arg Ser Glu Cys Thr Lys His Thr Ser Gly Asn Asn Leu
225                 230                 235                 240
```

-continued

```
Val Ser Pro Asp Thr Asp Tyr Arg Ala Gly Ser Ser Phe Glu Leu Ser
            245             250             255

Pro Ser Asp Ser Ser Asp Gly Thr Tyr Met Trp Asp Glu Glu Gly Leu
        260             265             270

Glu Pro Ile Gly Asn Val His Pro Val Gly Ser Tyr Glu Ser Ser Glu
        275             280             285

Met Asn Ser Ile Asp Ile Leu Asn Asn Leu Glu Ser Cys Asp Leu Glu
    290             295             300

Asp Asp Asp Leu Met Leu Asp Val Asp Leu Pro Glu Asp Ala Pro Leu
305             310             315             320

Glu Asn Val Glu Cys Asp Asn Met Asn Arg Phe Asp Arg Pro Asp Arg
            325             330             335

Asn Val Arg Gln Pro Gln Glu Gly Phe Trp Lys Arg Pro Pro Gln Arg
            340             345             350

Trp Ser Gly Gln Glu His Tyr His Leu Ser His Pro Asp His Tyr His
        355             360             365

His His Gly Lys Ser Asp Leu Ser Arg Gly Ser Pro Tyr Arg Glu Ser
        370             375             380

Pro Leu Gly His Phe Glu Ser Tyr Gly Gly Met Pro Phe Phe Gln Ala
385             390             395             400

Gln Lys Met Phe Val Asp Val Pro Glu Asn Thr Val Ile Leu Asp Glu
            405             410             415

Met Thr Leu Arg His Met Val Gln Asp Cys Thr Ala Val Lys Thr Gln
            420             425             430

Leu Leu Lys Leu Lys Arg Leu Leu His Gln His Asp Gly Ser Gly Ser
        435             440             445

Leu His Asp Ile Gln Leu Ser Leu Pro Ser Ser Pro Glu Pro Glu Asp
    450             455             460

Gly Asp Lys Val Tyr Lys Asn Glu Asp Leu Leu Asn Glu Ile Lys Gln
465             470             475             480

Leu Lys Asp Glu Ile Lys Lys Lys Asp Glu Lys Ile Gln Leu Leu Glu
            485             490             495

Leu Gln Leu Ala Thr Gln His Ile Cys His Gln Lys Cys Lys Glu Glu
        500             505             510

Lys Cys Thr Tyr Ala Asp Lys Tyr Thr Gln Thr Pro Trp Arg Arg Ile
        515             520             525

Pro Gly Gly Tyr Ser Ala Pro Ser Phe Ser Pro Trp Gln Gly Ser Phe
    530             535             540

Gln Gly Ile Pro Arg Thr Val Pro Pro His Arg Arg Gln Thr Ser Ser
545             550             555             560

Thr Thr Ala Phe Gln Gln Pro Ser Gln Thr His Arg Ser His Pro Gly
            565             570             575

Lys Thr Asn Lys Ala Thr Thr Tyr Arg Gly Pro Gln
            580             585
```

DIAGNOSTIC TOOL FOR DIAGNOSING BENIGN VERSUS MALIGNANT THYROID LESIONS

This application claims priority to U.S. Provisional Application Ser. No. 60/560,900 filed Apr. 9, 2004 and to U.S. Provisional Application Ser. No. 60/622,643 filed Oct. 26, 2004, both of which are herein incorporated in their entireties by this reference.

FIELD OF THE INVENTION

The present invention relates to the use of genes differentially expressed in benign thyroid lesions and malignant thyroid lesions for the diagnosis and staging of thyroid cancer.

BACKGROUND OF THE INVENTION

It is well known that cancer results from changes in gene expression patterns that are important for cellular regulatory processes such as growth, differentiation, DNA duplication, mismatch repair and apoptosis. It is also becoming more apparent that effective treatment and diagnosis of cancer is dependent upon an understanding of these important processes. Classification of human cancers into distinct groups based on their origin and histopathological appearance has historically been the foundation for diagnosis and treatment. This classification is generally based on cellular architecture, certain unique cellular characteristics and cell-specific antigens only. In contrast, gene expression assays have the potential to identify thousands of unique characteristics for each tumor type (3) (4). Elucidating a genome wide expression pattern for disease states not only could have a enormous impact on the understanding of specific cell biology, but could also provide the necessary link between molecular genetics and clinical medicine (5) (6) (7).

Thyroid carcinoma represents 1% of all malignant diseases, but 90% of all neuroendocrine malignancies. It is estimated that 5-10% of the population will develop a clinically significant thyroid nodule during their life-time (8). The best available test in the evaluation of a patient with a thyroid nodule is fine needle aspiration biopsy (FNA) (9). Of the malignant FNAs, the majority are from papillary thyroid cancers (PTC) or its follicular variant (FVPTC). These can be easily diagnosed if they have the classic cytologic features including abundant cellularity and enlarged nuclei containing intra-nuclear grooves and inclusions (10). Indeed, one third of the time these diagnoses are clear on FNA. Fine needle aspiration biopsy of thyroid nodules has greatly reduced the need for thyroid surgery and has increased the percentage of malignant tumors among excised nodules (11, 12). In addition, the diagnosis of malignant thyroid tumors, combined with effective therapy, has lead to a marked decrease in morbidity due to thyroid cancer. Unfortunately, many thyroid FNAs are not definitively benign or malignant, yielding an "indeterminate" or "suspicious" diagnosis. The prevalence of indeterminate FNAs varies, but typically ranges from 10-25% of FNAs (13-15). In general, thyroid FNAs are indeterminate due to overlapping or undefined morphologic criteria for benign versus malignant lesions, or focal nuclear atypia within otherwise benign specimens. Of note, twice as many patients are referred for surgery for a suspicious lesion (10%) than for a malignant lesion (5%), an occurrence that is not widely appreciated since the majority of FNAs are benign. Therefore when the diagnosis is unclear on FNA these patients are classified as having a suspicious or indeterminate lesion only. It is well known that frozen section analysis often yields no additional information.

The question then arises: "Should the surgeon perform a thyroid lobectomy, which is appropriate for benign lesions or a total thyroidectomy, which is appropriate for malignant lesions when the diagnosis is uncertain both preoperatively and intra-operatively?" Thyroid lobectomy as the initial procedure for every patient with a suspicious FNA could result in the patient with cancer having to undergo a second operation for completion thyroidectomy. Conversely, total thyroidectomy for all patients with suspicious FNA would result in a majority of patients undergoing an unnecessary surgical procedure, requiring lifelong thyroid hormone replacement and exposure to the inherent risks of surgery (16).

Several attempts to formulate a consensus about classification and treatment of thyroid carcinoma based on standard histopathologic analysis have resulted in published guidelines for diagnosis and initial disease management (2). In the past few decades no improvement has been made in the differential diagnosis of thyroid tumors by fine needle aspiration biopsy (FNA), specifically suspicious or indeterminate thyroid lesions, suggesting that a new approach to this should be explored. Thus, there is a compelling need to develop more accurate initial diagnostic tests for evaluating a thyroid nodule.

SUMMARY OF THE INVENTION

This invention is based in part on the discovery of genes whose expression levels can be correlated to benign or malignant states in a thyroid cell. Thus, the present invention provides differentially expressed genes that can be utilized to diagnose, stage and treat thyroid cancer. These differentially expressed genes are collectively referred to herein as "Differentially Expressed Thyroid" genes ("DET" genes). Examples of these DET genes are provided herein and include C21orf4 (DET1), Hs.145049 (DET2), Hs.296031 (DET3), KIT (DET4), LSM7 (DET5), SYNGR2 (DET6), C11orf8 (DET7), CDH1 (DET8), FAM13A1 (DET9), IMPACT (DET10) and KIAA1128 (DET11).

The present invention provides a gene expression approach to diagnose benign vs malignant thyroid lesions. Identification of differentially expressed genes allows the development of models that can differentiate benign vs. malignant thyroid tumors. Results obtained from these models provide a molecular classification system for thyroid tumors and this in turn provides a more accurate diagnostic tool for the clinician managing patients with suspicious thyroid lesions.

The present invention also provides a method for classifying a thyroid lesion in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby classifying the thyroid lesion in the subject.

Further provided is a method for classifying a thyroid lesion in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5 and DET6, in the test cell population and reference cell population, thereby classifying the thyroid lesion in the subject.

The present invention also provides a method of identifying the stage of a thyroid tumor in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby identifying the stage of the thyroid tumor in the subject.

Further provided by the present invention is a method of identifying the stage of a thyroid tumor in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby identifying the stage of the thyroid tumor in the subject.

Also provided by the present invention is a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET5 and DET6, with a test agent; b) measuring the expression of one or more nucleic acid sequences selected from the group consisting of DET1, DET2, DET3, DET4, DET5 and DET6 in the population; c) comparing the expression of the nucleic acid sequence(s) to the expression of the nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5 and DET6, in the test cell population and reference cell population, such that if there is a difference corresponding to an improvement, a therapeutic agent for treating a thyroid tumor has been identified.

The present invention also provides a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET6, DET7, DET8, DET9, DET10 and DET11, with a test agent; b) measuring the expression of one or more nucleic acid sequences selected from the group consisting of DET1, DET2, DET3, DET4, DET6, DET7, DET8, DET9, DET10 and DET11 in the population; c) comparing the expression of the nucleic acid sequence(s) to the expression of the nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, such that if there is a difference corresponding to an improvement, a therapeutic agent for treating a thyroid tumor has been identified.

Also provided by the present invention is a kit comprising one or more reagents for detecting the expression of one or more nucleic acid(s) selected from the group consisting of DET1, DET2, DET3, DET4, DET5, DET6, DET7, DET8, DET9, DET10, DET11.

BRIEF DESCRIPTION OF THE FIGURES

FIG. 6 shows immunohistochemical results for expression of KIT and CDH1 in malignant and benign thyroid lesions. These results correlate with the expression data obtained via microarray and RT-PCR.

DIFFERENTIALLY EXPRESSED THYROID GENES

Figure 1:
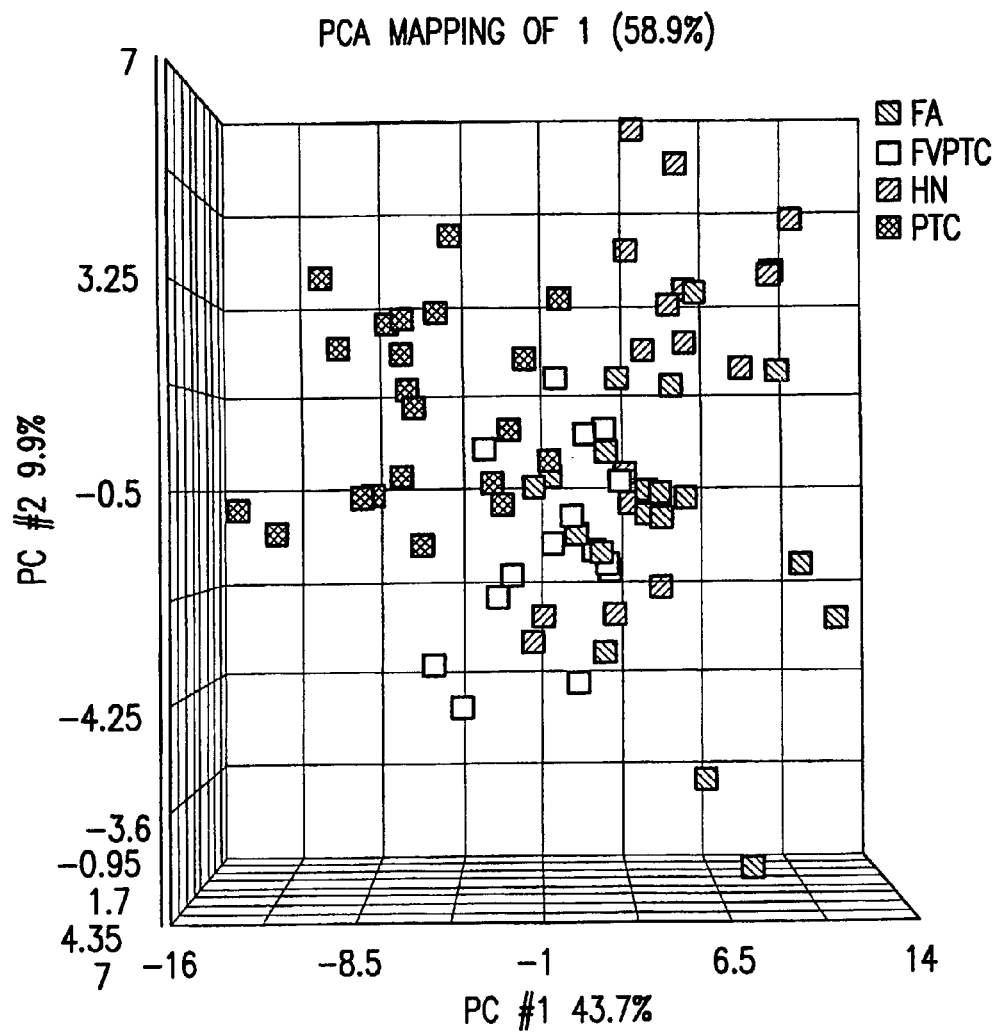
FIG. 1 shows PCA (principle component analysis) organization in a three-dimensional space of all samples divided into four groups: hyperplastic-nodule (HN), follicular adenoma (FA), follicular variant of papillary thyroid carcinoma (FVPTC) and papillary thyroid carcinoma (PTC). Each dot represents how that sample is localized in space on the basis of its gene expression profile. The distance between any pair of points is related to the similarity between the two observations in high dimensional space. The principal components are plotted along the various axes (x,y,z). The % indicates the total amount of variance captured by the PCs; the first PC is the one capturing the largest amount of variance, or information, the second PC, the second largest etc. Three PCs were plotted, thus creating a 3D plot.

One aspect of the invention relates to genes that are differentially expressed in benign and/or malignant thyroid lesions relative to normal thyroid tissue. These differentially expressed genes are collectively referred to herein as "Differentially Expressed Thyroid" genes ("DET" genes). The corresponding gene products are referred to as "DET products" "DET polypeptides" and/or "DET proteins". The DET genes of the present invention include C21orf4, Hs.145049, Hs.296031, KIT, LSM7, SYNGR2, C11orf8, CDH1, FAM13A1, IMPACT and KIAA1128. The following provides a brief description of each DET gene provided herein.

C21orf4 (DET1)

C21orf4 is a gene encoding an integral membrane protein of unknown function, located in the q region of chromosome 21. C21orf4 was found to be upregulated in benign thyroid lesions and upregulated in malignant thyroid lesions as compared to normal thyroid tissue. Upon comparing benign tissue with malignant tissue, C21orf4 was found to be upregulated in benign tissue as compared to malignant tissue. An example of a nucleic acid encoding C21orf4 is set forth herein as SEQ ID NO: 40. Nucleic acid sequences for C21orf4 can also be accessed via GenBank Accession No. AP001717, GenBank Accession No. NM_006134 and via Unigene No. Hs.433668. All of the information, including any nucleic acid and amino acids sequences provided for C21orf4 under GenBank Accession No. AP001717, GenBank Accession No. NM_006134 and Unigene No. Hs.433668 is hereby incorporated in its entirety by this reference.

Hs.145049 (DET2)

Hs. 145049, formerly known as Hs.24183, is a sodium-D-glucose transporter. The Unigene cluster identified as Unigene NO. Hs. 24183 has been retired and has been replaced by Hs. 145049. Hs. 145049 was found to be upregulated in both benign and malignant thyroid lesions as compared to normal thyroid tissue. Upon comparing benign tissue with malignant tissue, Hs.145049 was found to be upregulated in benign tissue as compared to malignant tissue. A nucleic acid encoding Hs. 145049 is set forth herein as SEQ ID NO: 42. Nucleic acid sequences for Hs.145049 can also be accessed via GenBank Accession No. NP_060265, via GenBank Accession No. AL832414.1 and via Unigene No. Hs.145049. All of the information, including any nucleic acid and amino acids sequences provided for Hs.145049 under GenBank Accession NP_060265, via GenBank Accession No. AL832414 and via Unigene No. Hs.145049 is hereby incorporated in its entirety by this reference.

Hs.296031 (DET3)

Hs.296031 is a gene of unknown function. Hs. 296031 was found to be downregulated in benign and comparable to normal in malignant thyroid lesions as compared to normal thyroid tissue. Upon comparing benign tissue with malignant tissue, Hs.296031 was found to be upregulated in malignant tissue as compared to benign tissue. A nucleic acid encoding Hs. 296031 is set forth herein as SEQ ID NO: 44. Nucleic acid sequences for Hs.296031 can also be accessed via GenBank Accession No. BC038512 and via Unigene No. Hs.296031. All of the information, including any nucleic acid and amino acids sequences provided for Hs.296031 under GenBank Accession No. BC038512 and Unigene No. Hs.296031 is hereby incorporated in its entirety by this reference.

c-kit Proto-Oncogene (KIT) (DET4)

KIT is a protooncogene that functions as a transmembrane receptor tyrosine kinase and is involved in cellular proliferation. See Yarden et al. "Human proto-oncogene c-kit: a new cell surface receptor tyrosine kinase for an unidentified ligand" *EMBO J.* 6(11): 3341-3351 (1987). The Yarden et al. reference is incorporated herein in its entirety for the purpose of describing KIT function as well as for incorporating all KIT protein sequences and nucleic acids encoding KIT provided in the Yarden et al. reference. KIT was found to be downregulated in benign thyroid lesions and downregulated in malignant thyroid lesions as compared to normal thyroid tissue. Upon comparing benign tissue with malignant tissue, KIT was found to be upregulated in benign tissue as compared to malignant tissue. Thus, KIT expression decreases during malignancy. A nucleic acid encoding KIT is set forth herein as SEQ ID NO: 45. Nucleic acid sequences for KIT can also be accessed via GenBank Accession Nos. X06182 and NM_000222 and via Unigene No. Hs.81665. All of the information, including any nucleic acid and amino acids sequences provided for KIT under GenBank Accession No. X06182, GenBank Accession No. NM_000222 and via Unigene No. Hs.81665 is hereby incorporated in its entirety by this reference.

U6 Small Nuclear RNA Associated *Homo sapiens* LSM7 Homolog (LSM7) (DET5)

LSM7 is a U6 small nuclear ribonucleoprotein that is involved in tRNA processing. LSM7 was found to be upregulated in benign thyroid lesions and downregulated in malignant thyroid lesions as compared to normal thyroid tissue. Upon comparing benign tissue with malignant tissue, LSM-7 was found to be upregulated in benign tissue as compared to malignant tissue. A nucleic acid sequence encoding LSM7 is set forth herein as SEQ ID NO: 47. Nucleic acid sequences for LSM7 can also be accessed via GenBank Accession No. NM_016199 and via Unigene No. Hs.512610. All of the information, including any nucleic acid and amino acids sequences provided for LSM7 under GenBank Accession No. NM_016199 and Unigene No. Hs.512610 is hereby incorporated in its entirety by this reference.

Synaptogyrin 2 (SYNGR2) (DET6)

SYNGR2 is a synaptic vesicle protein that may play a role in regulating membrane traffic. SYNGR2 was found to be downregulated in benign thyroid lesions and comparable to normal in malignant thyroid lesions as compared to normal thyroid tissue. Upon comparing benign tissue with malignant tissue, SYNGR2 was found to be upregulated in malignant tissue as compared to benign tissue. A nucleic acid encoding SYNG2 is set forth herein as SEQ ID NO: 49. Nucleic acid sequences for SYNGR2 can also be accessed via GenBank Accession No. NM_004710 and via Unigene No. Hs. 433753. All of the information, including any nucleic acid and amino acids sequences provided for LSM7 under GenBank Accession No. NM_004710 and via Unigene No. Hs. 433753 is hereby incorporated in its entirety by this reference.

C11orf8 (DET7)

C11orf8 is a gene involved in central nervous system development and function. C11orf8 was found to be downregulated in both benign thyroid lesions and malignant thyroid lesions as compared to normal thyroid tissue. Upon comparing benign tissue with malignant tissue, C11orf8 was found to be upregulated in benign tissue as compared to malignant tissue. A nucleic acid encoding C11orf8 is set forth herein as SEQ ID NO: 51. Nucleic acid sequences for C11orf8 can also be accessed via GenBank Accession No. NM_001584 and via Unigene No. Hs. 432000. All of the information, including any nucleic acid and amino acids sequences provided for LSM7 under GenBank Accession No. NM_001584 and Unigene No. Hs. 432000 is hereby incorporated in its entirety by this reference.

Cadherin 1, Type1, E-Cadherin (CDH1) (DET8)

CDH1 is a cadherin protein involved in cell adhesion, motility, growth and proliferation. CDH1 was found to be upregulated in benign thyroid lesions and downregulated in malignant thyroid lesions as compared to normal thyroid tissue. Upon comparing benign tissue with malignant tissue, CDH1 was found to be upregulated in benign tissue as compared to malignant tissue. A nucleic acid encoding CDH1 is set forth herein as SEQ ID NO: 53. Nucleic acid sequences for CDH1 can also be accessed via GenBank Accession No. NM_004360 and via Unigene No. Hs. 194657. All of the information, including any nucleic acid and amino acids sequences provided for CDH1 under GenBank Accession No. NM_004360 and Unigene No. Hs. 194657 is hereby incorporated in its entirety by this reference.

*Homo sapiens* Family with Sequence Similarity 13, Member A1 (FAM13A1) (DET9)

FAM13A1 is a gene of unknown function. FAM13A1 was found to be upregulated in benign thyroid lesions and downregulated in malignant thyroid lesions as compared to normal thyroid tissue. Upon comparing benign tissue with malignant tissue, FAM13A1 was found to be upregulated in benign tissue as compared to malignant tissue. A nucleic acid encoding FAM13A1 is set forth herein as SEQ ID NO: 55. Nucleic acid sequences for FAM13A1 can also be accessed via GenBank Accession No. NM_014883 and via Unigene No. Hs. 442818. All of the information, including any nucleic acid and amino acids sequences provided for FAM13A1 under GenBank Accession No. NM_014883 and Unigene No. Hs. 442818 is hereby incorporated in its entirety by this reference.

*Homo sapiens* Hypothetical Protein IMPACT (IMPACT) (DET10)

IMPACT is a gene of unknown function. IMPACT was found to be upregulated in benign thyroid lesions and downregulated in malignant thyroid lesions as compared to normal thyroid tissue. Upon comparing benign tissue with malignant tissue, IMPACT was found to be upregulated in benign tissue as compared to malignant tissue. A nucleic acid encoding IMPACT is set forth herein as SEQ ID NO: 57. Nucleic acid sequences for IMPACT can also be accessed via GenBank Accession No. NM_018439 and via Unigene No. Hs. 284245. All of the information, including any nucleic acid and amino acids sequences provided for IMPACT under GenBank Accession No. NM_018439 and Unigene No. Hs. 284245 is hereby incorporated in its entirety by this reference.

KIAA1128 Protein (KIAA1128) (DET11)

KIAA1128 is a gene of unknown function. KIAA1128 was found to be upregulated in benign thyroid lesions and downregulated in malignant thyroid lesions as compared to normal thyroid tissue. Upon comparing benign tissue with malignant tissue, KIAA1128 was found to be upregulated in benign tissue as compared to malignant tissue. A nucleic acid encoding KIAA1128 is set forth herein as SEQ ID NO: 59. Nucleic acid sequences for KIAA1128 can also be accessed via GenBank Accession Nos. AB032954 and via Unigene No. Hs. 81897. All of the information, including any nucleic acid and amino acids sequences provided for KIAA1128 under GenBank Accession Nos. AB032954 and via Unigene No. Hs. 81897 is hereby incorporated in its entirety by this reference.

Diagnostic Methods

The present invention provides a method for classifying a thyroid lesion in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby classifying the thyroid lesion in the subject.

The present invention also provides a method for classifying a thyroid lesion in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of the nucleic acid sequence(s) to the expression of the nucleic acid sequence(s) in a reference cell population comprising at least one cell for which a thyroid lesion classification is known; and c) identifying a difference, if present, in expression levels of one or more nucleic acid sequences selected from the group consisting of DET1, DET2, DET3, DET4, DET5 and DET6, in the test cell population and reference cell population, thereby classifying the thyroid lesion in the subject.

In the methods of the present invention, "classifying a thyroid lesion" is equivalent to diagnosing a subject with a type of thyroid lesion. These lesions can be benign or malignant. Examples of a benign lesion include, but are not limited to, follicular adenoma, hyperplastic nodule, papillary adenoma, thyroiditis nodule and multinodular goiter. Examples of malignant lesions include, but are not limited to, papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma.

In the methods of the present invention, measuring the expression levels of one or more nucleic acids sequences selected from the group consisting of DET1, DET2, DET3, DET4, DET6, DET7, DET8, DET9, DET10 and DET11, means that the expression of any combination of these sequences can be measured. For example, the expression level of one, two, three, four, five, six, seven, eight, nine or ten sequences selected from the group consisting of DET1, DET2, DET3, DET4, DET6, DET7, DET8, DET9, DET10 and DET11 can be measured. Similarly, when measuring the expression levels of one or more nucleic acid sequences selected from the group consisting of DET1, DET2, DET3, DET4, DET5 and DET6, one of skill in the art can measure the expression level of one, two, three, four, five or six sequences selected from the group consisting of DET1, DET2, DET3, DET4, DET5 and DET6.

In the methods of the present invention, the invention includes providing a test population which includes at least once cell that is capable of expressing one or more of the sequences DET1-11. As utilized herein, "expression" refers to the transcription of a DET gene to yield a DET nucleic acid, such as a DET mRNA. The term "expression" also refers to the transcription and translation of a DET gene to yield the encoded protein, in particular a DET protein or a fragment thereof. Therefore, one of skill in the art can detect the expression of a DET gene by monitoring DET nucleic acid production and/or expression of the DET protein. As utilized herein, "upregulated" refers to an increase in expression and "downregulated" refers to a decrease in expression.

In the methods of the present invention, the reference cell population can be from normal thyroid tissue, cancerous thyroid tissue or any other type of thyroid tissue for which a classification is known. As used herein, "a cell of a normal subject" or "normal thyroid tissue" means a cell or tissue which is histologically normal and was obtained from a subject believed to be without malignancy and having no increased risk of developing a malignancy or was obtained from tissues adjacent to tissue known to be malignant and which is determined to be histologically normal (non-malignant) as determined by a pathologist.

Using the sequence information provided herein and the sequences provided by the database entries, the expression of the DET sequences or fragments thereof can be detected, if present, and measured using techniques well known in the art. For example, sequences disclosed herein can be used to construct probes for detecting DET DNA and RNA sequences. The amount of a DET nucleic acid, for example, DET mRNA, in a cell can be determined by methods standard in the art for detecting or quantitating nucleic acid in a cell, such as in situ hybridization, quantitative PCR, Northern blotting, ELISPOT, dot blotting, etc., as well as any other method now known or later developed for detecting or quantitating the amount of a nucleic acid in a cell.

The presence or amount of a DET protein in or produced by a cell can be determined by methods standard in the art, such as Western blotting, ELISA, ELISPOT, immunoprecipitation, immunofluorescence (e.g., FACS), immunohistochemistry, immunocytochemistry, etc., as well as any other method now known or later developed for detecting or quantitating protein in or produced by a cell.

As used throughout, by "subject" is meant an individual. Preferably, the subject is a mammal such as a primate, and, more preferably, a human. The term "subject" includes domesticated animals, such as cats, dogs, etc., livestock (e.g., cattle, horses, pigs, sheep, goats, etc.), and laboratory animals (e.g., mouse, monkey, rabbit, rat, guinea pig, etc.).

The present invention also provides for detection of variants of the DET nucleic acids and polypeptides disclosed herein. In general, variants of nucleic acids and polypeptides herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two polypeptides or nucleic acids. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information or by inspection. Similarly, the present invention provides for the detection of DET proteins that are homologues of human DET proteins in other species. It would be readily apparent to one of skill in the art that the DET sequences set forth herein and in GenBank can be utilized in sequence comparisons to identify DET sequences in other species.

The sample of this invention, such as a test cell population or a reference cell population, can be from any organism and can be, but is not limited to, peripheral blood, bone marrow specimens, primary tumors, embedded tissue sections, frozen tissue sections, cell preparations, cytological preparations, exfoliate samples (e.g., sputum), fine needle aspirations, lung fluid, amnion cells, fresh tissue, dry tissue, and cultured cells or tissue. The sample can be from malignant tissue or non-malignant tissue. The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention. Furthermore, the sample can be embedded in any commercially available mounting medium, either aqueous or organic.

The sample can be on, supported by, or attached to, a substrate which facilitates detection. A substrate of the present invention can be, but is not limited to, a microscope slide, a culture dish, a culture flask, a culture plate, a culture chamber, ELISA plates, as well as any other substrate that can be used for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

Conversely, an antibody or fragment thereof, an antigenic fragment of a DET protein, or DET nucleic acid of the invention can be on, supported by, or attached to a substrate which facilitates detection. Such a substrate can include a chip, a microarray or a mobile solid support. Thus, provided by the invention are substrates including one or more of the antibodies or antibody fragments, antigenic fragments of DET proteins, or DET nucleic acids of the invention.

The nucleic acids of this invention can be detected with a probe capable of hybridizing to the nucleic acid of a cell or a sample. This probe can be a nucleic acid comprising the nucleotide sequence of a coding strand or its complementary strand or the nucleotide sequence of a sense strand or anti-sense strand, or a fragment thereof. The nucleic acid can comprise the nucleic acid of a DET gene or fragments thereof. Thus, the probe of this invention can be either DNA or RNA and can bind either DNA or RNA, or both, in the biological sample. The probe can be the coding or complementary strand of a complete DET gene or DET gene fragment.

The nucleic acids of the present invention, for example, DET1-DET11 nucleic acids and fragments thereof, can be utilized as probes or primers to detect DET nucleic acids. Therefore, the present invention provides DET polynucleotide probes or primers that can be at least 15, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350 or at least 400 nucleotides in length.

As used herein, the term "nucleic acid probe" refers to a nucleic acid fragment that selectively hybridizes under stringent conditions with a nucleic acid comprising a nucleic acid set forth in a DET sequence provided herein. This hybridization must be specific. The degree of complementarity between the hybridizing nucleic acid and the sequence to which it hybridizes should be at least enough to exclude hybridization with a nucleic acid encoding an unrelated protein.

Stringent conditions refers to the washing conditions used in a hybridization protocol. In general, the washing conditions should be a combination of temperature and salt concentration chosen so that the denaturation temperature is approximately 5-20° C. below the calculated $T_m$ of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The $T_m$ of such an oligonucleotide can be estimated by allowing 2° C. for each A or T nucleotide, and 4° C. for each G or C. For example, an 18 nucleotide probe of 50% G+C would, therefore, have an approximate $T_m$ of 54° C.

Stringent conditions are known to one of skill in the art. See, for example, Sambrook et al. (2001). An example of stringent wash conditions is 4×SSC at 65° C. Highly stringent wash conditions include, for example, 0.2×SSC at 65° C.

As mentioned above, the DET nucleic acids and fragments thereof can be utilized as primers to amplify a DET nucleic acid, such as a DET gene transcript, by standard amplification techniques. For example, expression of a DET gene transcript can be quantified by RT-PCR using RNA isolated from cells, as described in the Examples.

A variety of PCR techniques are familiar to those skilled in the art. For a review of PCR technology, see White (1997) and the publication entitled "PCR Methods and Applications" (1991, Cold Spring Harbor Laboratory Press), which is incorporated herein by reference in its entirety for amplification methods. In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference in its entirety for PCR methods. One of skill in the art would know how to design and synthesize primers that amplify a DET sequence or a fragment thereof.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g., $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product. The amplification reaction can also include a dual fluorescent probe, as described in the Examples, which hybridizes to and detects the amplification product thus allowing real time quantitation of the amplification product.

Therefore, expression of the nucleic acid(s) of the present invention can be measured by amplifying the nucleic acid(s) and detecting the amplified nucleic acid with a fluorescent probe.

For example, DET1 can be amplified utilizing forward primer GCAATCCTCTTACCTCCGCTTT (SEQ ID NO: 7) and reverse primer GGAATCGGAGACAGAAGAGAGCTT (SEQ ID NO: 8). The nucleic acid amplified by these primers can be detected with a probe comprising the nucleic acid sequence CTGGGACCACAGATGTATCCTCCACTCC (SEQ ID NO: 9) linked to a fluorescent label. These primers are merely exemplary for the amplification of DET1 as one of skill in the art would know how to design primers, based on the DET1 nucleic acid sequences provided herein, such as SEQ ID NO: 40 and the nucleic acid sequences provided by the database entries, to amplify a DET1 nucleic acid. Similarly, the probe sequences provided herein are merely exemplary for the detection of a DET1 nucleic acid, as one of skill in the art would know how to design a probe, based on the DET1 nucleic acid sequences provided herein, such as SEQ ID NO: 40 and the nucleic acid sequences provided by the database entries, to detect a DET2 nucleic acid.

DET2 can be amplified utilizing forward primer GGCTGACTGGCAAAAAGTCTTG (SEQ ID NO: 1) and reverse primer TTGGTTCCCTTAAGTTCTCAGAGTTT (SEQ ID NO: 2). The nucleic acid amplified by these primers can be detected with a probe comprising the nucleic acid sequence TGGCCCTGTCACTCCCATGATGC (SEQ ID NO: 3) linked to a fluorescent label. These primers are merely exemplary for the amplification of DET2 as one of skill in the art would know how to design primers, based on the DET2 nucleic acid sequences provided herein, such as SEQ ID NO: 42 and the nucleic acid sequences provided by the database entries, to amplify a DET2 nucleic acid. Similarly, the probe sequences provided herein are merely exemplary for the detection of a DET2 nucleic acid, as one of skill in the art would know how to design a probe, based on the DET2 nucleic acid sequences provided herein, such as SEQ ID NO: 42 and the nucleic acid sequences provided by the database entries, to detect a DET2 nucleic acid.

DET3 can be amplified utilizing forward primer TGCCAAGGAGCTTTGTTTATAGAA (SEQ ID NO: 19) and reverse primer ATGACGGCATGTACCAACCA (SEQ ID NO: 20). The nucleic acid amplified by these primers can be detected with a probe comprising the nucleic acid sequence TTGGTCCCCTCAGTTCTATGCTGTTGTGT (SEQ ID NO: 21) linked to a fluorescent label. These primers are merely exemplary for the amplification of DET3 as one of skill in the art would know how to design primers, based on the DET3 nucleic acid sequences provided herein, such as SEQ ID NO: 44 and the nucleic acid sequences provided by the database entries, to amplify a DET3 nucleic acid. Similarly, the probe sequences provided herein are merely exemplary for the detection of a DET3 nucleic acid, as one of skill in the art would know how to design a probe, based on the DET3 nucleic acid sequences provided herein, such as SEQ ID NO: 44 and the nucleic acid sequences provided by the database entries, to detect a DET3 nucleic acid.

DET4 can be amplified utilizing forward primer GCACCTGCTGAAATGTATGACATAAT (SEQ ID NO: 22) and reverse primer TTTGCTAAGTTGGAGTAAATATGATTGG (SEQ ID NO: 23). The nucleic acid amplified by these primers can be detected with a probe comprising the nucleic acid sequence ATTGTTCAGCTAATTGAGAAGCAGATTTCAGAGAGC (SEQ ID NO: 24) linked to a fluorescent label. These primers are merely exemplary for the amplification of DET4 as one of skill in the art would know how to design primers, based on the DET4 nucleic acid sequences provided herein, such as SEQ ID NO: 45 and the nucleic acid sequences provided by the database entries, to amplify a DET4 nucleic acid. Similarly, the probe sequences provided herein are merely exemplary for the detection of a DET4 nucleic acid, as one of skill in the art would know how to design a probe, based on the DET4 nucleic acid sequences provided herein, such as SEQ ID NO: 45 and the nucleic acid sequences provided by the database entries, to detect a DET4 nucleic acid.

DET5 can be amplified utilizing forward primer GACGATCCGGGTAAAGTTCCA (SEQ ID NO: 34) and reverse primer AGGTTGAGGAGTGGGTCGAA (SEQ ID NO: 35) The nucleic acid amplified by these primers can be detected with a probe comprising the nucleic acid sequence AGGCCGCGAAGCCAGTGGAATC (SEQ ID NO: 36) linked to a fluorescent label. These primers are merely exemplary for the amplification of DET5 as one of skill in the art would know how to design primers, based on the DET5 nucleic acid sequences provided herein, such as SEQ ID NO: 47 and the nucleic acid sequences provided by the database entries, to amplify a DET5 nucleic acid. Similarly, the probe sequences provided herein are merely exemplary for the detection of a DET5 nucleic acid, as one of skill in the art would know how to design a probe, based on the DET5 nucleic acid sequences provided herein, such as SEQ ID NO: 47 and the nucleic acid sequences provided by the database entries, to detect a DET5 nucleic acid.

DET6 can be amplified utilizing forward primer GCTGGTGCTCATGGCACTT (SEQ ID NO: 31) and reverse primer CCCTCCCCAGGCTTCCTAA (SEQ ID NO: 32). The nucleic acid amplified by these primers can be detected with a probe comprising the nucleic acid sequence AAGGGCTTTGCCTGACAACACCCA (SEQ ID NO: 33) linked to a fluorescent label. These primers are merely exemplary for the amplification of DET6 as one of skill in the art would know how to design primers, based on the DET6 nucleic acid sequences provided herein, such as SEQ ID NO: 49 and the nucleic acid sequences provided by the database entries, to amplify a DET6 nucleic acid. Similarly, the probe sequences provided herein are merely exemplary for the detection of a DET6 nucleic acid, as one of skill in the art would know how to design a probe, based on the DET6 nucleic acid sequences provided herein, such as SEQ ID NO: 49 and the nucleic acid sequences provided by the database entries, to detect a DET6 nucleic acid.

DET7 can be amplified utilizing forward primer CCGGCCCAAGCTCCAT (SEQ ID NO: 13) and reverse primer TTGTGTAACCGTCGGTCATGA (SEQ ID NO: 14). The nucleic acid amplified by these primers can be detected with a probe comprising the nucleic acid sequence TGTTTGGTGGAATCCATGAAGGTTATGGC (SEQ ID NO: 15) linked to a fluorescent label. These primers are merely exemplary for the amplification of DET7 as one of skill in the art would know how to design primers, based on the DET7 nucleic acid sequences provided herein, such as SEQ ID NO: 51 and the nucleic acid sequences provided by the database entries, to amplify a DET7 nucleic acid. Similarly, the probe sequences provided herein are merely exemplary for the detection of a DET7 nucleic acid, as one of skill in the art would know how to design a probe, based on the DET7 nucleic acid sequences provided herein, such as SEQ ID NO: 51 and the nucleic acid sequences provided by the database entries, to detect a DET7 nucleic acid.

DET8 can be amplified utilizing forward primer TGAGTGTCCCCCGGTATCTTC (SEQ ID NO: 28) and reverse primer CAGCCGCTTTCAGATTTTCAT (SEQ ID NO: 29). The nucleic acid amplified by these primers can be detected with a probe comprising the nucleic acid sequence CCTGCCAATCCCGATGAAATTGGAAAT (SEQ ID NO: 30) linked to a fluorescent label. These primers are merely exemplary for the amplification of DET8 as one of skill in the art would know how to design primers, based on the DET8 nucleic acid sequences provided herein, such as SEQ ID NO: 53 and the nucleic acid sequences provided by the database entries, to amplify a DET8 nucleic acid. Similarly, the probe sequences provided herein are merely exemplary for the detection of a DET8 nucleic acid, as one of skill in the art would know how to design a probe, based on the DET8 nucleic acid sequences provided herein, such as SEQ ID NO: 53 and the nucleic acid sequences provided by the database entries, to detect a DET8 nucleic acid.

DET9 can be amplified utilizing forward primer ATGGCAGTGCAGTCATCATCTT (SEQ ID NO: 10) and reverse primer GCATTCATACAGCTGCTTACCATCT (SEQ ID NO: 11). The nucleic acid amplified by these primers can be detected with a probe comprising the nucleic acid sequence TTTGGTCCCTGCCTAGGACCGGG (SEQ ID NO: 12) linked to a fluorescent label. These primers are merely exemplary for the amplification of DET9 as one of skill in the art would know how to design primers, based on the DET9 nucleic acid sequences provided herein, such as SEQ ID NO: 55 and the nucleic acid sequences provided by the database entries, to amplify a DET9 nucleic acid. Similarly, the probe sequences provided herein are merely exemplary for the detection of a DET9 nucleic acid, as one of skill in the art would know how to design a probe, based on the DET9 nucleic acid sequences provided herein, such as SEQ ID NO: 55 and the nucleic acid sequences provided by the database entries, to detect a DET9 nucleic acid.

DET10 can be amplified utilizing forward primer TGAAGAATGTCATGGTGGTAGTATCA (SEQ ID NO: 25) and reverse primer ATGACTCCTCAGGTGAATTTGTGTAG (SEQ ID NO: 26). The nucleic acid amplified by these primers can be detected with a probe comprising the nucleic acid sequence CTGGTATGGAGGGATTCTGCTAGGACCAG (SEQ ID NO: 27) linked to a fluorescent label. These primers are merely exemplary for the amplification of DET10 as one of skill in the art would know how to design primers, based on the DET10 nucleic acid sequences provided herein, such as SEQ ID NO: 57 and the nucleic acid sequences provided by the database entries, to amplify a DET10 nucleic acid. Similarly, the probe sequences provided herein are merely exemplary for the detection of a DET10 nucleic acid, as one of skill in the art would know how to design a probe, based on the DET10 nucleic acid sequences provided herein, such as SEQ ID NO: 57 and the nucleic acid sequences provided by the database entries, to detect a DET10 nucleic acid.

DET11 can be amplified utilizing forward primer GAGAGCGTGATCCCCCTACA (SEQ ID NO: 16) and reverse primer ACCAAGAGTGCACCTCAGTGTCT (SEQ ID NO: 17). The nucleic acid amplified by these primers can be detected with a probe comprising the nucleic acid sequence TCACTTCCAAATGTTCCTGTAGCAT-AAATGGTG (SEQ ID NO: 18) linked to a fluorescent label. These primers are merely exemplary for the amplification of DET11 as one of skill in the art would know how to design primers, based on the DET11 nucleic acid sequences provided herein, such as SEQ ID NO: 59 and the nucleic acid sequences provided by the database entries, to amplify a DET11 nucleic acid. Similarly, the probe sequences provided herein are merely exemplary for the detection of a DET11 nucleic acid, as one of skill in the art would know how to design a probe, based on the DET11 nucleic acid sequences provided herein, such as SEQ ID NO: 59 and the nucleic acid sequences provided by the database entries, to detect a DET11 nucleic acid.

The sample nucleic acid, e.g. amplified fragment, can be analyzed by one of a number of methods known in the art. The nucleic acid can be sequenced by dideoxy or other methods. Hybridization with the sequence can also be used to determine its presence, by Southern blots, dot blots, etc.

The DET nucleic acids of the invention can also be used in polynucleotide arrays. Polynucleotide arrays provide a high throughput technique that can assay a large number of polynucleotide sequences in a single sample. This technology can be used, for example, as a diagnostic tool to identify samples with differential expression of DET nucleic acids as compared to a reference sample.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences of DET1-DET11. The substrate can be any substrate to which polynucleotide probes can be attached, including but not limited to glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593, 839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Tissue samples can be treated to form single-stranded polynucleotides, for example by heating or by chemical denaturation, as is known in the art. The single-stranded polynucleotides in the tissue sample can then be labeled and hybridized to the polynucleotide probes on the array. Detectable labels which can be used include but are not limited to radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

The present invention also provides methods of detecting and measuring a DET protein or fragment thereof. An amino acid sequence for a C21orf4 (DET1) protein is set forth herein as SEQ ID NO: 41. An amino acid sequence for a Hs. 145049 (DET2) protein is set forth herein as SEQ ID NO: 43. An amino acid sequence for a KIT (DET4) protein is set forth herein as SEQ ID NO: 46. An amino acid sequence for a LSM7 (DET5) protein is set forth herein SEQ ID NO: 48. An amino acid sequence for a SYNGR2 (DET6) protein is set forth herein as SEQ ID NO: 50. An amino acid sequence for a C11orf8 (DET7) protein is provided herein as SEQ ID NO: 52. An amino acid sequence for a CDH1 (DET8) protein is set forth herein as SEQ ID NO: 54. An amino acid sequence for a FAM13A1 (DET9) protein is set forth herein as SEQ ID NO: 56. An amino acid sequence for IMPACT (DET10) protein is provided herein as SEQ ID NO: 58. An amino acid sequence for KIAA1128 (DET11) protein is set forth herein as SEQ ID NO: 60. Therefore, the present invention provides antibodies that bind to the DET protein sequences or fragments thereof set forth herein. The antibody utilized to detect a DET polypeptide, or fragment thereof, can be linked to a detectable label either directly or indirectly through use of a secondary and/or tertiary antibody; thus, bound antibody, fragment or molecular complex can be detected directly in an ELISA or similar assay.

The sample can be on, supported by, or attached to, a substrate which facilitates detection. A substrate of the present invention can be, but is not limited to, a microscope slide, a culture dish, a culture flask, a culture plate, a culture chamber, ELISA plates, as well as any other substrate that can be used for containing or supporting biological samples for analysis according to the methods of the present invention. The substrate can be of any material suitable for the purposes of this invention, such as, for example, glass, plastic, polystyrene, mica and the like. The substrates of the present invention can be obtained from commercial sources or prepared according to standard procedures well known in the art.

Conversely, an antibody or fragment thereof, an antigenic fragment of a DET protein can be on, supported by, or attached to a substrate which facilitates detection. Such a substrate can be a mobile solid support. Thus, provided by the invention are substrates including one or more of the antibodies or antibody fragments, or antigenic fragments of a DET polypeptide.

In the methods of the present invention, once the expression levels of one or more DET nucleic acids is measured, these expression levels are comparing to the expression of the nucleic acid sequence(s) in a reference cell population comprising at least one cell for which a thyroid lesion classification is known. Once this comparison is performed, a difference in expression levels, if present, is identified by one of skill in the art.

A difference or alteration in expression of one or more DET nucleic acids in the test cell population, as compared to the reference cell population, indicates that the test cell population is different from the reference cell population. By "difference" or "alteration" is meant that the expression of one or more DET nucleic acid sequences is either increased or decreased as compared to the expression levels of the reference cell population. If desired, but not necessary, relative expression levels within the test and reference cell populations can be normalized by reference to the expression level of a nucleic acid sequence that does not vary according to thyroid cancer stage in the subject. The absence of a difference or alteration in expression of one or more DET nucleic acids in the test cell population, as compared to the reference cell population, indicates that the test cell population is similar to the reference cell population. As an example, if the reference cell population is from normal thyroid tissue, a similar DET gene expression profile in the test cell population indicates that the test cell population is also normal whereas a different profile indicates that the test cell population is not normal. By "similar" is meant that an expression pattern does not have to be exactly like the expression pattern but similar enough such that one of skill in the art would know that the expression pattern is more closely associated with one type of tissue than with another type of tissue. In another example, if the reference cell population is from malignant thyroid tissue, a similar DET gene expression profile in the test cell population indicates that the test cell population is also malignant whereas a different profile indicates that the test cell population is not malignant. Similarly, if the reference cell population is from benign thyroid tissue, a similar DET gene expression profile in the test cell population indicates that the test cell population is also benign whereas a different profile indicates that the test cell population is not benign.

Upon observing a difference between the test cell population and a normal reference cell population, one of skill in the art can classify the test cell population as benign or malignant by comparing the expression pattern to known expression patterns for benign and malignant cells. This comparison can be done by comparing the expression pattern of the test cell population to the expression pattern obtained from a plurality of reference cells used as a control while measuring expression levels in the test cell population. One of skill in the art can also compare the expression pattern of the test cell population with a database of expression patterns corresponding to normal, benign and malignant cells and subcategories thereof. For example, upon observing a difference between the test cell population and a reference cell population from normal thyroid tissue, one of skill in the art can compare the expression pattern of the test cell population with a database of expression patterns corresponding to normal, benign and malignant cells. One of skill in the art would then determine which expression pattern in the database is most similar to the expression pattern obtained for the test cell population and classify the test cell population as benign or malignant, as well as classify the test cell population as a type of benign or malignant lesion. For example, if the test cell population is classified as being from a benign lesion, this population can be further classified as being from a follicular adenoma, hyperplastic nodule or papillary adenoma or any other type of benign thyroid lesion. If the test cell population is classified as being from a malignant lesion, this population can be further classified as being from papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma or any other type of malignant thyroid lesion. Therefore, utilizing the methods of the present invention, one of skill in the art can diagnose a benign or malignant lesion in a subject, as well as the type of benign or malignant lesion in the subject.

Staging of Thyroid Cancer

Once a subject has been diagnosed with a malignant lesion or thyroid tumor, the stage of thyroid malignancy can also be determined by the methods of the present invention. Staging of a thyroid malignancy or tumor can be useful in prescribing treatment as well as in determining a prognosis for the subject.

Therefore, also provided by the present invention is a method of identifying the stage of a thyroid tumor in a subject comprising: a) measuring the expression of one or more nucleic acid sequences selected from the group consisting of DET1, DET2, DET3, DET4, DET6, DET7, DET8, DET9, DET10 and DET11 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of said nucleic acid sequences to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby identifying the stage of the thyroid tumor in the subject.

Also provided by the present invention is a method of identifying the stage of a thyroid tumor in a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of said nucleic acid sequences to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby identifying the stage of the thyroid tumor in the subject.

Also provided by the present invention is a method of determining a prognosis for subject comprising: a) measuring the expression of one or more nucleic acid sequences selected from the group consisting of DET1, DET2, DET3, DET4, DET6, DET7, DET8, DET9, DET10 and DET1 in a test cell population, wherein at least one cell in said test cell population is capable of expressing one or more nucleic acid sequences selected from the group consisting of DET1, DET2, DET3, DET4, DET6, DET7, DET8, DET9, DET10 and DET11; b) comparing the expression of said nucleic acid sequences to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, thereby determining the prognosis for the subject.

Also provided by the present invention is a method of determining the prognosis for a subject comprising: a) measuring the expression of one or more nucleic acid sequences selected from the group consisting of DET1, DET2, DET3, DET4, DET5 and DET6 in a test cell population, wherein at least one cell in said test cell population is capable of expressing one or more nucleic acid sequences selected from the group consisting of DET1, DET2, DET3, DET4, DET5 and DET6; b) comparing the expression of said nucleic acid sequences to the expression of the nucleic acid sequence(s) in a reference cell population comprising at least one cell for which a thyroid tumor stage is known; and c) identifying a difference, if present, in expression levels of one or more nucleic acid sequences selected from the group consisting of DET1, DET2, DET3, DET4, DET5 and DET6, in the test cell population and reference cell population, thereby determining the prognosis for the subject.

In staging a thyroid tumor, once the expression levels of one or more DET nucleic acids is measured, these expression levels are comparing to the expression of the nucleic acid sequence(s) in a reference cell population comprising at least one cell for which a stage of thyroid tumor is known. Once this comparison is performed, a difference in expression levels, if present, is identified by one of skill in the art.

A difference or alteration in expression of one or more DET nucleic acids in the test cell population, as compared to the reference cell population, indicates that the test cell population is at a different stage than the stage of the reference cell population. By "difference" or "alteration" is meant that the expression of one or more DET nucleic acid sequences is either increased or decreased as compared to the expression levels of the reference cell population. If desired, but not necessary, relative expression levels within the test and reference cell populations can be normalized by reference to the expression level of a nucleic acid sequence that does not vary according to thyroid cancer stage in the subject. The absence of a difference or alteration in expression of one or more DET nucleic acids in the test cell population, as compared to the reference cell population, indicates that the test cell population is at the same stage as that of the reference cell population. As an example, if the reference cell population is from an early stage thyroid tumor, a similar DET gene expression profile in the test cell population indicates that the test cell population is also from an early stage thyroid tumor whereas a different profile indicates that the test cell population is not from an early stage thyroid tumor. By "similar" is meant that an expression pattern does not have to be exactly like the expression pattern but similar enough such that one of skill in the art would know that the expression pattern is more closely associated with one stage than with another stage.

In order to establish a database of stages of thyroid cancer, one skilled in the art can measure DET nucleic acid levels and/or DET polypeptide levels in numerous subjects in order to establish expression patterns that correspond to clinically defined stages such as, for example, 1) normal, 2) at risk of developing thyroid cancer, 3) pre-cancerous or 4) cancerous as well as other substages defined within each of these stages. These stages are not intended to be limiting as one of skill in the art may define other stages depending on the type of sample, type of cancer, age of the subject and other factors. This database can then be used to compare an expression pattern from a test sample and make clinical decisions. Upon correlation of a DET expression pattern with a particular stage of thyroid cancer, the skilled practitioner can administer a therapy suited for the treatment of cancer. The present invention also allows the skilled artisan to correlate a DET expression pattern with a type of thyroid lesion and correlate the expression pattern with a particular stage of thyroid cancer. The subjects of this invention undergoing anti-cancer therapy can include subjects undergoing surgery, chemotherapy, radiotherapy, immunotherapy or any combination thereof. Examples of chemotherapeutic agents include cisplatin, 5-fluorouracil and S-1. Immunotherapeutics methods include administration of interleukin-2 and interferon-α.

In determining the prognosis for a subject, once the expression levels of one or more DET nucleic acids is measured, these expression levels are comparing to the expression of the nucleic acid sequence(s) in a reference cell population comprising at least one cell for which a prognosis is known. Once this comparison is performed, a difference in expression levels, if present, is identified by one of skill in the art.

One skilled in the art can measure DET nucleic acid levels and/or DET polypeptide levels in order to determine a prognosis for a subject. One of skill in the art can measure DET nucleic acid levels and/or DET polypeptide levels in numerous subjects with varying prognoses in order to establish reference expression patterns that correspond to prognoses for subjects. As utilized herein, "prognosis" means a prediction of probable development and/or outcome of a disease. These reference expression patterns or a database of reference expression patterns can then be used to compare an expression pattern from a test sample and determine what the prognosis for a subject is. These expression patterns can also be used to compare an expression pattern from a test sample from a subject and determine whether or not a subject can recover from the disease. Upon correlation of a DET expression pattern with a particular prognosis, the skilled practitioner can then determine if a therapy suited for the treatment of cancer is applicable.

The present invention provides a computer system comprising a) a database including records comprising a plurality of reference DET gene expression profiles or patterns for benign, malignant and normal tissue samples and associated diagnosis and therapy data; and b) a user interface capable of receiving a selection of one or more test gene expression profiles for use in determining matches between the test expression profiles and the reference DET gene expression profiles and displaying the records associated with matching expression profiles. The database can also include DET gene expression profiles for subclasses of benign tissue samples such as follicular adenoma, hyperplastic nodule, papillary adenoma, thyroiditis nodule and multinodular goiter. The database can also include DET gene expression profiles for subclasses of malignant tissue samples such as papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma. The database can also include DET gene expression profiles for stages of thyroid cancer as well as DET gene expression profiles that correspond to prognoses for subjects.

It will be appreciated by those skilled in the art that the DET gene expression profiles provided herein as well as the DET expression profiles identified from samples and subjects can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate a list of DET gene expression profiles comprising one or more of the DET expression profiles of the invention. Another aspect of the present invention is a computer readable medium having recorded thereon at least 2, 5, 10, 15, 20, 25, 30, 50, 100, 200, 250, 300, 400, 500, 1000, 2000, 3000, 4000 or 5000 expression profiles of the invention or expression profiles identified from subjects.

Computer readable media include magnetically readable media, optically readable media, electronically readable media and magnetic/optical media. For example, the computer readable media may be a hard disc, a floppy disc, a magnetic tape, CD-ROM, DVD, RAM, or ROM as well as other types of other media known to those skilled in the art.

Embodiments of the present invention include systems, particularly computer systems which contain the DET gene expression information described herein. As used herein, "a computer system" refers to the hardware components, software components, and data storage components used to store and/or analyze the DET gene expression profiles of the present invention or other DET gene expression profiles. The computer system preferably includes the computer readable media described above, and a processor for accessing and manipulating the DET gene expression data.

Preferably, the computer is a general purpose system that comprises a central processing unit (CPU), one or more data storage components for storing data, and one or more data retrieving devices for retrieving the data stored on the data storage components. A skilled artisan can readily appreciate that any one of the currently available computer systems are suitable.

In one particular embodiment, the computer system includes a processor connected to a bus which is connected to a main memory, preferably implemented as RAM, and one or more data storage devices, such as a hard drive and/or other computer readable media having data recorded thereon. In some embodiments, the computer system further includes one or more data retrieving devices for reading the data stored on the data storage components. The data retrieving device may represent, for example, a floppy disk drive, a compact disk drive, a magnetic tape drive, a hard disk drive, a CD-ROM drive, a DVD drive, etc. In some embodiments, the data storage component is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device. Software for accessing and processing the expression profiles of the invention (such as search tools, compare tools, modeling tools, etc.) may reside in main memory during execution.

In some embodiments, the computer system may further comprise a program for comparing expression profiles stored on a computer readable medium to another test expression profile on a computer readable medium. An "expression profile comparer" refers to one or more programs which are implemented on the computer system to compare an expression profile with other expression profiles.

Accordingly, one aspect of the present invention is a computer system comprising a processor, a data storage device having stored thereon a DET gene expression profile of the invention, a data storage device having retrievably stored thereon reference DET gene expression profiles to be compared with test or sample sequences and an expression profile comparer for conducting the comparison. The expression profile comparer may indicate a similarity between the expression profiles compared or identify a difference between the two expression profiles.

Alternatively, the computer program may be a computer program which compares a test expression profile(s) from a subject or a plurality of subjects to a reference expression profile (s) in order to determine whether the test expression profile(s) differs from or is the same as a reference expression profile.

This invention also provides for a computer program that correlates DET gene expression profiles with a type of cancer and/or a stage of cancer and/or a prognosis. The computer program can optionally include treatment options or drug indications for subjects with DET gene expression profiles associated with a type of cancer and/or stage of cancer.

Screening Methods

Further provided by the present invention is a method of identifying an agent for treating a thyroid tumor, the method comprising: a) contacting a population of thyroid tumor cells from a subject for which a tumor stage is known, wherein at least one cell in said population is capable of expressing one or more nucleic acid sequences selected from the group consisting of DET1, DET2, DET3, DET4, DET6, DET7, DET8, DET9, DET10 and DET11, with a test agent; b) measuring the expression of one or more nucleic acid sequences selected from the group consisting of DET1, DET2, DET3, DET4, DET6, DET7, DET8, DET9, DET10 and DET11 in the cell population; c) comparing the expression of the nucleic acid sequence(s) to the expression of the nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET6, DET7, DET8, DET9, DET10 and DET11, in the test cell population and reference cell population, such that if there is a difference corresponding to an improvement, a therapeutic agent for treating thyroid tumor has been identified.

Further provided by the present invention is a method of identifying an agent for treating a thyroid tumor, the method comprising: a) contacting a population of thyroid tumor cells from a subject for which a tumor stage is known, wherein at least one cell in said test population is capable of expressing one or more nucleic acid sequences selected from the group consisting of DET1, DET2, DET3, DET4, DET5 and DET6, with a test agent; b) measuring the expression of one or more nucleic acid sequences selected from the group consisting of DET1, DET2, DET3, DET4, DET5 and DET6 in the cell population; c) comparing the expression of the nucleic acid sequence(s) to the expression of the nucleic acid sequence(s) in a reference cell population comprising at least one cell for which a thyroid tumor stage is known; and d) identifying a difference, if present, in expression levels of one or more nucleic acid sequences selected from the group consisting of DET1, DET2, DET3, DET4, DET5 and DET6, in the cell population and reference cell population, such that if there is a difference corresponding to an improvement, a therapeutic agent for treating thyroid tumor has been identified.

The test agents used in the methods described herein can be made by methods standard in the art and include, but are not limited to, chemicals, small molecules, antisense molecules, siRNAs, drugs, antibodies, peptides and secreted proteins.

By "improvement" is meant that the treatment leads to a shift in a thyroid tumor stage to a less advanced stage. As mentioned above, the expression pattern obtained for the test cell population can be compared to expression patterns in a database before and after contacting the test cell population with a test agent to determine the stage of the test cell population before and after treatment.

The reference cell population can be from normal thyroid tissue. For example, if the cell population from the subject is from an early stage thyroid tumor, and after treatment, the expression pattern of the cell population when compared to the reference cell population from normal thyroid tissue, is similar to that of the reference cell population, the agent is effective in treating a thyroid tumor. By "similar" is meant that the expression pattern does not have to be exactly like the expression pattern from normal thyroid tissue but similar enough such that one of skill in the art would know that the treatment leads to expression patterns more closely associated with normal thyroid tissue. As an another example, if both the cell population from the subject and the reference cell population are from an early stage thyroid tumor, and after treatment, the expression pattern of the cell population is similar to the reference cell population, the agent is not effective in treating a thyroid tumor. By "similar" is meant that the expression pattern does not have to be exactly like the expression pattern from the early stage thyroid tumor cell population but similar enough such that one of skill in the art would know that the treatment does not lead to an expression pattern corresponding to a less advanced thyroid tumor stage. As another example, if both the cell population from the subject and the reference cell population are from an early stage thyroid tumor, and after treatment, the expression pattern of the cell population is different from the reference cell population, and correlates with a less advanced thyroid tumor stage, the agent is effective in treating a thyroid tumor. These examples are not intended to be limiting with regard to the types of thyroid tumor populations that can be contacted with an agent, the types of agents that can be utilized, the type of reference cell population that can be utilized or the effects observed as there are numerous variations known to one of skill in the art for performing these methods.

Treatment Methods

Also provided by the present invention is a method of treating malignant thyroid lesions or thyroid cancer in a subject suffering from or at risk of developing thyroid cancer comprising administering to the subject an agent that modulates the expression of one or more DET sequences. By "at risk for developing" is meant that the subject's prognosis is less favorable and that the subject has an increased likelihood of developing thyroid cancer. Administration of the agent can be prophylactic or therapeutic.

My "modulation" is meant that the expression of one or more DET sequences can be increased or decreased.

For example, KIT (DET4), LSM7 (DET5), FAM13A1 (DET9), C11orf8 (DET7), KIAA1128 (DET11), IMPACT (DET10) and CDH1 (DET8) were all downregulated or underexpressed in malignant thyroid lesions as compared to normal thyroid tissue. Therefore, a subject can be treated with an effective amount of an agent that increases the amount of the downregulated or underexpressed nucleic acids in the subject. Administration can be systemic or local, e.g. in the immediate vicinity of the subject's cancerous cells. This agent can be for example, the protein product of a downregulated or underexpressed DET gene or a biologically active fragment thereof, a nucleic acid encoding a downregulated or underexpressed DET gene and having expression control sequences permitting expression in the thyroid cancer cells or an agent which increases the endogenous level of expression of the gene.

With regard to genes that are upregulated or overexpressed as compared to normal thyroid tissue, C21orf4 (DET1), Hs.145049 (DET2) were upregulated or overexpressed in malignant thyroid lesions as compared to normal thyroid tissue. Therefore, a subject can be treated with an effective amount of an agent that decreases the amount of the upregulated or overexpressed nucleic acids in the subject. Administration can be systemic or local, e.g. in the immediate vicinity of the subject's cancerous cells. The agent can be, for example, a nucleic acid that inhibits or antagonizes the expression of the overexpressed DET gene, such as an antisense nucleic acid or an siRNA. The agent can also be an antibody that binds to a DET protein that is overexpressed.

In the treatment methods of the present invention, the subject can be treated with one or more agents which decrease the expression of overexpressed DET sequences alone or in combination with one or more agents which increase the expression of DET sequences that are downregulated or underexpressed in thyroid cancer. The subject can also be treated with one or more agents which increase the expression of DET sequences alone or in combination with one or more agents which decrease the expression of overexpressed DET sequences.

These treatment methods can be combined with other anticancer treatments such as surgery, chemotherapy, radiotherapy, immunotherapy or any combination thereof. Examples of chemotherapeutic agents include cisplatin, 5-fluorouracil and S-1. Immunotherapeutics methods include administration of interleukin-2 and interferon-α.

Identification of Differentially Expressed Thyroid Genes

The present invention also provides a method of identifying differentially expressed genes and/or expression patterns for such genes in other types of benign and malignant lesions. As set forth in the Examples, one of skill in the art can utilize gene expression profiling and supervised machine learning algorithms to construct a molecular classification scheme for other types of thyroid tumors. These include any type of benign lesion such as papillary adenoma, multinodular goiter or thyroiditis nodule, and any type of malignant lesion, such as papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma. Those genes and expression patterns identified via these method can be utilized in the methods of the present invention to diagnose, stage and treat cancer.

Kits

The present invention also provides for a kit comprising one or more reagents for detecting one or more nucleic acid sequences selected from the group consisting of DET1-DET11. In various embodiments the expression of one or more of the sequences represented by DET1-DET11 are measured. The kit can identify the DET nucleic acids by having homologous nucleic acid sequences, such as oligonucleotide sequences, complimentary to a portion of the recited nucleic acids, or antibodies to proteins encoded by the DET nucleic acids. The kit can also include amplification primers for performing RT-PCR, such as those set forth in Table 4 and probes, such as those set forth in Table 4, that can be fluorescently labeled for detecting amplification products in, for example, a Taqman assay. The kits of the present invention can optionally include buffers, enzymes, detectable labels and other reagents for the detecting expression of DET sequences described herein.

The following examples are put forth so as to provide those of ordinary skill in the art with a complete disclosure and description of how the antibodies, polypeptides, nucleic acids, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

EXAMPLES

DNA microarrays allow quick and complete evaluation of a cell's transcriptional activity. Expression genomics is very powerful in that it can generate expression data for a large number of genes simultaneously across multiple samples. In cancer research, an intriguing application of expression arrays includes assessing the molecular components of the neoplastic process and in cancer classification (1). Classification of human cancers into distinct groups based on their molecular profile rather than their histological appearance can be more relevant to specific cancer diagnoses and cancer treatment regimes. Several attempts to formulate a consensus about classification and treatment of thyroid carcinoma based on standard histopathologic analysis have resulted in published guidelines for diagnosis and initial disease management (2). In the past few decades no improvement has been made in the differential diagnosis of thyroid tumors by fine needle aspiration biopsy (FNA), specifically suspicious or indeterminate thyroid lesions, suggesting that a new approach to this should be explored. Therefore in this study a gene expression approach was developed to diagnose benign vs malignant thyroid lesions in 73 patients with thyroid tumors. A 10 gene and 6 gene model were developed to be able to differentiate benign vs. malignant thyroid tumors. These results provide a molecular classification system for thyroid tumors and this in turn provides a more accurate diagnostic tool for the clinician managing patients with suspicious thyroid lesions.

It is well known that cancer results from changes in gene expression patterns that are important for cellular regulatory processes such as growth, differentiation, DNA duplication, mismatch repair and apoptosis. It is also becoming more apparent that effective treatment and diagnosis of cancer is dependent upon an understanding of these important processes. Classification of human cancers into distinct groups based on their origin and histopathological appearance has historically been the foundation for diagnosis and treatment. This classification is generally based on cellular architecture, certain unique cellular characteristics and cell-specific antigens only. In contrast, gene expression assays have the potential to identify thousands of unique characteristics for each tumor type (3) (4). Elucidating a genome wide expression pattern for disease states not only could have a enormous impact on our understanding of specific cell biology, but could also provide the necessary link between molecular genetics and clinical medicine (5) (6) (7).

Thyroid carcinoma represents 1% of all malignant diseases, but 90% of all neuroendocrine malignancies. It is estimated that 5-10% of the population will develop a clinically significant thyroid nodule during their life-time (8). The best available test in the evaluation of a patient with a thyroid nodule is fine needle aspiration biopsy (FNA) (9). Of the malignant FNAs, the majority are from papillary thyroid cancers (PTC) or its follicular variant (FVPTC). These can be easily diagnosed if they have the classic cytologic features including abundant cellularity and enlarged nuclei containing intra-nuclear grooves and inclusions (10). Indeed, one third of the time these diagnoses are clear on FNA. Fine needle aspiration biopsy of thyroid nodules has greatly reduced the need for thyroid surgery and has increased the percentage of malignant tumors among excised nodules (11, 12). In addition, the diagnosis of malignant thyroid tumors, combined with effective therapy, has lead to a marked decrease in morbidity due to thyroid cancer. Unfortunately, many thyroid FNAs are not definitively benign or malignant, yielding an "indeterminate" or "suspicious" diagnosis. The prevalence of indeterminate FNAs varies, but typically ranges from 10-25% of FNAs (13-15). In general, thyroid FNAs are indeterminate due to overlapping or undefined morphologic criteria for benign versus malignant lesions, or focal nuclear atypia within otherwise benign specimens. Of note, twice as many patients are referred for surgery for a suspicious lesion (10%) than for a malignant lesion (5%), an occurrence that is not widely appreciated since the majority of FNAs are benign. Therefore when the diagnosis is unclear on FNA these patients are classified as having a suspicious or indeterminate lesion only. It is well known that frozen section analysis often yields no additional information.

The question then arises: "Should the surgeon perform a thyroid lobectomy, which is appropriate for benign lesions or a total thyroidectomy, which is appropriate for malignant lesions when the diagnosis is uncertain both preoperatively and intra-operatively?" Thyroid lobectomy as the initial procedure for every patient with a suspicious FNA could result in the patient with cancer having to undergo a second operation for completion thyroidectomy. Conversely, total thyroidectomy for all patients with suspicious FNA would result in a majority of patients undergoing an unnecessary surgical procedure, requiring lifelong thyroid hormone replacement and exposure to the inherent risks of surgery (16).

There is a compelling need to develop more accurate initial diagnostic tests for evaluating a thyroid nodule. Recent studies suggest that gene expression data from cDNA microarray analysis holds promise for improving tumor classification and for predicting response to therapy among cancer patients (17) (18) (19). No clear consensus exists regarding which computational tool is optimal for the analysis of large gene expression profiling datasets, especially when they are used to predict outcome (20).

This invention describes the use of gene expression profiling and supervised machine learning algorithms to construct a molecular classification scheme for thyroid tumors (22). The gene expression signatures provided herein include new tumor related genes whose encoded proteins can be useful for improving the diagnosis of thyroid tumors.

Tissue Samples

Thyroid tissues collected under John Hopkins University Hospital Institutional Review Board-approved protocols were snap-frozen in liquid nitrogen and stored at −80° C. until use. The specimens were chosen based on their tumor type: papillary thyroid carcinoma (PTC n=17), follicular variant of PTC (FVPTC n=15), follicular adenoma (FA n=16) and hyperplastic nodule (HN n=15). All diagnoses were made by the Surgical Pathology Department at Johns Hopkins.

Tissue Processing and Isolation of RNA

Frozen sections of 100-300 mg of tissue were collected in test tubes containing 1 ml of Trizol. Samples were transferred to FastRNA tubes containing mini beads and homogenized in a FastPrep beater (Bio101Savant, Carlsbad, Calif.) for 1.5 min at speed 6. The lysate was transferred to a new tube and total RNA was extracted according to the Trizol protocol (Molecular Research Center, Inc. Cincinnati, Ohio). Approximately 12 ug of total RNA was obtained from each tumor sample. The total RNA was then subjected to two rounds of amplification following the modified Eberwine method (23) (24) resulting in approximately 42 µg of messenger RNA (mRNA). The quality of the extracted RNA was tested by spectrophotometry and by evaluations on minichips (BioAnalyzer, Agilent Technologies, Palo Alto, Calif.).

Microarray Analysis

Hybridization was performed on 10 k human cDNA microarrays, Hs-UniGem2, produced by the NCI/NIH (ATC, Gaithersburg, Md.). Comparisons were made for each tumor with the same control which consisted of amplified RNA extracted from normal thyroid tissue and provided by Ambion Inc (Austin, Tex.). Fluorescent marker dyes (Cy5 and Cy3) were used to label the test and control samples, respectively. The respective dyes and samples were also switched in order to test for any labeling bias. The mixture of the two populations of RNA species was then hybridized to the same microarray and incubated for 16 hr at 42° C. cDNA microarrays were then washed and scanned using the GenePix® 4000B (Axon Instruments Inc., CA) and images were analyzed with GenePix software version 3.0. For each sample a file containing the image of the array and an Excel file containing the expression ratio values for each gene was uploaded onto the MadbArray web-site (National Center for Biotechnology Information/NIH) http://nciarray.nci.nih.gov for further analysis. To accurately compare measurements from different experiments, the data was normalized and the ratio (Signal Cy5/Signal Cy3) was calculated so that the median (Ratio) was 1.0.

Immunohistochemistry

Figure 6:
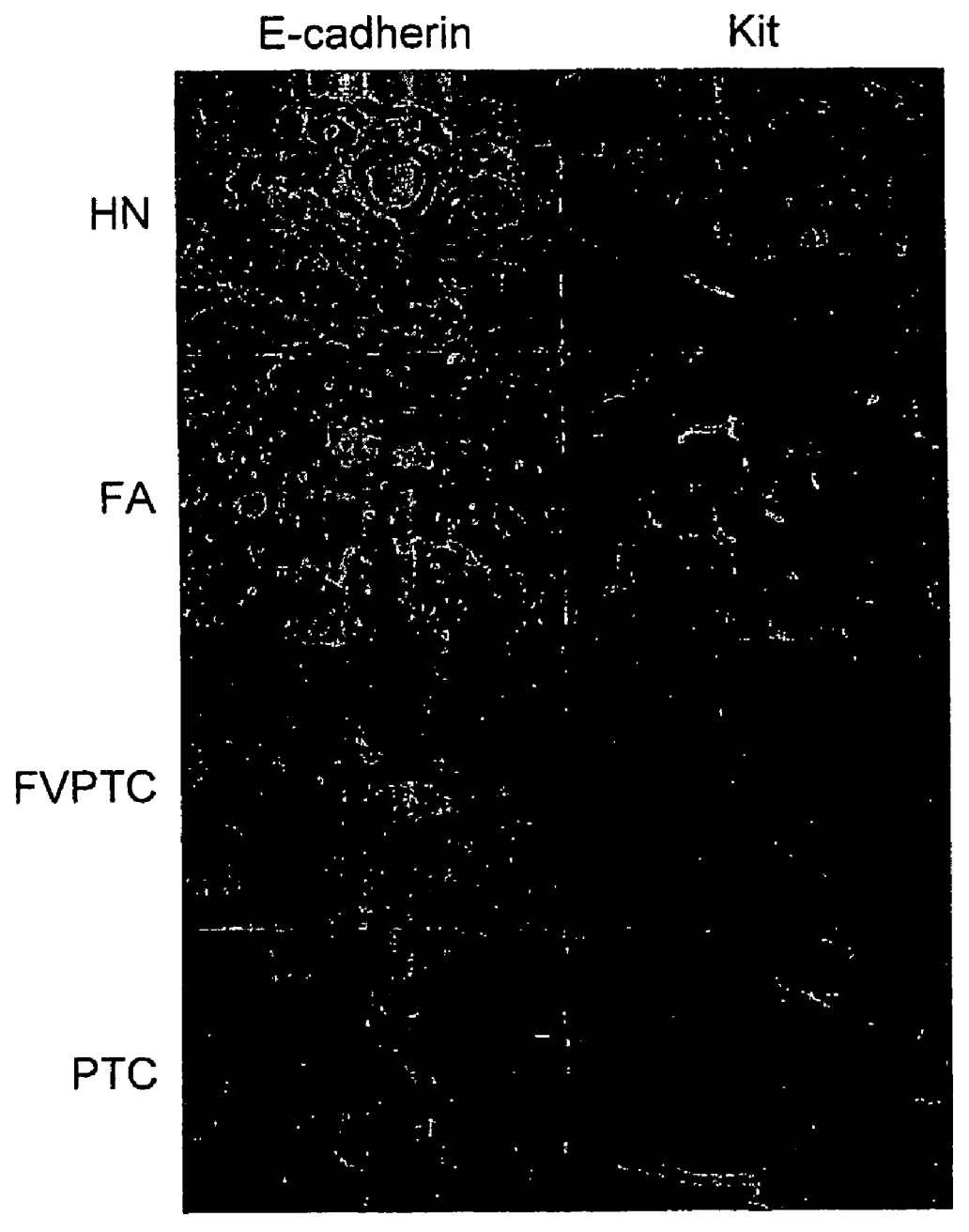

Immunohistochemistry studies utilizing antibodies to two gene products in the predictor models have also been performed and this data correlates with the expression data. Taqman analysis was performed for CHD1 and KIT. Both KIT and CDH1 expression decreased in malignancy, which correlates with the microarray data. As shown in FIG. 6, immunohistochemical results show that both KIT and CDH1 expression decrease in malignancy which correlates with the expression results obtained via microarray and Taqman analysis.

Statistical Analysis

Data from the 73 thyroid tumors was used to build a benign (FA and HN) vs. malignant (PTC and FVPTC) expression ratio-based model, capable of predicting the diagnosis (benign vs malignant) of each sample. After normalization, a file containing the gene expression ratio values from all 73 samples was imported into a statistical analysis software package (Partek Inc., MO). Samples were divided in two sets: one set (63 samples) was used to train the diagnosis predictor model and a second set (10) was used as a validation set to test the model. These 10 samples were not previously used to do any other analysis. As a first step, the data from the 63 samples was subjected to Principal Component Analysis (PCA) to perform an exploratory analysis and to view the overall trend of the data. PCA is an exploratory technique that describes the structure of high dimensional data by reducing its dimensionality. It is a linear transformation that converts n original variables (gene expression ratio values) into n new variables or principal components (PC) which have three important properties: they 1) are ordered by the amount of variance explained; 2) are uncorrelated and; 3) they explain all variation in the data. The new observations (each array) are represented by points in a three dimensional space. The distance between any pair of points is related to the similarity between the two observations in high dimensional space. Observations that are near each other are similar for a large number of variables and conversely, the ones that are far apart are different for a large number of variables.

An Anova test with Bonferroni correction was then used to identify genes that were statistically different between the two groups. The resulting significant genes were used to build a diagnosis-predictor model. Variable (gene) selection analysis with cross-validation was performed different times, each time testing a different number of gene combinations. For cross-validation the "leave-one-out" method was used to estimate the accuracy of the output class prediction rule: the whole dataset was divided into different parts and each part was individually removed from the data set. The remaining data set was used to train a class prediction rule; and the resulting rule was applied to predict the class of the "held-out" sample.

Figure 2:
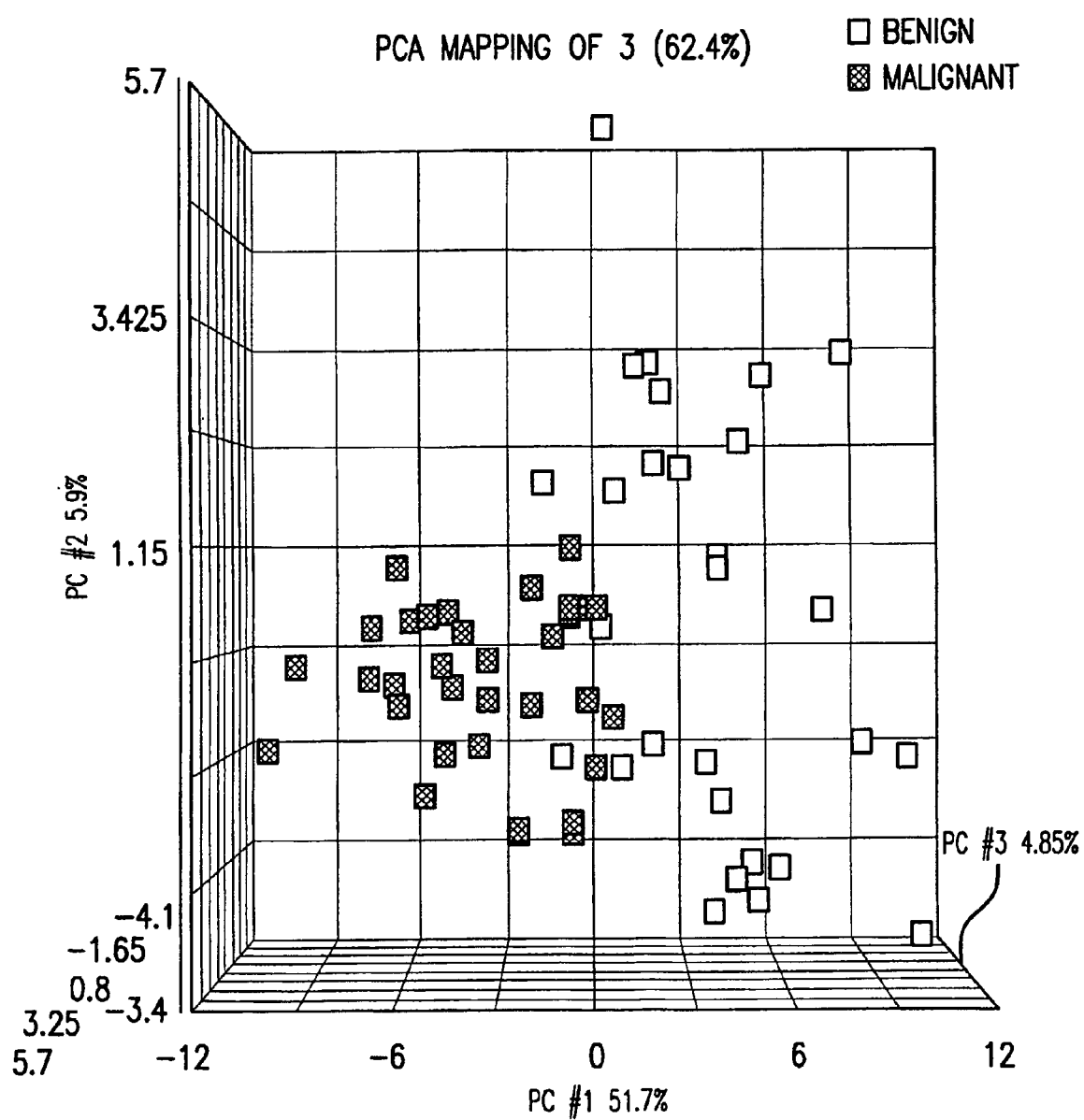
FIG. 2 shows PCA organization in a three-dimensional space of all samples divided into two groups: benign (HN-FA) and malignant (FVPTC-PTC). Each dot represents how that sample is localized in-space on the basis of its gene expression profile. The distance between any pair of points is related to the similarity between the two observations in high dimensional space.

Anova test with Bonferroni correction was used on 9100 genes to identify ones that were statistically different among the 4 groups. PCA analysis of the 63 samples (FIG. 1) using the statistically significant genes showed a clear organization of the samples based on diagnosis. The same analysis (Anova test with Bonferroni correction) was performed on the dataset organized, this time, in benign (HN-FA) and malignant (PTC-FVPTC). For this analysis, 47 genes were found to be significantly different between the benign and the malignant group (Table 1). PCA analysis also separated the data clearly into two groups (FIG. 2).

For the purpose of this invention, attention was focused on the analysis of the dataset separating benign from malignant. These 47 genes were used to build a diagnostic predictor model. Variable (gene) selection analysis with cross validation was performed with a different number of gene combinations. After cross-validation the model was 87.1% accurate in predicting benign versus malignant with an error rate of 12.9% (Table 2). This suggested that it was possible to use the data to create a diagnostic predictor model.

The most accurate results were obtained with a combination of 6 to 10 genes. This combination of genes constituted a predictor model and a validation set of 10 additional thyroid samples was used to confirm the accuracy of this model (Table 3). The pathologic diagnosis for each sample was kept blinded to researchers at the time of the analysis. When the blind was broken, it was found that 9 of the samples were diagnosed in concordance with the pathologic diagnosis by our model. One sample that was originally diagnosed as a benign tumor by standard histologic criteria, was diagnosed as malignant by our model. This sample was re-reviewed by the Pathology Department at The Johns Hopkins Hospital and was subsequently found to be a neoplasm of uncertain malignant potential. The diagnosis was changed by pathology after review for clinical reasons, not because of the gene profiling. What is so extraordinary about this is that this was not discovered until the genotyping suggested that the lesion might be malignant and the pathology report examined a second time. By that time the report had been amended and it suggested that the tumor had undetermined malignant potential. Regarding the other tumors, all were examined a second time before array analysis to be certain that the tissue was representative and consistent with the pathology report. Therefore, this model was correct in assigning the diagnosis in all 10 cases.

Figure 3A:
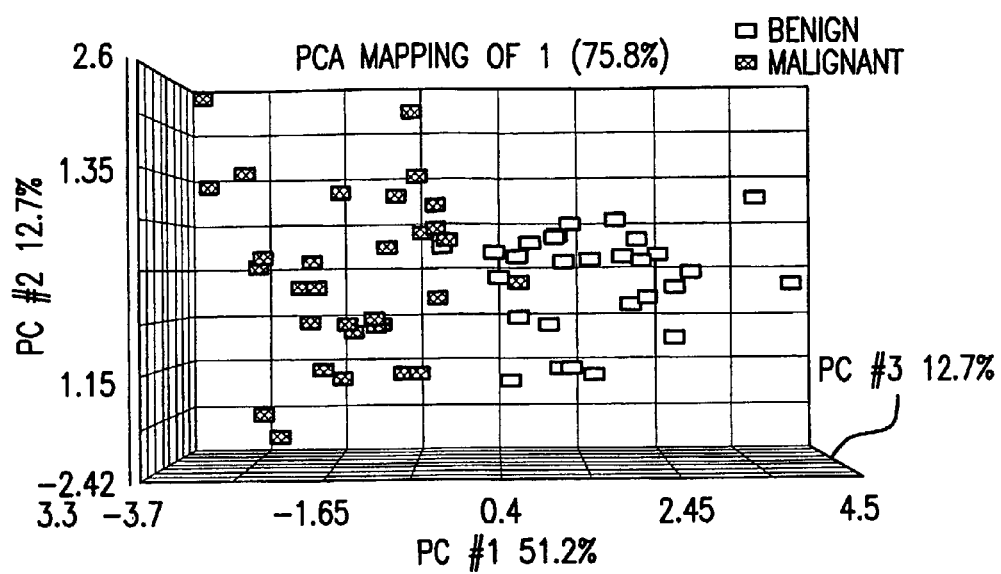
FIG. 3 shows PCA organization in a three-dimensional space of all samples with (A) and without the unknowns (B) based on the gene expressions values of the six most informative genes. It is clear there is a separation of the two groups and that it is possible to predict visually the diagnosis of each unknown. The pathological diagnoses of the unknowns are marked respectively with a + and a * for the benign and the malignant tumor. The red + sign indicates an unknown sample for which pathological diagnosis and predicted diagnosis were discordant. Based on our six gene diagnostic predictor model, this lesion was placed in the malignant group. Upon re-review by the pathologist, this sample was reclassified from benign to a neoplasm of uncertain malignant potential.
Figure 3B:
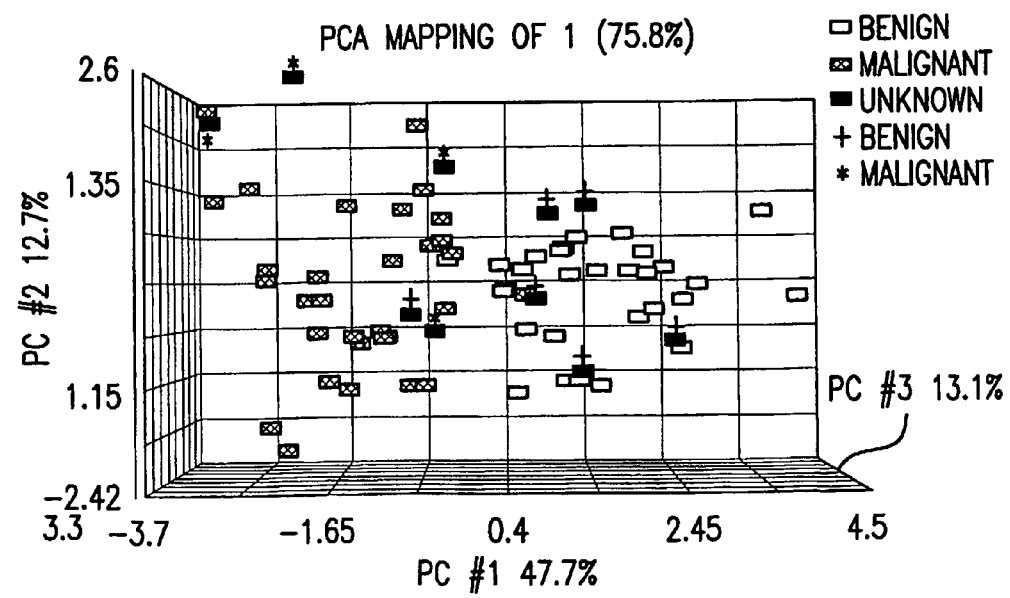

PCA analysis using only the six most informative genes was conducted on all the samples with and without the 10 unknown samples (FIG. 3A-B). It is clear from the PCA organization that the six genes strongly distinguish benign from malignant. In addition, these same genes can be used for diagnosis with respect to the four subcategories of thyroid lesion. Between the two-predictor models 11 genes are informative.

The identification of markers that can determine a specific type of tumor, predict patient outcome or the tumor response to specific therapies is currently a major focus of cancer research. This invention provides the use of gene expression profiling to build a predictor model able to distinguish a benign thyroid tumor from a malignant one. Such a model, when applied to FNA cytology, could greatly impact the clinical management of patients with suspicious thyroid lesions. To build the predictor model four types of thyroid lesions, papillary thyroid carcinoma (PTC), follicular variant of papillary thyroid carcinoma (FVPTC), follicular adenoma (FA) and hyperplastic nodules (HN) were used. Taken together, these represent the majority of thyroid lesions that often present as "suspicious". The choice of the appropriate control for comparative array experiments is often the subject of much discussion. In this case, in order to construct a predictive diagnostic algorithm based on a training set of samples, it was necessary to have a "common" reference standard to which all individual samples are compared. In this way, differences between each, and in fact all, samples could be analyzed. Had each tumor been compared to the adjacent normal thyroid tissue from the same patient, it would only be possible to comment on gene changes within each patient. A source of RNA from normal thyroid tissue was chosen since the source was replenishable and could be used for all of our future experiments once the diagnostic predictor algorithm was validated.

Figure 4:
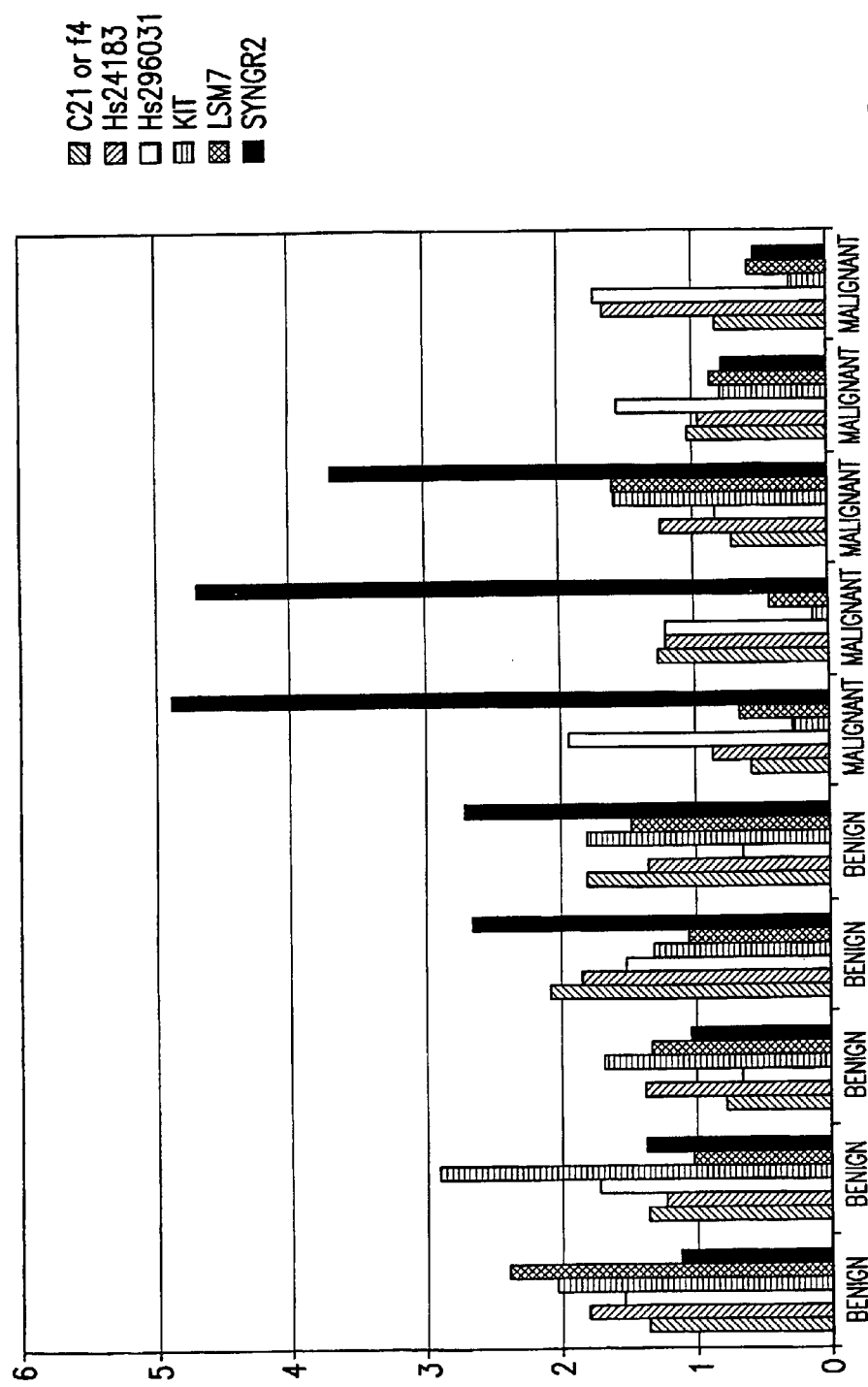
FIG. 4 is a graph showing gene expression profiles of ten unknown samples. On the basis of their profile the predictor model of this invention gave a correct diagnosis in 100% of the cases. The y axis represents the ratio between thyroid tumor mRNA expression level (Cy5 fluorescence intensity) and control thyroid tissue mRNA expression level (Cy3 fluorescence intensity).

The mRNA extracted from each sample was amplified. It was found that the quality of the arrays and the data derived from them is superior when mRNA has been amplified from total RNA. Of note, all samples and all reference controls were amplified in the same fashion. Analysis of the overall gene expression profiles revealed that the benign lesions (FA, HN) could be distinguished from the malignant lesions (PTC, FVPTC). Furthermore, although not statistically significant, the 4 tumor sub-types appeared to have different gene profiles. The use of a powerful statistical analysis program (Partek) helped discover a group of 11 genes that were informative enough to create a predictor model. Two combinations were created out of these 11 genes, a combination of six genes and a combination of 10 genes. PCA analysis of the six most informative genes resulted in a nearly perfect distinction between the two groups (FIG. 3A-B). In general, PCA analysis describes similarities between samples and is not a commonly employed tool for predicting diagnosis. However, in this study the distinction was so powerful that it was possible to visually make a correct diagnosis for each of the 10 unknown samples (FIG. 3A-B). The predictor model determines the kind of tumor with a specific probability value diagnosis of all 10 unknown samples was correctly predicted, with a more accurate prediction using the six-gene combination (Table 3, see probabilities). It is clear from the graph in FIG. 4 how the combination of gene expression values gives a distinctly different profile between the benign and malignant lesions. However, within each tumor group there are differences among the profiles of the five samples tested. This could be explained by the fact that each tumor, even if of the same type, could be at a different stage of progression.

Of the 11 genes that were informative for the diagnosis, five genes are known genes and for the other six genes no functional studies are yet available. The genes that were identified are the ones that the model has determined best group the known samples into their correct diagnosis. Those genes identified are the ones that consistently grouped the samples into the categories and subcategories described herein. This type of pattern assignment is based on the analysis of thousands of genes and the recognition by the computer software that certain patterns are associated repeatedly with certain diagnostic groups. This type of analysis derives it power (and significance) by the number of genes that are analyzed, rather than the degree of up or down regulation of any particular gene. With respect to the specific genes identified, the computer is not biased by the knowledge of previously identified associated with thyroid cancer. The genes it identifies are those that best differentiate the varied diagnoses of the known samples. This occurs during the "training" phase of establishing the algorithm. Once the computer is trained with data from comparisons of RNA from known diagnoses to a standard reference, unknowns can be tested and fit to the diagnostic groups predicted during the training. For the purposes of such an approach, individual genes are less important. A specific gene which is found in a univariate study to be associated with thyroid cancer, may not turn out to be the best multivariate predictor of a diagnosis in an analysis such as the one presented here.

TaqMan Assay Utilizing 6 Gene Predictor Model and 10 Gene Predictor Model

Utilizing the information obtained for these differentially expressed genes TaqMan Real Time PCR analysis for the group of 6 genes and the group of 10 genes that are diagnostic for benign versus malignant thyroid lesions from total RNA extracted from thyroid tissue as well as RNA from control normal thyroids was performed. TaqMan Real Time PCR analysis was also performed for the group of 10 genes that are diagnostic for benign versus malignant thyroid lesions.

Thyroid samples were collected under Johns Hopkins University Hospital Institutional Review Board-approved protocols. The samples were snap-frozen in liquid nitrogen and stored at −80° C. until use. The specimens were chosen based on their tumor type: papillary thyroid cancer (PTC); follicular variant of papillary thyroid cancer (FVPTC); follicular adenoma (FA); and hyperplastic nodule (HN). All diagnoses were made using standard clinical criteria by the Surgical Pathology Department at Johns Hopkins University Hospital.

Tissue Processing and Isolation of RNA

Frozen sections of 100-300 mg of tissue were collected in test tubes containing 1 ml of Trizol. Samples were transferred to FastRNA™ tubes containing mini beads and homogenized in a FastPrep beater (Bio101Savant™, Carlsbad, Calif.) for 1.5 min at speed 6. The lysate was transferred to a new tube and total RNA was extracted according to the Trizol protocol in a final volume of 40 µl Rnase-free water (Molecular Research Center, Inc., Cincinnati, Ohio). The quality of the extracted RNA was tested by spectrophotometry and by evaluation on minichips (BioAnalyzer; Agilent Technologies, Palo Alto, Calif.). Minimal criteria for a successful total RNA run were the presence of two ribosomal peaks and one marker peak. Normal human thyroid RNA (Clontech, BD Biosciences) served as a reference control. The total RNA extracted from tissue samples and normal thyroid was then used as the template for one round of reverse transcription to generate cDNA. Eight microliters of purified total RNA (containing up to 3 µg of total RNA) was added to a mix containing 3 µg/1 µl of random hexamer primers, 4 µl of 1× reverse transcription buffer, 2 µl of DTT, 2 µl of dNTPs, 1 µl of Rnase inhibitor, and 2 µl of SuperScript II reverse transcriptase (200 U/µl) in a 20 µl reaction volume (all purchased from Invitrogen, Carlsbad, Calif.). Reverse transcription was performed according to the SuperScript First-Strand Synthesis System instructions (Invitrogen, Carlsbad, Calif.). Following the reverse transcription reaction, the SuperScript II enzyme was heat inactivated, and degradation of the original template RNA was performed using 2 U/1 µl of RNAse H (Invitrogen, Carlsbad, Calif.) for 20 minutes at 37° C. The final volume of the mixture was brought to 500 µl using Rnase free water and stored at −20° C. until use.

Quantitative Real-Time PCR

For the quantitative analysis of mRNA expression, ABI Prism 7500 Sequence Detection System (Applied Biosystems) was used and the data analyzed using the Applied Biosystems 7500 System SDS Software Version 1.2.2. Primers and probes for the genes of interest and for G3PDH were designed using the Primer Express software (version 2.0; Applied Biosystems). Each primer was designed to produce an approximately 70-150 bp amplicon. Primer and probe sequences that can be utilized in the 6 gene predictor model and the 10 gene predictor model are listed in Table 4. Table 4 lists the forward and reverse primer for each gene as well as the fluorescent probe sequence that was dual labeled. Table 4 also provides the GenBank Accession No. corresponding to each gene and the location of the primer and probe sequences within the full-length nucleotide sequences provided under the GenBank Accession Nos. Table 4 also provides the InCytePD clone number for each gene (if available), a Unigene identification number for each gene (if available), the chromosomal location for each gene, and additional information about the primers and probes. The primer and probe sequences set forth in Table 4 are examples of the primers and probes that can be utilized to amplify and detect DET1-11. These examples should not be limiting as one of skill in the art would know that other primer sequences for DET1-DET11 including primers comprising the sequences set forth in Table 4 and fragments thereof can be utilized to amplify DET1-DET11. Similarly, other probes which specifically detect DET1-DET11 can be utilized such as probes that comprise the probe sequences set forth in Table 4 and fragments thereof.

Primers and probes were synthesized by Sigma (sequences shown in Table 4; Sigma, The Woodlands, Tex.). Probes were labeled at the 5' end with the reporter dye FAM (emission wavelength, 518 nm) and at the 3' end with the quencher dye TAMRA (emission wavelength, 582 nm). Standards were created for the six genes using gel-extracted PCR products (Qiagen, Valencia, Calif.). The G3PDH standard was created using a plasmid construct containing the relevant G3PDH sequence (kind gift of Dr. Tetsuya Moriuchi, Osaka University[12]). For PCR, 12.5 µl TaqMan Universal PCR Master Mix, 0.5 µl per well each of 0.5 µM forward and reverse primers, and 0.5 µl per well of 10 µM dual labelled fluorescent probe were combined and adjusted to a total volume of 20 µl with Rnase-free water. Finally, 5 µl cDNA per well was added to a total reaction volume of 25 µl. The PCR reaction was performed for 40 cycles of a two-step program: denaturation at 95° C. for 15 seconds, annealing and extension at 60° C. for 1 minute. The fluorescence was read at the completion of the 60° C. step. For each experiment, a no-template reaction was included as a negative control. Each cDNA sample was tested in triplicate, and the mean values were calculated. Triplicate values varied by no more than 10% from the mean. We used the standard curve absolute quantification technique to quantify copy number. A standard curve was generated using a ten-fold dilution series of four different known concentrations of the standards. The number of PCR cycles required for the threshold detection of the fluorescence signal (cycle threshold or Ct) was determined for each sample. Ct values of the standard samples were determined and plotted against the log amount of standard. Ct values of the unknown samples were then compared with the standard curve to determine the amount of target in the unknown sample. Standard curves from each experiment were compared to insure accurate, precise and reproducible results. Each plate contained duplicate copies of serial dilutions of known standards and G3PDH, triplicate copies of cDNA from each sample and normal thyroid cDNA for amplification of G3PDH and the gene of interest.

Statistical Analysis

Data from 41 of the thyroid tumors was used to build a benign (FA, n=15; HN, n=10) versus malignant (PTC, n=9; FVPTC, n=7) expression ratio-based model, capable of predicting the diagnosis (benign versus malignant) of each sample. Ten additional samples were provided as blinded specimens, processed as described above and used as a validation set to test the model. These ten samples were not previously used to do any other analysis. Expression values of all six genes in all samples and normal thyroid were standardized to the expression of G3PDH, a common housekeeping gene chosen to serve as a reference control. The ratio of the expression values for each gene in each sample was then compared to the ratio in normal thyroid, and converted to log 2 to generate a gene expression ratio value for all 41 samples. A file containing the gene expression ratio values from all 51 samples (41 known, 10 unknown) was imported into a statistical analysis software package (Partek, Inc., St. Charles, Mo.).

As a first step, the data from the 41 samples were subjected to principal component analysis (PCA) to provide a three-dimensional visualization of the data. All six genes were used to build a diagnosis-predictor model called a class prediction rule. This resulting rule was applied to predict the class of the ten samples in the validation set. The same analysis was then performed on a second set of data from 47 of the thyroid tumors to build a benign (FA, n=15; HN, n=11) versus malignant (PTC, n=9; FVPTC, n=12) expression ratio-based model. Ten additional unstudied samples were provided as blinded specimens for this second training set.

Principal Component Analysis (PCA) of the 41 samples using the gene expression values for all six genes showed a clear organization of the samples based on diagnosis. PCA was then conducted on all of the 41 samples with the 10 unknown samples. This combination of genes constituted a first predictor model and the validation set of 10 additional thyroid samples was used to confirm the accuracy of the model. The pathological diagnosis for each sample was kept blinded until after the analysis was completed. When the blind was broken, it was found that 8 of the 10 unknown samples were diagnosed by this model in concordance with the pathological diagnosis determined by standard pathologic criteria. One sample that was originally diagnosed as a benign follicular adenoma by standard histological criteria was diagnosed as malignant by the six gene predictor model set forth herein; one sample that was originally diagnosed as a papillary thyroid carcinoma by standard histological criteria was diagnosed as benign by the six gene predictor model set forth herein.

Further to the analysis above, the G3PDH standard was redesigned and processing of all tissue for total RNA extraction was standardized. Following these two modifications, Principal Component Analysis (PCA) was performed on the second training set of 47 samples and on ten new unknown samples using the gene expression values for all six genes. Again, PCA demonstrated a clear organization of the samples based on diagnosis. The pathological diagnosis for these ten new unknowns was also kept blinded until after the analysis. When the blind was broken, it was found that 9 of the samples were diagnosed in concordance with the pathological diagnosis by the six gene predictor model set forth herein. One sample that was diagnosed as a benign hyperplastic nodule by standard histological criteria was diagnosed as malignant by our model.

Figure 5:
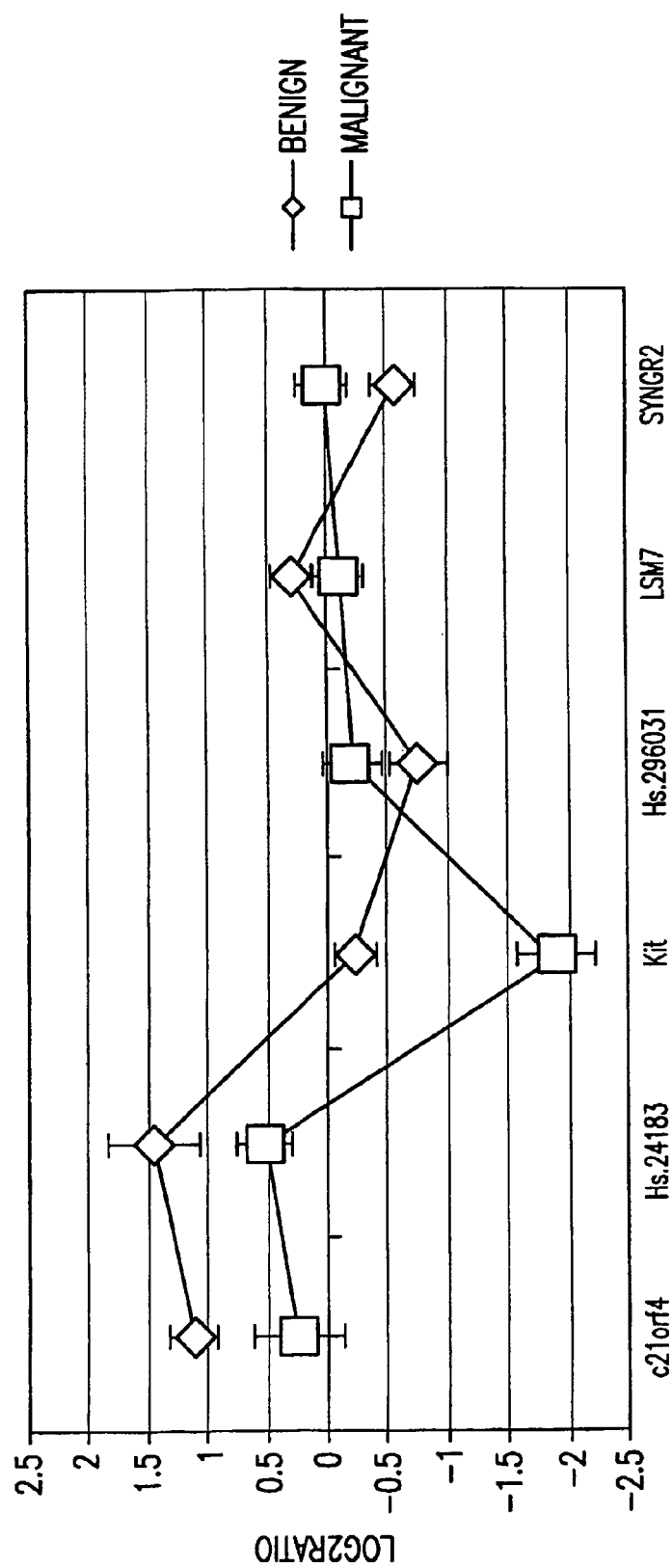
FIG. 5 shows the results of RT-PCR utilizing the 6 gene predictor model. The RT-PCR data using 6 genes across 42 patient samples demonstrates separation by group.
Figure 7:
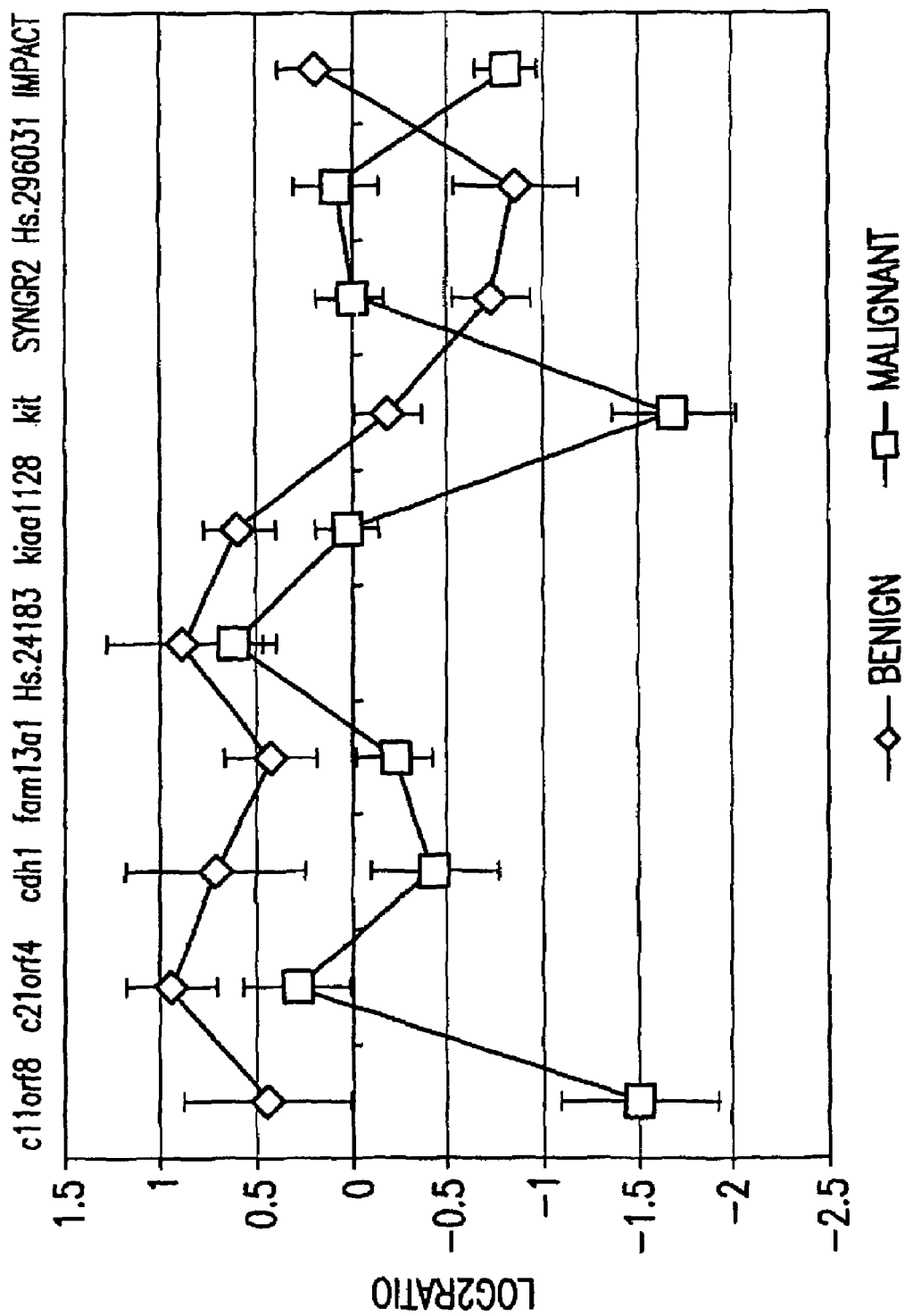
FIG. 7 shows the results of RT-PCR utilizing the 10 gene predictor model. The RT-PCR data using 10 genes demonstrates separation by group.

The results of the Taqman assays correlated with the microarray data. As shown in FIG. 5, the Taqman data utilizing the 6 gene model (DET1, DET2, DET3, DET4, DET5, DET6) demonstrates the ability to classify a thyroid sample as benign or malignant. Similar to results obtained via microarray, c21orf4, Hs.145049, KIT and LSM-7 were upregulated in benign samples as compared to malignant samples. In other words, the expression of c21orf4, Hs.145049, KIT and LSM7 decreases during malignancy. Hs.296031 and SYNGR2 were upregulated in malignant samples as compared to benign samples. In other words, expression of Hs.296031 and SYNGR2 increases during malignancy. The same analysis was performed with the 10 gene model utilizing the primers and probes set forth in Table 4 for DET1, DET2, DET3, DET4, DET6, DET7, DET8, DET9, DET10 and DET11. As shown in FIG. 7, similar to results obtained via microarray, c21orf4, Hs.145049 (Hs. 24183), KIT, FAM13A1, C11orf8, KIAA1128, IMPACT and CDH1 were upregulated in benign samples as compared to malignant samples. In other words, the expression of c21orf4, Hs.145049, KIT, FAM13A1, C11orf8, KIAA1128, IMPACT and CDH1 decreases during malignancy. Hs.296031 and SYNGR2 were upregulated in malignant samples as compared to benign samples. In other words, expression of Hs.296031 and SYNGR2 increases during malignancy. Therefore, it is clear that this pattern of differences between malignant and benign samples can be utilized to classify thyroid lesions utilizing the 6 gene model and the 10 gene model. In addition to classification, the Real Time PCR Taqman assay can also be used for staging thyroid cancer and in identifying agents that treat thyroid tumors.

Analysis of the 6 gene expression and the 10 gene expression profiles revealed that the benign lesions could be distinguished from the malignant lesions, and that this profile could be used to diagnose unknown samples against the current "gold standard" of pathologic criteria with a high degree of accuracy. Of the six genes in the six gene model, downregulation of kit was seen in both benign and malignant thyroid tissue when compared to normal control. The magnitude of this downregulation was much greater in malignant thyroid tissue. Kit is a well-known protooncogene.

As to the other five genes in the six gene model, for three of these no functional studies are yet available. Of the remaining two genes, SYNGR2 has been characterized as an integral vesicle membrane protein. LSM7 likewise has been described in the family of Sm-like proteins, possibly involved in pre-mRNA splicing. The interaction of LSM7 with the TACC1 complex may participate in breast cancer oncogenesis. However, the role of LSM7 in thyroid oncogenesis has not yet been explored.

The six gene model determined the accurate diagnosis of 17 out of 20 unknown samples tested. Accuracy was based on a comparison to the "gold standard" pathologic diagnosis as determined by clinical pathologists. Therefore, this strategy demonstrates the power of genomic analysis as a technique for studying the underlying pathways responsible for the pathophysiology of neuroendocrine tumors. Further evaluation and linkage of clinical data to molecular profiling allows for a better understanding of tumor pathogenesis, or even normal thyroid function and development. In addition, the use of qRT-PCR can lead to incorporation of this model and/or the 10 gene model into preoperative decision making for patients with thyroid nodules.

The present invention is a clear example of how gene-expression profiling can provide highly useful diagnostic information. It is likely that gene expression profiling will be used in the future for clinical decision-making. For this purpose adequate reporting of DNA-microarray data to clinicians will be necessary. Gene-expression profiles may be more reproducible and clinically applicable than well-established but highly subjective techniques, such as histopathology. The small number of genes for which RNA expression levels are diagnostically and prognostically relevant could lead to a robust, affordable, commercially available testing system. To this end, the present invention provides a useful method for classifying thyroid nodules as benign or malignant and therefore helps facilitate appropriate, and eliminate unnecessary, operations in patients with suspicious thyroid tumors.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

BIBLIOGRAPHY

1. Miller, L. D., Long, P. M., Wong, L., Mukherjee, S., McShane, L. M., and Liu, E. T. Optimal gene expression analysis by microarrays. Cancer Cell, 2: 353-361, 2002.
2. Sherman, S. I. Thyroid carcinoma. Lancet, 361: 501-511, 2003.
3. Schulze, A. and Downward, J. Navigating gene expression using microarrays—a technology review. Nat Cell Biol, 3: E190-195, 2001.
4. Raychaudhuri, S., Sutphin, P. D., Chang, J. T., and Altman, R. B. Basic microarray analysis: grouping and feature reduction. Trends Biotechnol, 19: 189-193, 2001.
5. Van't Veer, L. J. and De Jong, D. The microarray way to tailored cancer treatment. Nature Medicine, 8: 13, 2002.
6. Gordon, G. J., Jensen, R. V., Hsiao, L. L., Gullans, S. R., Blumenstock, J. E., Richards, W. G., Jaklitsch, M. T., Sugarbaker, D. J., and Bueno, R. Using gene expression ratios to predict outcome among patients with mesothelioma. J Natl Cancer Inst, 95: 598-605, 2003.
7. West, M., Blanchette, C., Dressman, H., Huang, E., Ishida, S., Spang, R., Zuzan, H., Olson, J. A., Jr., Marks, J. R., and Nevins, J. R. Predicting the clinical status of human breast cancer by using gene expression profiles. Proc Natl Acad Sci USA, 98: 11462-11467, 2001.
8. Mazzaferri, E. L. Management of a solitary thyroid nodule. N. Engl. J. Med., 328: 553-559, 1993.
9. Mazzaferri E L and S M, J. Long term impact of initial surgical and medical therapy on paillary and follicular thyroid cancer. Am J Pathol, 97: 418-428, 1994.
10. Goellner, J. R. Problems and pitfalls in thyroid cytology. Monogr Pathol 75-93, 1997.
11. Hamberger, B., et al Fine-needle aspiration biopsy of thyroid nodules. Impact on thyroid practice and cost of care. Am J Med, 73: 381-334, 1982.
12. Suen, K. C. How does one separate cellular follicular lesions of the thyroid by fine-needle aspiration biopsy? Diagn Cytopathol, 4: 78-81, 1988.
13. Goellner, J. R., et al., Fine needle aspiration cytology of the thyroid, 1980 to 1986. Acta Cytol, 31: 587-590, 1987.
14. Caraway, N. P., Sneige, N., and Samaan, N. A. Diagnostic pitfalls in thyroid fine-needle aspiration: a review of 394 cases. Diagn Cytopathol, 9: 345-350, 1993.
15. Ravetto, C., Colombo, L., and Dottorini, M. E. Usefulness of fine-needle aspiration in the diagnosis of thyroid carcinoma: a retrospective study in 37,895 patients. Cancer, 90: 357-363, 2000.
16. Gharib, H., Goellner, J. R., Zinsmeister, A. R., Grant, C. S., and Van Heerden, J. A. Fine-needle aspiration biopsy of the thyroid. The problem of suspicious cytologic findings. Ann Intern Med, 101: 25-28, 1984.

17. Staudt, L. M. Gene expression profiling of lymphoid malignancies. Annu Rev Med, 53: 303-318, 2002.

18. van de Vijver, M. J., He, Y. D., van't Veer, L. J., Dai, H., Hart, A. A., Voskuil, D. W., Schreiber, G. J., Peterse, J. L., Roberts, C., Marton, M. J., Parrish, M., Atsma, D., Witteveen, A., Glas, A., Delahaye, L., van der Velde, T., Bartelink, H., Rodenhuis, S., Rutgers, E. T., Friend, S. H., and Bernards, R. A gene-expression signature as a predictor of survival in breast cancer. N Engl J Med, 347: 1999-2009, 2002.

19. Sauter, G. and Simon, R. Predictive molecular pathology. N Engl J Med, 347: 1995-1996, 2002.

20. Simon, R., Radmacher, M. D., Dobbin, K., and McShane, L. M. Pitfalls in the use of DNA microarray data for diagnostic and prognostic classification. J Natl Cancer Inst, 95: 14-18, 2003.

21. Barden, C. B., Shister, K. W., Zhu, B., Guiter, G., Greenblatt, D. Y., M. A., Z., and Fahey, T. J. I. Classification of follicular thyroid tumors by molecular signature: results of gene profiling. Clinical Cancer Reserach, 9: 1792-1800, 2003.

22. Golub, T. R., Slonim, D. K., Tamayo, P., Huard, C., Gaasenbeek, M., Mesirov, J. P., Coller, H., Loh, M. L., Downing, J. R., Caligiuri, M. A., Bloomfield, C. D., and Lander, E. S. Molecular classification of cancer: class discovery and class prediction by gene expression monitoring. Science, 286: 531-537, 1999.

23. Eberwine, J. Amplification of mRNA populations using aRNA generated from immobilized oligo(dT)-T7 primed cDNA. Biotechniques, 20: 584-591, 1996.

24. Wang, E., Miller, L. D., Ohnmacht, G. A., Liu, E. T., and Marincola, F. M. High-fidelity mRNA amplification for gene profiling. Nat Biotechnol, 18: 457-459, 2000.

25. Feldman, A. L., Costouros, N. G., Wang, E., Qian, M., Marincola, F. M., Alexander, H. R., and Libutti, S. K. Advantages of mRNA amplification for microarray analysis. Biotechniques, 33: 906-912, 2002.

26. Barker, P. E., Besmer, P., and Ruddle, F. H. Human c-kit oncogene on human chromosome 4. Am. J. Hum. Genet., 37: A143, 1985.

27. De Miguel, M. P., Cheng, L., Holland, E. C., Federspiel, M. J., and Donovan, P.-J. Dissection of the c-Kit signaling pathways in mouse primordial germ cells by retroviral-mediated gene transfer. Proc. Nat. Acad. Sci., 99: 10458-10463, 2002.

28. Becker, K.-F., Atkinson, M. J., Reich, U., Becker, I., Nekarda, H., Siewert, J. R., and Hoefler, H. E-Cadherin gene mutations provide clues to diffuse type gastric carcinomas. Cancer Res., 54: 3845-3852, 1994.

29. Per, A., Wilgenbus, P., DAhl, P., Semb, H., and Christofori, G. A causal role for E-cadherin in the transition from adenoma to carcinoma. Nature, 392: 190-193, 1998.

30. Schwartz, F., Neve, R., Eisenman, R., Gessler, M., and Bruns, G. A WAGR region gene between PAX-6 and FSHB expressed in fetal brain. Hum. Genet., 94: 658-664, 1994.

TABLE 1

Two tail Anova analysis with Bonferroni correction resulted in 47 genes significantly different (p = <0.05) between the malignant and the benign group. The genes are listed from the most to the least significant. In bold are all the genes that combined together created the best predictor model.

| Gene | Bonferroni p-value | Mean (benign) | S.D.+/− | Mean (malignant) | S.D.+/− |
|---|---|---|---|---|---|
| C21orf4 | <0.0001 | 1.54 | 0.36 | 0.92 | 0.36 |
| KIT | <0.0001 | 1.20 | 0.66 | 0.38 | 0.32 |
| FLJ20477 | <0.0001 | 1.16 | 0.28 | 0.76 | 0.22 |
| MGC4276 | 0.0001 | 1.02 | 0.37 | 0.54 | 0.22 |
| KIAA0062 | 0.001 | 1.03 | 0.51 | 0.46 | 0.25 |
| CDH1 | 0.001 | 1.51 | 0.46 | 0.87 | 0.45 |
| LSM7 | 0.001 | 1.28 | 0.53 | 0.69 | 0.27 |
| ACYP1 | <0.01 | 2.11 | 0.91 | 1.09 | 0.51 |
| SYNGR2 | <0.01 | 0.75 | 0.41 | 1.87 | 1.05 |
| XPA | <0.01 | 2.29 | 0.84 | 1.31 | 0.58 |
| AD-017 | <0.01 | 1.57 | 0.63 | 0.84 | 0.44 |
| DP1 | <0.01 | 1.59 | 0.69 | 0.84 | 0.39 |
| IDI1 | <0.01 | 1.37 | 0.61 | 0.74 | 0.29 |
| RODH | <0.01 | 1.36 | 0.93 | 0.45 | 0.36 |
| ID4 | <0.01 | 1.10 | 0.56 | 0.48 | 0.37 |
| Hs.24183 | <0.01 | 2.05 | 0.70 | 1.30 | 0.42 |
| HTCD37 | <0.01 | 1.22 | 0.37 | 0.78 | 0.30 |
| DUSP5 | <0.01 | 0.97 | 0.60 | 3.93 | 3.15 |
| Hs.87327 | <0.01 | 1.54 | 0.53 | 1.01 | 0.26 |
| CRNKL1 | 0.01 | 1.33 | 0.49 | 0.79 | 0.34 |
| LOC54499 | 0.01 | 1.33 | 0.50 | 0.83 | 0.26 |
| RAP140 | 0.01 | 1.60 | 0.58 | 1.00 | 0.35 |
| MAPK4 | 0.01 | 0.66 | 0.38 | 0.30 | 0.16 |
| Hs.296031 | 0.01 | 1.13 | 0.63 | 2.28 | 1.12 |
| ATP6V1D | 0.01 | 1.71 | 0.75 | 0.94 | 0.46 |
| TXNL | 0.01 | 1.19 | 0.66 | 0.57 | 0.28 |
| FAM13A1 | 0.02 | 1.35 | 0.60 | 0.71 | 0.43 |
| GUK1 | 0.02 | 0.87 | 0.43 | 1.56 | 0.66 |
| Hs.383203 | 0.02 | 1.55 | 0.57 | 0.91 | 0.45 |
| C11orf8 | 0.02 | 0.81 | 0.43 | 0.36 | 0.30 |
| DENR | 0.02 | 1.54 | 0.42 | 1.02 | 0.42 |
| PRDX1 | 0.02 | 1.36 | 0.40 | 0.84 | 0.44 |
| FLJ20534 | 0.02 | 1.94 | 0.92 | 1.08 | 0.40 |
| DIO2 | 0.02 | 1.95 | 1.37 | 0.70 | 0.52 |
| C21orf51 | 0.02 | 1.01 | 0.40 | 0.63 | 0.22 |
| KIAA1128 | 0.03 | 1.76 | 0.87 | 0.90 | 0.52 |
| IMPACT | 0.03 | 1.32 | 0.48 | 0.86 | 0.27 |
| KIAA0089 | 0.03 | 1.43 | 0.63 | 0.76 | 0.49 |
| HSD17B4 | 0.03 | 1.45 | 0.57 | 0.88 | 0.36 |
| MAP4K5 | 0.04 | 1.59 | 0.61 | 0.97 | 0.44 |
| ELF3 | 0.04 | 0.82 | 0.24 | 1.45 | 0.72 |
| ALDH7A1 | 0.04 | 1.61 | 0.52 | 0.96 | 0.58 |
| BET1 | 0.04 | 1.38 | 0.55 | 0.82 | 0.39 |
| GTF2H2 | 0.04 | 1.80 | 0.54 | 1.23 | 0.44 |
| DC6 | 0.04 | 1.19 | 0.34 | 0.81 | 0.29 |
| CDH1 | 0.04 | 1.31 | 0.49 | 0.82 | 0.34 |

TABLE 2

Results of the cross validation analysis using the "leave-one out" method (see materials and methods). The predictor model was able to correctly predict 87% of the diagnoses. The outcome is called a confusion matrix.

| | # per Class | # Correct | # Error | % Correct | % Error |
|---|---|---|---|---|---|
| Benign | 31 | 27 | 4 | 87.1 | 12.9 |
| Malignant | 32 | 28 | 4 | 87.5 | 12.5 |
| Total | 63 | 55 | 8 | 87.3 | 12.7 |
| Normalized | | | | 87.3 | 12.7 |

TABLE 3

In this table the two predictor model of 10 and 6 genes is shown with their gene expression values, the predicted diagnosis, the percentage probability of the diagnosis being correct and the pathologic diagnosis. FA = follicular adenoma, HN = hyperplastic nodules, FVPTC = follicular variant papillary thyroid carcinoma and PTC = papillary thyroid carcinoma. The square indicates the unknown sample for which there was discordance between the predicted and the pathologic diagnosis. The percentage diagnosis probability for both 6 and 10 gene combinations strongly suggested that this was a malignant sample. The sample was re-reviewed by the pathologist and the pathologic diagnosis was in-fact changed to a neoplasm with uncertain malignant potential.

31 benign tumors
32 malignant tumors

DIAGNOSIS PREDICTOR MODEL

| 10 gene diagnose predictor model | | | | | | | | | | | cross validation of 83% | | % benign prob. | % malignant prob. | Predicted Diagnosis | Pathologic Diagnosis |
|---|---|---|---|---|---|---|---|---|---|---|---|---|---|---|---|---|
| C11 or f8 | C21 or f4 | CDH1 | FAM13A1 | Hs.24183 | Hs.296031 | IMPACT | KIAA1128 | KIT | SYNGR2 | | | | | | | |
| 0.4561 | 1.35 | 1.53 | 0.76 | 1.81 | 1.55 | 1.02 | 1.21 | 2.03 | 1.12 | | | 0.99 | 0.01 | benign | FA |
| 0.4988 | 0.82 | 0.83 | 0.45 | 1.67 | 1.74 | 0.98 | 1.27 | 0.27 | 0.54 | | | 0.02 | 0.98 | malignant | FVPTC |
| 1.1311 | 0.78 | 2.13 | 1.13 | 1.39 | 0.65 | 1.35 | 1.19 | 1.70 | 1.04 | | | 0.91 | 0.09 | benign | HN |
| 0.5143 | 1.05 | 0.62 | 0.85 | 0.95 | 1.56 | 1.16 | 0.86 | 0.80 | 0.79 | | | 0.43 | 0.57 | malignant | PTC |
| 0.3786 | 2.07 | 0.64 | 1.44 | 1.84 | 1.51 | 0.48 | 1.14 | 1.32 | 2.65 | | | 0.94 | 0.06 | benign | FA |
| 0.7376 | 1.81 | 0.85 | 1.85 | 1.34 | 0.65 | 0.91 | 1.56 | 1.83 | 2.70 | | | 1.00 | 0.00 | benign | FA |
| 0.1206 | 0.57 | 0.50 | 0.55 | 0.86 | 1.94 | 0.61 | 0.99 | 0.25 | 4.88 | | | 0.00 | 1.00 | malignant | PTC |
| 0.026 | 1.27 | 0.46 | 0.59 | 1.22 | 1.19 | 0.91 | 0.56 | 0.11 | 4.69 | | | 0.00 | 1.00 | malignant | PTC |
| 0.1097 | 0.70 | 2.17 | 1.01 | 1.24 | 0.82 | 0.95 | 0.93 | 1.59 | 3.69 | | | 0.05 | 0.95 | [malignant] | [HN] |
| 1.0368 | 1.37 | 1.24 | 1.50 | 1.23 | 1.74 | 0.94 | 1.82 | 2.92 | 1.38 | | | 1.00 | 0.00 | benign | HN |

| 6 gene diagnose predictor model | | | | | | cross validation of 87% | | % benign prob. | % malignant prob. | Predicted Diagnosis | Pathologic Diagnosis |
|---|---|---|---|---|---|---|---|---|---|---|---|
| C21 or f4 | Hs.24183 | Hs.296031 | KIT | LSM7 | SYNGR2 | | | | | | |
| 1.3518 | 1.81 | 1.55 | 2.03 | 2.40 | 1.12 | | | 1.00 | 0.00 | benign | FA |
| 0.819 | 1.67 | 1.74 | 0.27 | 0.56 | 0.54 | | | 0.15 | 0.85 | malignant | FVPTC |
| 0.7822 | 1.39 | 0.65 | 1.70 | 1.33 | 1.04 | | | 0.94 | 0.06 | benign | HN |
| 1.0457 | 0.95 | 1.56 | 0.80 | 0.85 | 0.79 | | | 0.33 | 0.67 | malignant | PTC |
| 2.0723 | 1.84 | 1.51 | 1.32 | 1.05 | 2.65 | | | 0.86 | 0.14 | benign | FA |
| 1.8053 | 1.34 | 0.65 | 1.83 | 1.47 | 2.70 | | | 0.96 | 0.04 | benign | FA |
| 0.5666 | 0.86 | 1.94 | 0.25 | 0.66 | 4.88 | | | 0.00 | 1.00 | malignant | PTC |
| 1.2698 | 1.22 | 1.19 | 0.11 | 0.43 | 4.69 | | | 0.00 | 1.00 | malignant | PTC |
| 0.698 | 1.24 | 0.82 | 1.59 | 1.60 | 3.69 | | | 0.10 | 0.90 | [malignant] | [HN] |
| 1.3677 | 1.23 | 1.74 | 2.92 | 1.04 | 1.38 | | | 0.99 | 0.01 | benign | HN |

TABLE 4

Thyroid Primer/Probes

| Oligo Name | | Length | Sequence(5'-3') | Tm |
|---|---|---|---|---|
| Hs.24183-Forward | SEQ ID NO: 1 | 22 | ggctgactggcaaaaagtcttg | |
| Hs.24183-Reverse | SEQ ID NO: 2 | 26 | ttggttcccttaagttctcagagttt | |
| Hs.24183-Probe | SEQ ID NO: 3 | 23 | (6Fam)TggCCCTgTCACTCCCATgATgC(Tamra) | |
| thyroglobulin-forward | SEQ ID NO: 4 | 18 | aagggctcgcatgcaaag | 59 |
| thyroglobulin-reverse | SEQ ID NO: 5 | 25 | cacagtagcactctgagttgaagca | 60 |
| thyroglobulin-probe | SEQ ID NO: 6 | 33 | (6Fam)TTTgTCCCTgCTTgTACTAgTgAgg(Tamra) | 69 |
| c21orf4-forward | SEQ ID NO: 7 | 22 | gcaatcctcttacctccgcttt | |
| c21orf4-reverse | SEQ ID NO: 8 | 25 | ggaatcggagaccagaagagagctt | |
| c21orf4-Probe | SEQ ID NO: 9 | 28 | (6Fam)CTgggACCACAgATgTATCCTCCACTCC(Tamra) | |
| fam13a1-forward | SEQ ID NO: 10 | 22 | atggcagtgcagtcatcatctt | |
| fam13a1-reverse | SEQ ID NO: 11 | 25 | gcattcatacagctgcttaccatct | |
| fam13a1-Probe | SEQ ID NO: 12 | 23 | (6Fam)TTTgTCCCTgCCTAggACCggg(Tamra) | |
| c11orf8-forward | SEQ ID NO: 13 | 16 | ccggcccaagctccat | |
| c11orf8-reverse | SEQ ID NO: 14 | 21 | ttgtgtaaccgtcggtcatga | |
| c11orf8-Probe | SEQ ID NO: 15 | 29 | (6Fam)TgTTTggTggAATCCATgAAggTTATggC(Tamra) | |
| kiaa1128-forward | SEQ ID NO: 16 | 20 | gagagcgtgatcccctaca | |
| kiaa1128-reverse | SEQ ID NO: 17 | 23 | accaagagtgcacctcagtgtct | |
| kiaa1128-probe | SEQ ID NO: 18 | 33 | (6Fam)TCACTTCCAAATgTTCCTgTAgCATAAATggTg(Tamra) | |
| Hs.296031-forward | SEQ ID NO: 19 | 24 | tgccaaggagctttgtttatagaa | |
| Hs.296031-reverse | SEQ ID NO: 20 | 20 | atgacggcatgtaccaacca | |
| Hs.296031-probe | SEQ ID NO: 21 | 29 | (6Fam)TTggTCCCCTCAgTTCTATgCTgTTgTgT(Tamra) | |
| kit-forward | SEQ ID NO: 22 | 26 | gcacctgctgaaatgtatgacataat | |
| kit-reverse | SEQ ID NO: 23 | 28 | tttgctaagttggagtaaatatgattgg | |
| kit-probe | SEQ ID NO: 24 | 36 | (6Fam)ATTgTTCAgCTAATTgAgAAgCAgATTTCAgAgAgC(Temra) | |
| impact-forward | SEQ ID NO: 25 | 26 | tgaagaatgtcatggtggtagtatca | |
| impact-reverse | SEQ ID NO: 26 | 26 | atgactctcaggtgaatttgtgtag | |
| impact-probe | SEQ ID NO: 27 | 29 | (6Fam)CTggTATggAgggATTCTgCTAggACCAg(Tamra) | |
| cdh1-forward | SEQ ID NO: 28 | 21 | tgagtgtccccggtatcttc | |
| cdh1-reverse | SEQ ID NO: 29 | 21 | cagccgctttcagattttcat | |

TABLE 4-continued

| | | | |
|---|---|---|---|
| cdh1-probe | SEQ ID NO: 30 | 27 | (6Fam)CCTgCCAATCCCgATgAAATTggAAAT(Tamra) |
| syngr2-forward | SEQ ID NO: 31 | 19 | gctggtgctcatggcactt |
| syngr2-reverse | SEQ ID NO: 32 | 19 | ccctccccaggcttcctaa |
| syngr2-probe | SEQ ID NO: 33 | 24 | (6Fam)aagggctttgcctgacaacaccca(Tamra) |
| lsm7-forward | SEQ ID NO: 34 | 21 | gacgatccgggtaaagttcca |
| lsm7-reverse | SEQ ID NO: 35 | 20 | aggttgaggagtgggtcgaa |
| lsm7-probe | SEQ ID NO: 36 | 22 | (6Fam)aggccgcgaagccagtggaatc(Tamra) |
| G3PDH-Forward | SEQ ID NO: 37 | 22 | TCACCAGGGCTGCTTTTAACTC |
| G3PDH-Reverse | SEQ ID NO: 38 | 26 | GGAATCATATTGGAACATGTAAACCA |
| G3PDH-probe | SEQ ID NO: 39 | 27 | FAM-TTGCCATCAATGACCCCTTCATTGACC-TAMRA |
| normal thyroid sample | | Clontec | Lot 63100284 |

| Thyroid Primer/Probes Oligo Name | Residues | InCytePD Clone | ret = retired Unigene | CM Paper GenBank/RefSeq |
|---|---|---|---|---|
| Hs.24183-Forward | 2436-2457 | 2123020 | Hs24183 | NP060265 |
| Hs.24183-Reverse | 2530-2505 | 2123020 | Hs24183 | NP060265 |
| Hs.24183-Probe | 2462-2484 | 2123020 | Hs24183 | NP060265 |
| thyroglobulin-forward | 2036-2053 | | | NM_003235 |
| thyroglobulin-reverse | 2157-2133 | | | NM_003235 |
| thyroglobulin-probe | 2088-2120 | | | NM_003235 |
| c21orf4-forward | 2622-2643 | 1710736 | (Hs284142-ret)Hs433668 | AP001717 |
| c21orf4-reverse | 2743-2712 | 1710736 | (Hs284142-ret)Hs433668 | AP001717 |
| c21orf4-Probe | 2652-2679 | 1710736 | (Hs284142-ret)Hs433668 | AP001717 |
| fam13a1-forward | 2931-2952 | 1458366 | (Hs177644-removed)Hs.442818 | (NM014883)fromAB020721 |
| fam13a1-reverse | 3058-3034 | 1458366 | (Hs177644-removed)Hs.442818 | (NM014883)fromAB020721 |
| fam13a1-Probe | 2992-3014 | 1458366 | (Hs177644-removed)Hs.442818 | (NM014883)fromAB020721 |
| c11orf8-forward | 849-864 | 4117578 | (Hs46638-ret) Hs.432000 | NM001584 |
| c11orf8-reverse | 916-896 | 4117578 | (Hs46638-ret) Hs.432000 | NM001584 |
| c11orf8-Probe | 866-894 | 4117578 | (Hs46638-ret) Hs.432000 | NM001584 |
| kiaa1128-forward | 5980-5999 | 1428225 | Hs81897 | AB032914.1-this is actually AB032954.1 |
| kiaa1128-reverse | 6063-6041 | 1428225 | Hs81897 | AB032914.1-this is actually AB032954.1 |
| kiaa1128-probe | 6004-6036 | 1428225 | Hs81897 | AB032914.1-this is actually AB032954.1 |
| Hs.296031-forward | 4271-4294 | 29557644 | Hs296031 | BC38512.1 |
| Hs.296031-reverse | 4353-4334 | 29557644 | Hs296031 | BC38512.1 |
| Hs.296031-probe | 4301-4329 | 29557644 | Hs296031 | BC38512.1 |
| kit-forward | 2704-2729 | 2358031/1672225 | Hs81665 | XO6182.1 |
| kit-reverse | 2843-2816 | 2358031/1672225 | Hs81665 | XO6182.1 |
| kit-probe | 2779-2814 | 2358031/1672225 | Hs81665 | XO6182.1 |
| impact-forward | 809-834 | 973364 | Hs284245 | NM018439 |
| impact-reverse | 943-918 | 973364 | Hs284245 | NM018439 |
| impact-probe | 837-865 | 973364 | Hs284245 | NM018439 |
| cdh1-forward | 2499-2519 | 2793857/1858050/1208946 | HS194657 | NM004360 |
| cdh1-reverse | 2579-2559 | 2793857/1858050/1208946 | HS194657 | NM004360 |
| cdh1-probe | 2525-2551 | 2793857/1858050/1208946 | HS194657 | NM004360 |
| syngr2-forward | 1255-1273 | 983008 | (Hs5097-ret) Hs.433753 | NM004710.2 |
| syngr2-reverse | 1374-1356 | 983008 | (Hs5097-ret) Hs.433753 | NM004710.2 |
| syngr2-probe | 1303-1326 | 983008 | (Hs5097-ret) Hs.433753 | NM004710.2 |
| lsm7-forward | 72-92 | 1911913/2060560 | (Hs70830-ret)Hs.512610 | NM0161991.1 |
| lsm7-reverse | 146-127 | 1911913/2060560 | (Hs70830-ret)Hs.512610 | NM0161991.1 |
| lsm7-probe | 96-117 | 1911913/2060560 | (Hs70830-ret)Hs.512610 | NM0161991.1 |
| G3PDH-Forward | 128-149 | | | |
| G3PDH-Reverse | 228-203 | | | |
| G3PDH-probe | 167-193 | | | |
| normal thyroid sample | pooled | 65 autopsy patients | 650-424-8222 | |

| Thyroid Primer/Probes Oligo Name | TAQman GenBank/RefSeq | Chromosome | Primer/Probe Details |
|---|---|---|---|
| Hs.24183-Forward | AL832414.1 | ?1 | used later part of sequence |
| Hs.24183-Reverse | AL832414.1 | | |
| Hs.24183-Probe | AL832414.1 | | |
| thyroglobulin-forward | NM_003235 | | used within Exon 9 |
| thyroglobulin-reverse | NM_003235 | | |
| thyroglobulin-probe | NM_003235 | | |
| c21orf4-forward | NM_006134.4 | 21q22.11 | spans Exon 7-8 |
| c21orf4-reverse | NM_006134.4 | | |
| c21orf4-Probe | NM_006134.4 | | |
| fam13a1-forward | (NM014883)fromAB020721 | 4q22.1 | used later part of seq-exon 19 |
| fam13a1-reverse | (NM014883)fromAB020721 | | |
| fam13a1-Probe | (NM014883)fromAB020721 | | |
| c11orf8-forward | NM001584 | 11p13 | spans Exon 5-6 |
| c11orf8-reverse | NM001584 | | |
| c11orf8-Probe | NM001584 | | |
| kiaa1128-forward | AB032954.1 | 10q23.2 | used later part of sequence |
| kiaa1128-reverse | AB032954.1 | | |
| kiaa1128-probe | AB032954.1 | | |

TABLE 4-continued

| | | | |
|---|---|---|---|
| Hs.296031-forward | BC38512.1 | X | used later part of sequence |
| Hs.296031-reverse | BC38512.1 | | |
| Hs.296031-probe | BC38512.1 | | |
| kit-forward | XO6182.1 | 4q11-q12 | spans Exon 19-20 |
| kit-reverse | XO6182.1 | | |
| kit-probe | XO6182.1 | | |
| impact-forward | NM018439 | 18q11.2-q12.1 | spans Exon 10-11 |
| impact-reverse | NM018439 | | |
| impact-probe | NM018439 | | |
| cdh1-forward | NM004360 | 16q22.1 | spans Exon 15-16 |
| cdh1-reverse | NM004360 | | |
| cdh1-probe | NM004360 | | |
| syngr2-forward | NM004710.2 | 17q25.3 | used later sequence |
| syngr2-reverse | NM004710.2 | | |
| syngr2-probe | NM004710.2 | | |
| lsm7-forward | NM0161991.1 | 19p13.3 | used later sequence |
| lsm7-reverse | NM0161991.1 | | |
| lsm7-probe | NM0161991.1 | | |
| G3PDH-Forward | NM_002046 | | from Takahashi paper |
| G3PDH-Reverse | NM_002046 | | |
| G3PDH-probe | NM_002046 | | |
| normal thyroid sample | | | |

What is claimed is:

1. A method for classifying a thyroid lesion in a subject as benign or malignant comprising:
   a) measuring the expression of differentially expressed thyroid (DET) gene C21orf4, Hs.145049, Hs.296031, KIT, SYNGR2, C11orf8, CDH1, FAM13A1, IMPACT, and KIAA1128, in a test cell population obtained from the thyroid lesion in the subject;
   b) comparing the expression of said DET genes in the test cell population to the expression of said DET genes in normal thyroid tissue thereby creating an expression ratio pattern for the test cell population; and
   c) using Principal Component Analysis to compare the expression ratio-based pattern in the test cell population to the expression ratio-based pattern of cells from a benign thyroid lesion and cells from a malignant thyroid lesion, thereby classifying the thyroid lesion in the subject as benign or malignant.

2. The method of claim 1, wherein the expression of said DET genes in normal thyroid tissue is measured in a plurality of cells or is derived from a database.

3. The method of claim 1, wherein the benign lesion is selected from the group consisting of: a follicular adenoma, hyperplastic nodule, papillary adenoma, thyroiditis nodule and multinodular goiter.

4. The method of claim 1, wherein the malignant thyroid lesion is selected from the group consisting of: papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angiosarcoma.

5. The method of claim 1, wherein the subject is a human.

6. The method of claim 1, wherein expression of the DET genes are measured by microarray.

7. The method of claim 1, wherein expression of the DET genes are measured by probing the nucleic acid(s).

8. The method of claim 1, wherein expression of the DET genes are measured by amplifying the nucleic acid(s).

9. The method of claim 1, wherein the expression of the DET genes are measured by amplifying the DET nucleic acid(s) and detecting the amplified nucleic acid with a fluorescent probe.

10. The method of claim 9, wherein C21orf4 nucleic acid is amplified utilizing forward primer GCAATCCTCTTAC-CTCCGCTTT (SEQ ID NO: 7) and reverse primer GGAATCGGAGACAGAAGAGAGCTT (SEQ ID NO: 8) and wherein the amplified nucleic acid is detected with a probe comprising the nucleic acid sequence CTGGGACCA-CAGATGTATCCTCCACTCC (SEQ ID NO: 9) linked to a fluorescent label.

11. The method of claim 9, wherein Hs.145049 nucleic acid is amplified utilizing forward primer GGCTGACTG-GCAAAAAGTCTTG (SEQ ID NO: 1) and reverse primer TTGGTTCCCTTAAGTTCTCAGAGTTT (SEQ ID NO: 2) and wherein the amplified nucleic acid is detected with a probe comprising the nucleic acid sequence TGGCCCTGT-CACTCCCATGATGC (SEQ ID NO: 3) linked to a fluorescent label.

12. The method of claim 9, wherein Hs.296031 nucleic acid is amplified utilizing forward primer TGCCAAG-GAGCTTTGTTTATAGAA (SEQ ID NO: 19) and reverse primer ATGACGGCATGTACCAACCA (SEQ ID NO: 20) and wherein the amplified nucleic acid is detected with a probe comprising the nucleic acid sequence TTGGTCCCCT-CAGTTCTATGCTGTTGTGT (SEQ ID NO: 21) linked to a fluorescent label.

13. The method of claim 9, wherein KIT nucleic acid is amplified utilizing forward primer GCACCTGCTGAAATG-TATGACATAAT (SEQ ID NO: 22) and reverse primer TTTGCTAAGTTGGAGTAAATATGATTGG (SEQ ID NO: 23) and wherein the amplified nucleic acid is detected with a probe comprising the nucleic acid sequence ATTGT-TCAGCTAATTGAGAAGCAGATTTCAGAGAGC (SEQ ID NO: 24) linked to a fluorescent label.

14. The method of claim 9, wherein SYNGR2 nucleic acid is amplified utilizing forward primer GCTGGTGCTCATG-GCACTT (SEQ ID NO: 31) and reverse primer CCCTC-CCCAGGCTTCCTAA (SEQ ID NO: 32) and wherein the amplified nucleic acid is detected with a probe comprising the nucleic acid sequence AAGGGCTTTGCCTGACAACAC-CCA (SEQ ID NO: 33) linked to a fluorescent label.

15. The method of claim 9, wherein C11orf8 nucleic acid is amplified utilizing forward primer CCGGCCCAAGCTC-CAT (SEQ ID NO: 13) and reverse primer TTGTGTAAC-CGTCGGTCATGA (SEQ ID NO: 14) and wherein the amplified nucleic acid is detected with a probe comprising the nucleic acid sequence TGTTTGGTGGAATCCATGAAG-GTTATGGC (SEQ ID NO: 15) linked to a fluorescent label.

16. The method of claim 9, wherein CDH1 nucleic acid is amplified utilizing forward primer TGAGTGTCCCCCGG-TATCTTC (SEQ ID NO: 28) and reverse primer CAGC-CGCTTTCAGATTTTCAT (SEQ ID NO: 29) and wherein the amplified nucleic acid is detected with a probe comprising the nucleic acid sequence CCTGCCAATCCCGATGAAAT-TGGAAAT (SEQ ID NO: 30) linked to a fluorescent label.

17. The method of claim 9, wherein IMPACT nucleic acid is amplified utilizing forward primer ATGGCAGTGCAGT-CATCATCTT (SEQ ID NO: 10) and reverse primer GCAT-TCATACAGCTGCTTACCATCT (SEQ ID NO: 11) and the amplified nucleic acid is detected with a probe comprising the nucleic acid sequence TTTGGTCCCTGCCTAGGAC-CGGG (SEQ ID NO: 12) linked to a fluorescent label.

18. The method of claim 9, wherein FAM13A1 nucleic acid is amplified utilizing forward primer TGAAGAATGT-CATGGTGGTAGTATCA (SEQ ID NO: 25) and reverse primer ATGACTCCTCAGGTGAATTTGTGTAG (SEQ NO: 26) and wherein the amplified nucleic acid is detected with a probe comprising the nucleic acid sequence CTGG-TATGGAGGGATTCTGCTAGGACCAG (SEQ ID NO: 27) linked to a fluorescent label.

19. The method of claim 9, wherein KIAA1128 nucleic acid is amplified utilizing forward primer GAGAGCGT-GATCCCCCTACA (SEQ ID NO: 16) and reverse primer ACCAAGAGTGCACCTCAGTGTCT (SEQ ID NO: 17) and the amplified nucleic acid is detected with a probe comprising the nucleic acid sequence TCACTTCCAAATGTTCCTG-TAGCATAAATGGTG (SEQ ID NO: 18) linked to a fluorescent label.

20. A method for classifying a thyroid lesion in a subject as benign or malignant comprising:
   a) measuring the expression of differentially expressed thyroid (DET) genes C21orf4, Hs.145049, Hs.296031, KIT, LSM7, and SYNGR2, in a test cell population obtained from the thyroid lesion in the subject;
   b) comparing the expression of said DET genes in the test cell population to the expression of said DET genes in normal thyroid tissue thereby creating an expression ratio pattern for the test cell population; and
   c) using Principal Component Analysis to compare the expression ratio-based pattern in the test cell population to the expression ratio-based pattern of cells from a benign thyroid lesion and cells from a malignant thyroid lesion, thereby classifying the thyroid lesion in the subject as benign or malignant.

21. The method of claim 20, wherein the expression of said DET genes in normal thyroid tissue is measured in a plurality of cells or is derived from a database.

22. The method of claim 20, the benign lesion is selected from the group consisting of: a follicular adenoma, hyperplastic nodule, papillary adenoma, thyroiditis nodule and multinodular goiter.

23. The method of claim 20, wherein the malignant thyroid lesion is selected from the group consisting of: papillary thyroid carcinoma, follicular variant of papillary thyroid carcinoma, follicular carcinoma, Hurthle cell tumor, anaplastic thyroid cancer, medullary thyroid cancer, thyroid lymphoma, poorly differentiated thyroid cancer and thyroid angio sarcoma.

24. The method of claim 20, wherein the subject is a human.

25. The method of claim 20, wherein expression of the DET genes are measured by microarray.

26. The method of claim 20, wherein expression of the DET genes are measured by probing the nucleic acid(s).

27. The method of claim 20, wherein expression of the DET genes are measured by amplifying the nucleic acid(s).

28. The method of claim 20, wherein the expression of the DET genes are measured by amplifying the nucleic acid(s) and detecting the amplified nucleic acid with a fluorescent probe.

29. The method of claim 28, wherein C21orf4 nucleic acid is amplified utilizing forward primer GCAATCCTCTTAC-CTCCGCTTT (SEQ ID NO: 7) and reverse primer GGAATCGGAGACAGAAGAGAGCTT (SEQ ID NO: 8) and wherein the amplified nucleic acid is detected with a probe comprising the nucleic acid sequence CTGGGACCA-CAGATGTATCCTCCACTCC (SEQ ID NO: 9) linked to a fluorescent label.

30. The method of claim 28, wherein Hs.145049 nucleic acid is amplified utilizing forward primer GGCTGACTG-GCAAAAAGTCTTG (SEQ ID NO: 1) and reverse primer TTGGTTCCCTTAAGTTCTCAGAGTTT (SEQ ID NO: 2) and wherein the amplified nucleic acid is detected with a probe comprising the nucleic acid sequence TGGCCCTGT-CACTCCCATGATGC (SEQ ID NO: 3) linked to a fluorescent label.

31. The method of claim 28, wherein Hs.296031 nucleic acid is amplified utilizing forward primer TGCCAAG-GAGCTTTGTTTATAGAA (SEQ ID NO: 19) and reverse primer ATGACGGCATGTACCAACCA (SEQ ID NO: 20) and wherein the amplified nucleic acid is detected with a probe comprising the nucleic acid sequence TTGGTCCCCT-CAGTTCTATGCTGTTGTGT (SEQ ID NO: 21) linked to a fluorescent label.

32. The method of claim 28, wherein KIT nucleic acid is amplified utilizing forward primer GCACCTGCTGAAATG-TATGACATAAT (SEQ ID NO: 22) and reverse primer TTTGCTAAGTTGGAGTAAATATGATTGG (SEQ ID NO: 23) and wherein the amplified nucleic acid is detected with a probe comprising the nucleic acid sequence ATTGT-TCAGCTAATTGAGAAGCAGATTTCAGAGAGC (SEQ ID NO: 24) linked to a fluorescent label.

33. The method of claim 28, wherein LSM7 nucleic acid is amplified utilizing forward primer GACGATCCGGG-TAAAGTTCCA (SEQ ID NO: 34) and reverse primer AGGTTGAGGAGTGGGTCGAA (SEQ ID NO: 35) and wherein the amplified nucleic acid is detected with a probe comprising the nucleic acid sequence AGGCCGCGAAGC-CAGTGGAATC (SEQ ID NO: 36) linked to a fluorescent label.

34. The method of claim 28, wherein SYNGR2 nucleic acid is amplified utilizing forward primer GCTGGTGCT-CATGGCACTT (SEQ ID NO: 31) and reverse primer CCCTCCCCAGGCTTCCTAA (SEQ ID NO: 32) and wherein the amplified nucleic acid is detected with a probe comprising the nucleic acid sequence AAGGGCTTTGCCT-GACAACACCCA (SEQ ID NO: 33) linked to a fluorescent label.

35. The method of claim 1, wherein C21orf4 consists of the nucleic acid sequence SEQ ID NO:40, Hs.145049 consists of the nucleic acid sequence SEQ ID NO:42, Hs.296031 consists of the nucleic acid sequence SEQ ID NO:44, KIT consists of the nucleic acid sequence SEQ ID NO:45, SYNGR2 consists of the nucleic acid sequence SEQ ID NO:49, C11orf8 consists of the nucleic acid sequence SEQ ID NO:51, CDH1 consists of the nucleic acid sequence SEQ ID NO:53, IMPACT consists of the nucleic acid sequence SEQ ID NO:55, FAM13A1 consists of the nucleic acid sequence SEQ ID NO:57, and KIAA1128 consists of the nucleic acid sequence SEQ ID NO:59.

36. The method of claim 20, wherein C21orf4 consists of the nucleic acid sequence SEQ ID NO:40, Hs.145049 consists of the nucleic acid sequence SEQ ID NO:42, Hs.296031 consists of the nucleic acid sequence SEQ ID NO:44, KIT consists of the nucleic acid sequence SEQ ID NO:45, LSM7 consists of the nucleic acid sequence SEQ ID NO:47, and SYNGR2 consists of the nucleic acid sequence SEQ ID NO:49.

* * * * *